United States Patent
Ragan et al.

(10) Patent No.: US 11,162,902 B2
(45) Date of Patent: Nov. 2, 2021

(54) METASURFACES COMPRISED OF NANOSPHERE OLIGOMERS WITH UNIFORM NARROW GAP SPACINGS, THEIR METHOD OF FABRICATION AND APPLICATIONS IN SENSING

(71) Applicant: The Regents of the University of California, Oakland, CA (US)

(72) Inventors: Regina Ragan, Irvine, CA (US); Filippo Capolino, Irvine, CA (US); William Thrift, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 527 days.

(21) Appl. No.: 16/112,608

(22) Filed: Aug. 24, 2018

(65) Prior Publication Data
US 2019/0064074 A1   Feb. 28, 2019

Related U.S. Application Data

(60) Provisional application No. 62/549,903, filed on Aug. 24, 2017.

(51) Int. Cl.
| | | |
|---|---|---|
| *G01N 21/65* | (2006.01) |
| *B01L 3/00* | (2006.01) |
| *G06N 20/00* | (2019.01) |
| *C12Q 1/04* | (2006.01) |
| *C25D 13/22* | (2006.01) |
| *C25D 13/02* | (2006.01) |
| *C25D 13/04* | (2006.01) |

(52) U.S. Cl.
CPC ...... *G01N 21/658* (2013.01); *B01L 3/502715* (2013.01); *C12Q 1/04* (2013.01); *C25D 13/02* (2013.01); *C25D 13/22* (2013.01); *G06N 20/00* (2019.01); *B01L 2300/0663* (2013.01); *C25D 13/04* (2013.01)

(58) Field of Classification Search
CPC ...... G01N 21/658; G01N 15/06; G01N 33/00; G01N 33/48; G01N 27/00; C25D 13/02; C25D 13/04; C25D 13/22; C12Q 1/04; B01L 2300/0663
See application file for complete search history.

(56) References Cited

U.S. PATENT DOCUMENTS

2007/0048746 A1    3/2007  Su et al.

FOREIGN PATENT DOCUMENTS

WO         2018206389 A1    11/2018

OTHER PUBLICATIONS

Qi et al., "A Highly Sensitive SERS Sensor for Quantitative Analysis of Glucose Based on the Chemical Etching of Silver Nanoparticles", Journal of Optics, Oct. 23, 2015, vol. 17, 114020, pp. 1-7.

(Continued)

*Primary Examiner* — Brian J. Sines
(74) *Attorney, Agent, or Firm* — KPPB LLP

(57) ABSTRACT

Nanoarchitectures comprised of subwavelength metal nanosphere oligomers with uniform narrow gap spacings for plasmonic and metamaterial devices are described, as well as methods of fabrication thereof, a biosensor system based thereon, and methods of detection of pathogenic or other organisms (e.g., bacteria) using the same.

16 Claims, 31 Drawing Sheets

(56) References Cited

OTHER PUBLICATIONS

Qian et al., "Stimuli-Responsive SERS Nanoparticles: Conformational Control of Plasmonic Coupling and Surface Raman Enhancement", Journal of the American Chemical Society Communications, May 19, 2009, vol. 131, No. 22, pp. 7540-7541, doi: 10.1021/ja902226z.
Rahmani et al., "Subgroup Decomposition of Plasmonic Resonances in Hybrid Oligomers: Modeling the Resonance Lineshape", Nano Letters, Mar. 26, 2012, vol. 12, pp. 2101-2106.
Rahme et al., "Common Virulence Factors for Bacterial Pathogenicity in Plants and Animals", Science, Jun. 30, 1995, vol. 268, pp. 1899-1902.
Rappe et al., "UFF, a Full Periodic Table Force Field for Molecular Mechanics and Molecular Dynamics Simulations", Journal of the American Chemical Society, Dec. 1992, vol. 114, No. 25, pp. 10024-10035, doi: 10.1021/ja00051a040.
Reszka et al., "Oxidation of Pyocyanin, a Cytotoxic Product from Pseudomonas Aeruginosa, by Microperoxidase 11 and Hydrogen Peroxide", Free Radical Biology and Medicine, Jun. 1, 2004, vol. 36, No. 11, pp. 1448-1459, doi: 10.1016/j.freeradbiomed.2004.03.011, available online Apr. 2, 2004.
Ristenpart et al., "Electrohydrodynamic Flow and Colloidal Patterning near Inhomogeneities on Electrodes", Langmuir, Oct. 2, 2008, vol. 24, No. 21, pp. 12172-12180, doi: 10.1021/la801419k.
Saikin et al., "On the chemical bonding effects in the Raman response: Benzenethiol adsorbed on silver clusters", Physical Chemistry Chemical Physics, Aug. 26, 2009, vol. 11, pp. 9401-9411, doi: 10.1039/b906885f.
Saini et al., "Influence of Electrolyte Concentration on the Aggregation of Colloidal Particles near Electrodes in Oscillatory Fields", Langmuir, Apr. 7, 2016, vol. 32, pp. 4210-4216, doi: 10.1021/acs.langmuir.5b04636.
Saito et al., "Vibrational Spectra and Structure of Acetylurea in the Crystalline State", Spectrochimica Acta, Dec. 1979, vol. 35A, pp. 369-375, doi: 10.1016/0584-8539(79)80194-4.
Sam et al., "Semiquantitative Study of the EDC/NHS Activation of Acid Terminal Groups at Modified Porous Silicon Surfaces", Langmuir, 2010, First Published Sep. 2, 2009, vol. 26, No. 2, pp. 809-814, doi: 10.1021/la902220a.
Sardar et al., "Versatile Solid Phase Synthesis of Gold Nanoparticle Dimers Using an Asymmetric Functionalization Approach", Journal of the American Chemical Society Communications, Apr. 11, 2007, vol. 129, No. 17, pp. 5356-5357, doi: 10.1021/ja070933w.
Serra et al., "Chronic Wound Infections: The Role of Pseudomonas Aeruginosa and *Staphylococcus aureus*", Expert Review of Anti-infective Therapy, Mar. 8, 2015, vol. 13, No. 5, pp. 605-613, doi: 10.1586/14787210.2015.1023291.
Sides, "Electrohydrodynamic Particle Aggregation on an Electrode Driven by an Alternating Electric Field Normal to It", Langmuir, Aug. 15, 2001, vol. 17, No. 19, pp. 5791-5800, doi: 10.1021/la0105376.
Sigle et al., "Observing Single Molecules Complexing with Cucurbit[7]uril through Nanogap Surface-Enhanced Raman Spectroscopy", Journal of Physical Chemistry Letters, Jan. 14, 2016, vol. 7, pp. 704-710, doi: 10.1021/acs.jpclett.5b02535.
Solomentsev et al., "Aggregation Dynamics for Two Particles during Electrophoretic Deposition under Steady Fields", Langmuir, Nov. 3, 2000, vol. 16, No. 24, pp. 9208-9216, doi: 10.1021/la0005199.
Squires et al., "Induced-charge electro-osmosis", Journal of Fluid Mechanics, Jun. 25, 2004, vol. 509, pp. 217-252, doi: 10.1017/S0022112004009309.
Sreeprasad et al., "Reversible Assembly and Disassembly of Gold Nanorods Induced by EDTA and Its Application in SERS Tuning", Langmuir, Mar. 2, 2011, vol. 27, pp. 3381-3390, doi: 10.1021/la104828e.
Srichan et al., "Highly-Sensitive Surface-Enhanced Raman Spectroscopy (SERS)-Based Chemical Sensor Using 3D Graphene Foam Decorated with Silver Nanoparticles as SERS Substrate", Scientific Reports, Mar. 29, 2016, vol. 6, No. 23733, pp. 1-9, doi: 10.1038/srep23733.
Stevenson et al., "Quantitative SERRS Immunoassay for the Detection of Human PSA", Analyst, Mar. 17, 2009, vol. 134, pp. 842-844, doi: 10.1039/b902174d.
Taylor et al., "Precise Subnanometer Plasmonic Junctions for SERS within Gold Nanoparticle Assemblies Using Cucurbit[n]uril "Glue"", ACS Nano, Apr. 13, 2011, vol. 5, No. 5, pp. 3878-3887, doi: 10.1021/nn200250v.
Tersoff, "Empirical Interatomic Potential for Carbon, with Applications to Amorphous Carbon", Physical Review Letters, Dec. 19, 1988, vol. 61, No. 25, pp. 2879-2882, doi: 10.1103/PhysRevLett.61.2879.
Thacker et al., "DNA origami based assembly of gold nanoparticle dimers for surface-enhanced Raman scattering", Nature Communications, Mar. 13, 2014, vol. 5, No. 3448, pp. 1-7, doi: 10.1038/ncomms4448.
Theis et al., "Symbiotic Bacteria Appear to Mediate Hyena Social Odors", PNAS, Dec. 3, 2013, vol. 110, No. 49, pp. 19832-19837, doi: 10.1073/pnas.1306477110.
Thrift et al., "Driving Chemical Reactions in Plasmonic Nanogaps with Electrohydrodynamic Flow", ACS Nano, Oct. 20, 2017, vol. 11, pp. 11317-11329, doi: 10.1021/acsnano.7b05815.
Thrift et al., "Surface enhanced Raman scattering for detection of Pseudomonas aeruginosa quorum sensing compounds", Proceedings of SPIE, Biosensing and Nanomedicine, Aug. 31, 2015, vol. VIII, pp. 95500B-1-95500B-13.
Trau et al., "Assembly of Colloidal Crystals at Electrode Interfaces", Langmuir, Nov. 26, 1997, vol. 13, No. 24, pp. 6375-6381, doi: 10.1021/la970568u.
Van Duin et al., "ReaxFF: A Reactive Force Field for Hydrocarbons", Journal of Physical Chemistry A, Sep. 22, 2001, vol. 105, No. 41, pp. 9396-9409, doi: 10.1021/jp004368u.
Van Haute et al., "Controlled Assembly of Biocompatible Metallic Nanoaggregates Using a Small Molecule Crosslinker", Advanced Materials, Jul. 24, 2015, vol. 27, No. 35, pp. 5158-5164, doi: 10.1002/adma.201501602.
Vogel et al., "Advances in Colloidal Assembly: The Design of Structure and Hierarchy in Two and Three Dimensions", Chemical Reviews, Jun. 22, 2015, vol. 115, pp. 6265-6311, doi: 10.1021/cr400081d.
Wang et al., "An optoelectrokinetic technique for programmable particle manipulation and bead-based biosignal enhancement", Lab on a Chip, Aug. 11, 2014, vol. 14, pp. 3958-3967, doi: 10.1039/c4lc00661e.
Wang et al., "Different EDC/NHS Activation Mechanisms between PAA and PMAA Brushes and the Following Amidation Reactions", Langmuir, Aug. 19, 2011m vol. 27, pp. 12058-12068.
Wang et al., "Experimental Observation of Giant Chiroptical Amplification of Small Chiral Molecules by Gold Nanosphere Clusters", Journal of Physical Chemistry C, Apr. 14, 2014, vol. 118, pp. 9690-9695, doi: 10.1021/jp5025813.
Wang et al., "Programming Self-Assembly of DNA Origami Honeycomb Two-Dimensional Lattices and Plasmonic Metamaterials", JACS, May 25, 2016, vol. 138, No. 24, pp. 7733-7740, doi:10.1021/jacs.6b03966.
Watson et al., "Purification and Structural Analysis of Pyocyanin and 1-Hydroxyphenazine", European Journal of Biochemistry, Sep. 1, 1986, vol. 159, pp. 309-313, doi: 10.1111/j.1432-1033.1986.tb09869.x.
Whiteson et al., "Breath Gas Metabolites and Bacterial Metagenomes from Cystic Fibrosis Airways Indicate Active pH Neutral 2,3-Butanedione Fermentation", The ISME Journal, Jan. 9, 2014, vol. 8, pp. 1247-1258, doi: 10.1038/ismej.2013.229.
Woehl et al., "Electrolyte-Dependent Aggregation of Colloidal Particles Near Electrodes in Oscillatory Electric Fields", Langmuir, Apr. 7, 2014, vol. 30, pp. 4887-4894, doi: 10.1021/la4048243.
Work et al., "Characterization of 2D colloids assembled by optically-induced electrohydrodynamics", Soft Matter, 2015, vol. 11, pp. 4266-4272, doi: 10.1039/c5sm00184f.
Wu et al., "Acetic Anhydride in the Gas Phase, Studied by Electron Diffraction and Infrared Spectroscopy, Supplemented With ab Initio

(56) References Cited

OTHER PUBLICATIONS

Calculations of Geometries and Force Fields", Journal of Physical Chemistry A, Jan. 29, 2000, vol. 104, No. 7, pp. 1576-1587, doi: 10.1021/jp993131z.

Wu et al., "Culture-Free Diagnostics of Pseudomonas Aeruginosa Infection by Silver Nanorod Array Based SERS from Clinical Sputum Samples", Nanomedicine: Nanotechnology, Biology and Medicine, Nov. 2014, vol. 10, pp. 1863-1870, doi: 10.1016/j.nano.2014.04.010.

Wu et al., "Differentiation and classification of bacteria using vancomycin functionalized silver nanorods array based surface-enhanced Raman spectroscopy and chemometric analysis", Talanta, Jul. 1, 2015, vol. 139, pp. 96-103, doi: 10.1016/j.talanta.2015.02.045, available online Mar. 4, 2015.

Yan et al., "EDC/NHS activation mechanism of polymethacrylic acid: anhydride versus NHS-ester", RSC Advances, Aug. 3, 2015, vol. 5, pp. 69939-69947, doi: 10.1039/c5ra13844b.

Yang et al., "Mechanistic investigation into the spontaneous linear assembly of gold nanospheres", Physical Chemistry Chemical Physics, Jul. 27, 2010, vol. 12, pp. 11850-11860, doi: 10.1039/c0cp00127a.

Yap et al., "Nanoparticle Cluster Arrays for High-Performance SERS through Directed Self-Assembly on Flat Substrates and on Optical Fibers", ACS Nano, Feb. 14, 2012, vol. 6, No. 3, pp. 2056-2070, doi: 10.1021/nn203661n.

Ye et al., "Gravity-Assisted Convective Assembly of Centimeter-Sized Uniform Two-Dimensional Colloidal Crystals", Langmuir, Jan. 17, 2013, vol. 29, pp. 1796-1801, doi: 10.1021/la3040227.

Ye et al., "Plasmonic Nanoclusters: Near Field Properties of the Fano Resonance Interrogated with SERS", Nano Letters, Feb. 16, 2012, vol. 12, pp. 1660-1667, doi: 10.1021/nl3000453.

Yilmaz et al., "Three-Dimensional Crystalline and Homogeneous Metallic Nanostructures Using Directed Assembly of Nanoparticles", ACS Nano, Apr. 16, 2014, vol. 8, No. 5, pp. 4547-4558, doi: 10.1021/nn500084g.

Yu et al., "Differences between Human Plasma and Serum Metabolite Profiles", PLOS ONE, Jul. 8, 2011, vol. 6, Issue 7, No. e21230, pp. 1-6, doi: 10.1371/journal.pone.0021230.

Zhang et al., "Coherent Fano resonances in a plasmonic nanocluster enhance optical four-wave mixing", PNAS, Jun. 4, 2013, vol. 110, No. 23, pp. 9215-9219, doi:10.1073/pnas.1220304110.

Zhang et al., "Light-Triggered Reversible Self-Assembly of Gold Nanoparticle Oligomers for Tunable SERS", Langmuir, Dec. 25, 2014, vol. 31, pp. 1164-1171, doi: 10.1021/la504365b.

Zhao et al., "Shell-Engineered Chiroplasmonic Assemblies of Nanoparticles for Zeptomolar DNA Detection", Nano Letters, May 23, 2014, vol. 14, pp. 3908-3913, doi: 10.1021/nl501166m.

Zhu et al., "Quantum mechanical limit to plasmonic enhancement as observed by surface-enhanced Raman scattering", Nature Communications, Oct. 14, 2014, vol. 5, No. 5228, pp. 1-8.

Zhu et al., "Thermosensitive Gold Nanoparticles", JACS Communications, Feb. 11, 2004, vol. 126, No. 9, pp. 2656-2657, doi: 10.1021/ja038544z.

Zon et al., "Preparation of gold nanoparticle dimers via streptavidin-induced interlinking", Journal of Nanoparticle Research, Sep. 24, 2013, vol. 15, No. 1974, pp. 1-10.

Zrimsek et al., "Single Molecule Surface-Enhanced Raman Spectroscopy: A Critical Analysis of the Bianalyte versus Isotopologue Proof", Journal of Physical Chemistry C, Feb. 11, 2016, vol. 120, pp. 5133-5142, doi: 10.1021/acs.jpcc.6b00606.

Żukovskaja et al., "Detection of Pseudomonas aeruginosa Metabolite Pyocyanin in Water and Saliva by Employing the SERS Technique", Sensors, Jul. 25, 2017, vol. 17, No. 8, 1704, pp. 1-11, doi: 10.3390/s17081704.

Li et al., "Noninvasive liver diseases detection based on serum surface enhanced Raman spectroscopy and statistical analysis", Optics Express, Jul. 13, 2015, vol. 23, Issue 14, pp. 18361-18372, https://doi.org/10.1364/OE.23.018361.

Li et al., "Surface Enhanced Raman Scattering Detection of Cancer Biomarkers with Bifunctional Nanocomposite Probes", Analytical Chemistry, Oct. 19, 2015, vol. 87, No. 21, pp. 10698-10702, https://doi.org/10.1021/acs.analchem.5b03456.

Liu et al., "Rapid bacterial antibiotic susceptibility test based on simple surface-enhanced Raman spectroscopic biomarkers", Scientific Reports, Mar. 21, 2016, vol. 6, No. 23375, 15 pgs., DOI: 10.1038/srep23375.

Liu et al., F.T., "Isolation Forests", 2008 Eighth IEEE International Conference on Data Mining, Dec. 15-19, 2008, Pisa, Italy, pp. 413-422, DOI: 10.1109/ICDM.2008.17.

Lobritz et al., "Antibiotic efficacy is linked to bacterial cellular respiration", PNAS, Jul. 7, 2015, vol. 112, No. 27, pp. 8173-8180; first published Jun. 22, 2015; https://doi.org/10.1073/pnas.1509743112.

Lussier et al., "Machine-Learning-Driven Surface-Enhanced Raman Scattering Optophysiology Reveals Multiplexed Metabolite Gradients Near Cells", ACS Nano, Feb. 11, 2019, vol. 13, No. 2, pp. 1403-1411, doi: 10.1021/acsnano.8b07024.

Marston et al., "Antimicrobial Resistance", Journal of the American Medical Association, Sep. 20, 2016, vol. 316, No. 11, pp. 1193-1204, doi:10.1001/jama.2016.11764.

Nguyen et al., "Longitudinal Monitoring of Biofilm Formation via Robust Surface-Enhanced Raman Scattering Quantification of Pseudomonas aeruginosa-Produced Metabolites", ACS Applied Materials and Interfaces, Mar. 28, 2018. vol. 10, No. 15, pp. 12364-12373, https://doi.org/10.1021/acsami.7b18592.

Nijhuis et al., "Comparison of ePlex Respiratory Pathogen Panel with Laboratory-Developed Real-Time PCR Assays for Detection of Respiratory Pathogens", Journal of Clinical Microbiology, Jun. 2017, vol. 55. No. 6, pp. 1938-1945, published online May 23, 2017, pre-published online Apr. 12, 2017. doi: 10.1128/JCM.00221-17.

O'Neill, "Tackling Drug-Resistant Injections Globally: Final Report and Recommendations, The Review on Antimicrobial Resistance", Review on Antimicrobial Resistance, May 2016, 84 pgs.

Pan et al., "A Survey on Transfer Learning", IEEE Transactions on Knowledge and Data Engineering, vol. 22, No. 10, Oct. 2010, pp. 1345-1359, DOI: 10.1109/TKDE.2009.191.

Pang et al., "Review of surface enhanced Raman spectroscopic (SERS) detection of synthetic chemical pesticides", TrAC Trends in Analytical Chemistry, Dec. 2016, vol. 85, Part A, pp. 73-82, https://doi.org/10.1016/j.trac.2016.06.017.

Pozzi et al., "SERS Discrimination of Closely Related Molecules: A Systematic Study of Natural Red Dyes in Binary Mixtures", Journal of Physical Chemistry C, Jun. 13, 2016, vol. 120, pp. 21017-21026, DOI: 10.1021/acs.jpcc.6b03317.

Premarisi et al., "Rapid urinary tract infection diagnostics by surface-enhanced Raman spectroscopy (SERS): identification and antibiotic susceptibilities", Analytical and Bioanalytical Chemistry, Feb. 24, 2017, vol. 409, pp. 3043-3054, https://doi.org/10.1007/s00216-017-0244-7.

Pulido et al., "Progress on the development of rapid methods for antimicrobial susceptibility testing", Journal of Antimicrobial Chemotherapy, Dec. 2013, vol. 68, Issue 12, pp. 2710-2717, published Jun. 30, 2013, https://doi.org/10.1093/jac/dkt253.

Rajkomar et al., "Scalable and accurate deep learning with electronic health records", Digital Medicine, 2018, No. 1, No. 18, 10 pgs., published online May 9, 2018, doi:10.1038/s41746-018-0029-1.

Reller et al., "Antimicrobial Susceptibility Testing: A Review of General Principles and Contemporary Practices", Clinical Infectious Diseases, Medical Microbiology, CID2009:49, Dec. 1, 2009, vol. 49, pp. 1749-1755, DOI: 10.1086/647952.

Roberts et al., "Bayesian Approaches to Gaussian Mixture Modeling", IEEE Transactions on Pattern Analysis and Machine Intelligence, Nov. 1998, vol. 20, No. 11, pp. 1133-1142, https://doi.org/10.1109/34.730550.

Rochford et al., "Global governance of antimicrobial resistance", The Lancet, May 19, 2018, vol. 391, Issue 10134, pp. 1976-1978, https://doi.org/10.1016/S0140-6736(18)31117-6.

Rowan et al., "Bactericidal antibiotics induce programmed metabolic toxicity", Microbial Cell, Sep. 3, 2016, vol. 3, No. 4, pp. 178-180; doi: 10.15698/mic2016.04.493.

(56) References Cited

OTHER PUBLICATIONS

Savitzky et al., "Smoothing and Differentiation of Data by Simplified Least Squares Procedures", Analytical Chemistry, Jul. 1964, vol. 36, No. 8, pp. 1627-1639, https://doi.org/10.1021/ac60214a047.
Schoepp et al., "Rapid pathogen-specific phenotypic antibiotic susceptibility testing using digital LAMP quantification in clinical samples", Science Translational Medicine, Oct. 4, 2017, vol. 9, No., eaal3693, pp. 1-12, doi: 10.1126/scitranslmed.aal3693.
Shi et al., "Setting Up a Surface-Enhanced Raman Scattering Database for Artificial-Intelligence-Based Label-Free Discrimination of Tumor Suppressor Genes", Anal. Chem. Nov. 20, 2018, 2018, vol. 90, No. 24, pp. 14216-14221, https://doi.org/10.1021/acs.analchem.8b03080.
Steingart et al., "Xpert® MTB/RIF assay for pulmonary tuberculosis and rifampicin resistance in adults", Cochrane Database System Reviews, Jan. 31, 2013 vol. 1:CD009593, doi: 10.1002/14651858.CD009593.pub2.
Sugden et al., "Combatting antimicrobial resistance globally", Nature Microbiology, Oct. 2016, vol. 1, No. 10, 2 pgs. Sep. 27, 2016, doi: 10.1038/nmicrobiol.2016.187.
Thrift et al., "Quantification of Analyte Concentration in the Single Molecule Regime Using Convolutional Neural Networks", Analytical Chemistry, Oct. 7, 2019, vol. 91, No. 21, pp. 13337-13342, https://doi.org/10.1021/acs.analchem.9b03599.
Thrift et al., "Surface-Enhanced Raman Scattering-Based Odor Compass: Locating Multiple Chemical Sources and Pathogens", ACS Sens., Aug. 16, 2019, vol. 4, No. 9, pp. 2311-2319, https://doi.org/10.1021/acssensors.9b00809.
Van Belkum et al., "Developmental roadmap for antimicrobial susceptibility testing systems", Nature Reviews | Microbiology, 2019, vol. 17, No. 1, 12 pgs., https://doi.org/10.1038/s41579-018-0098-0.
Van Belkum et al., "Next-generation antimicrobial susceptibility testing", Journal of Clinical Microbiology, Jul. 2013, vol. 51, No. 7, pp. 2018-2024, epublished Mar. 24, 2013, doi: 10.1128/JCM.00313-13.
Wimmer et al., "Strategy for rapid identification and antibiotic susceptibility testing of gram-negative bacteria directly recovered from positive blood cultures using the Bruker MALDI Biotyper and the BD Phoenix system", Journal of Clinical Microbiology, Jul. 2012, vol. 50, No. 7, pp. 2452-2454, epublished Apr. 12, 2012, doi: 10.1128/JCM.00409-12.
Abad et al., "Functionalization of Thioctic Acid-Capped Gold Nanoparticles for Specific Immobilization of Histidine-Tagged Proteins", Journal of the American Chemical Society, Mar. 19, 2005, vol. 127, No. 15, pp. 5689-5694, doi: 10.1021/ja042717i.
Adams et al., "Directing Cluster Formation of Au Nanoparticles from Colloidal Solution", Langmuir, Mar. 8, 2013, vol. 29, No. 13, pp. 4242-4251, doi: 10.1021/la3051719.
Adams et al., "Non-lithographic SERS Substrates: Tailoring Surface Chemistry for Au Nanoparticle Cluster Assembly", Small, Apr. 23, 2012, vol. 8, No. 14, pp. 2239-2249, doi: 10.1002/smll.201102708.
Aggarwal et al., "Measurement of the absolute Raman scattering cross section of the 1584-cm-1 band of benzenethiol and the surface-enhanced Raman scattering cross section enhancement factor for femtosecond laser-nanostructured substrates", Journal of Raman Spectroscopy, Aug. 14, 2009, vol. 40, No. 9, pp. 1331-1333, doi: 10.1002/jrs.2396.
Akselrod et al., "Large-Area Metasurface Perfect Absorbers from Visible to Near-Infrared", Advanced Materials, Nov. 9, 2015, vol. 27, pp. 8028-8034, doi: 10.1002/adma.201503281.
Aksenov et al., "Global Chemical Analysis of Biology by Mass Spectrometry", Nature Reviews: Chemistry, Jul. 5, 2017, vol. 1, Article 0054, pp. 1-20, doi: 10.1038/s41570-017-0054.
Alù et al., "Dynamical theory of artificial optical magnetism produced by rings of plasmonic nanoparticles", Physical Review B, Aug. 11, 2008, vol. 78, No. 8, pp. 085112-1-085112-10.

Anderson et al., "Innate and Induced Resistance Mechanisms of Bacterial Biofilms", Bacterial Biofilms; Current Topics in Microbiology and Immunology, Springer: Berlin, Heidelberg, 2008, pp. 85-105.
Armbruster et al., "Limit of Blank, Limit of Detection and Limit of Quantitation", Clinical Biochemist Reviews, Aug. 2008, vol. 29, Supp (I), pp. S49-S52.
Bartczak et al., "Preparation of Peptide-Functionalized Gold Nanoparticles Using One Pot EDC/Sulfo-NHS Coupling", Langmuir, 2011, vol. 27, pp. 10119-10123.
Bell et al., "Monitoring Anhydride and Acid Conversion in Supercritical/Hydrothermal Water by in Situ Fiber-Optic Raman Spectroscopy", Analytical Chemistry, Jan. 15, 1998, vol. 70, No. 2, pp. 332-339, doi: 10.1021/ac9707141.
Berry et al., "Tracking heavy water (D2O) incorporation for identifying and sorting active microbial cells", PNAS, Jan. 13, 2015, vol. 112, No. 2, pp. E194-E203, doi: 10.1073/pnas.1420406112, published online Dec. 30, 2014.
Bertie et al., "The Raman Spectrum of Gaseous Acetic Acid at 21° C", Journal of Chemical Physics, Aug. 1982, vol. 77, No. 11, pp. 5267-5271, doi: doi.org/10.1063/1.443795.
Bhattacharjee et al., "Effects of Growth Surface Topography on Bacterial Signaling in Coculture Biofilms", ACS Applied Materials & Interfaces, May 9, 2017, vol. 9, No. 22, pp. 18531-18539, doi: 10.1021/acsami.7b04223.
Biswas et al., "Nonlinear Chiro-Optical Amplification by Plasmonic Nanolens Arrays Formed via Directed Assembly of Gold Nanoparticles", Nano Letters, Feb. 3, 2015, vol. 15, No. 3, pp. 1836-1842, doi: 10.1021/nl504613q.
Bodelón et al., "Detection and imaging of quorum sensing in Pseudomonas aeruginosa biofilm communities by surface-enhanced resonance Raman scattering", Nature Materials, Aug. 8, 2016, vol. 15, No. 11, pp. 1203-1211, doi: 10.1038/nmat4720.
Böhmer, "In Situ Observation of 2-Dimensional Clustering during Electrophoretic Deposition", Langmuir, Nov. 27, 2006, vol. 12, No. 24, pp. 5747-5750, doi: 10.1021/la960183w.
Booth et al., "In-Depth Electrochemical Investigation of Surface Attachment Chemistry via Carbodiimide Coupling", Langmuir, Jun. 24, 2015, vol. 31, 8033-8041.
Bowden et al., "Harmonizing Lipidomics: NIST Interlaboratory Comparison Exercise for Lipidomics Using Standard Reference Material 1950 Metabolites in Frozen Human Plasma", Journal of Lipid Research, Oct. 6, 2017, vol. 58, No. 12, doi: 2275-2288, 10.1194/jlr.M079012.
Brenner, "Empirical Potential for Hydrocarbons for Use in Simulating the Chemical Vapor Deposition of Diamond Films", Physical Review B: Condensed Matter and Materials Physics, Nov. 15, 1990, vol. 42, No. 15, pp. 9458-9471, doi: 10.1103/PhysRevB.42.9458.
Cai et al., "Investigation of surface-enhanced Raman scattering from platinum electrodes using a confocal Raman microscope: dependence of surface roughening pretreatment", Surface Science, May 31, 1998, vol. 406, Nos. 1-3, pp. 9-22.
Caldwell et al., "Plasmonic Nanopillar Arrays for Large-Area, High-Enhancement Surface-Enhanced Raman Scattering Sensors", ACS Nano, Apr. 11, 2011, vol. 5, No. 5, pp. 4046-4055, doi: 10.1021/nn200636t.
Campione et al., "Comparison of electric field enhancements: Linear and triangular oligomers versus hexagonal arrays of plasmonic nanospheres", Optics Express, Mar. 26, 2013, vol. 21, No. 7, pp. 7957-7973, doi: 10.1364/oe.21.007957.
Campione et al., "Enhanced Magnetic and Electric Fields via Fano Resonances in Metasurfaces of Circular Clusters of Plasmonic Nanoparticles", ACS Photonics, Feb. 7, 2014, vol. 1, pp. 254-260, doi: 10.1021/ph4001313.
Campione et al., "Fano resonances in metasurfaces made of linear trimers of plasmonic nanoparticles", Optics Letters, Dec. 15, 2013, vol. 38, No. 24, pp. 5216-5219.
Chen et al., "Large-Area Nanoimprinted Colloidal Au Nanocrystal-Based Nanoantennas for Ultrathin Polarizing Plasmonic Metasurfaces", Nano Letters, Jul. 10, 2015, vol. 15, No. 8, pp. 5254-5260, doi: 10.1021/acs.nanolett.5b02647.
Cheung et al., "Quantitative Analysis of the Banned Food Dye Sudan-1 Using Surface Enhanced Raman Scattering with Multi-

(56) References Cited

OTHER PUBLICATIONS variate Chemometrics", Journal of Physical Chemistry C, Feb. 3, 2010, vol. 114, No. 16, pp. 7285-7290, doi: 10.1021/jp908892n.
Chikkaraddy et al., "Single-molecule strong coupling at room temperature in plasmonic nanocavities", Nature, Jul. 7, 2016, vol. 535, pp. 127-130.
Choi et al., "Design of a versatile chemical assembly method for patterning colloidal nanoparticles", Nanotechnology, Jan. 14, 2009, vol. 20, No. 6, 065301, 6 pgs.
Darvishzadeh-Varcheie et al., "Electric field enhancement with plasmonic colloidal nanoantennas excited by a silicon nitride waveguide", Optics Express, Dec. 12, 2016, vol. 24, No. 25, pp. 28337-28352, doi: 10.1364/OE.24.028337, first published Nov. 29, 2016.
Davies, "Pseudomonas Aeruginosa in Cystic Fibrosis: Pathogenesis and Persistence", Paediatric Respiratory Reviews, Jul. 2002, vol. 3, No. 2, pp. 128-134, doi: 10.1016/51526-0550(02)00003-3.
De Kievit et al., "Quorum-Sensing Genes in Pseudomonas Aeruginosa Biofilms: Their Role and Expression Patterns", Applied and Environmental Microbiology, Apr. 2001, vol. 67, No. 4, pp. 1865-1873, doi: 10.1128/AEM.67.4.1865-1873.2001.
Dietrich et al., "The Phenazine Pyocyanin Is a Terminal Signalling Factor in the Quorum Sensing Network of Pseudomonas Aeruginosa", Molecular Microbiology, Jul. 25, 2006, vol. 61, No. 5, pp. 1308-1321, doi: 10.1111/j.1365-2958.2006.05306.x.
Dong et al., "Detection and Direct Readout of Drugs in Human Urine Using Dynamic Surface-Enhanced Raman Spectroscopy and Support Vector Machines", Analytical Chemistry, Jan. 29, 2015, vol. 87, No. 5, pp. 2937-2944, doi: 10.1021/acs.analchem.5b00137.
Eggleston et al., "Optical antenna enhanced spontaneous emission", PNAS, Feb. 10, 2015, vol. 112, No. 6, pp. 1704-1709, doi: 10.1073/pnas.1423294112.
Fan et al., "Plasmonic Mode Engineering with Templated Self-Assembled Nanoclusters", Nano Letters, Sep. 4, 2012, vol. 12, No. 10, pp. 5318-5324, doi: 10.1021/nl302650t.
Fessenden, "Metabolomics: Small Molecules, Single Cells", Nature, Dec. 1, 2016, vol. 540, pp. 153-156, doi: 10.1038/540153a.
Flauraud et al., "Nanoscale topographical control of capillary assembly of nanoparticles", Nature Nanotechnology, Jan. 2017, published online Oct. 3, 2016, vol. 12, pp. 73-80.
Fleck et al., "Convective Assembly of a Particle Monolayer", Langmuir, Nov. 23, 2015, vol. 31, No. 51, pp. 13655-13663, doi: 10.1021/acs.langmuir.5b03635.
Fleischmann et al., "Raman spectra of pyridine adsorbed at a silver electrode", Chemical Physics Letters, May 15, 1974, vol. 26, No. 2, pp. 163-166.
Frenkel et al., "Understanding Molecular Simulation From Algorithms to Applications", Academic Press, Second edition, 658 pgs. San Diego, 2001, (presented in two parts).
Gaulding et al., "Deposition of Wafer-Scale Single-Component and Binary Nanocrystal Superlattice Thin Films Via Dip-Coating", Advanced Materials, Mar. 27, 2015, vol. 27, pp. 2846-2851, doi: 10.1002/adma.201405575.
Geladi et al., "Partial Least-Squares Regression: A Tutorial", Analytical Chemica Acta, 1986, vol. 185, pp. 1-17, doi: 10.1016/0003-2670(86)80028-9.
Ghebremedhin et al., "Accurate and Rapid Differentiation of Acinetobacter baumannii Strains by Raman Spectroscopy: a Comparative Study", Journal of Clinical Microbiology, Aug. 2017, First Published Jun. 7, 2017, vol. 55, No. 8, pp. 2480-2490, doi: 10.1128/JCM.01744-16.
Gong et al., "Shape-dependent ordering of gold nanocrystals into large-scale superlattices", Nature Communications, Jan. 19, 2017, vol. 8, No. 14038, pp. 1-9.
Gonidec et al., "Fabrication of Nonperiodic Metasurfaces by Microlens Projection Lithography", Nano Letters, May 31, 2016, vol. 16, pp. 4125-4132, doi:10.1021/acs.nanolett.6b00952.
Grady et al., "Influence of dielectric function properties on the optical response of plasmon resonant metallic nanoparticles", Chemical Physics Letters, Nov. 21, 2004, vol. 399, pp. 167-171, doi: 10.1016/j.cplett.2004.09.154, published online Oct. 22, 2004.
Greybush et al., "Plasmon-Enhanced Upconversion Luminescence in Single Nanophosphor—Nanorod Heterodimers Formed through Template-Assisted Self-Assembly", ACS Nano, Sep. 2, 2014, vol. 8, No. 9, pp. 9482-9491, doi: 10.1021/nn503675a.
Grubisha et al., "Femtomolar Detection of Prostate-Specific Antigen: An Immunoassay Based on Surface-Enhanced Raman Scattering and Immunogold Labels", Analytical Chemistry, Sep. 23, 2003, vol. 75, No. 21, pp. 5936-5943, doi: 10.1021/ac034356f.
Gür et al., "Toward Self-Assembled Plasmonic Devices: High-Yield Arrangement of Gold Nanoparticles on DNA Origami Templates", ACS Nano, May 9, 2016, vol. 10, pp. 5374-5382, doi: 10.1021/acsnano.6b01537.
Habermehl et al., "Fabrication of SERS Substrates by Roll-to-Roll Hot Embossing", Nano-Optics: Principles Enabling Basic Research and Applications, NATO Science for Peace and Security Series B: Physics and Biophysics, Springer, Dordrecht, Feb. 17, 2017, pp. 513-515, doi: 10.1007/978-94-024-0850-8_55.
Hamon et al., "Hierarchical Assembly of Plasmonic Nanoparticles", Chemistry—A European Journal, Apr. 29, 2015, vol. 21, pp. 9956-9963, doi: 10.1002/chem.201500149.
Hanwell et al., "Avogadro: An Advanced Semantic Chemical Editor, Visualization, and Analysis Platform", Journal of Cheminformatics, Aug. 13, 2012, vol. 4, 17 pgs, doi: 10.1186/1758-2946-4-17.
Henkelman et al., "Improved Tangent Estimate in the Nudged Elastic Band Method for Finding Minimum Energy Paths and Saddle Points", Journal of Chemical Physics, Dec. 8, 2000, vol. 113, No. 22, pp. 9978-9985, doi: 10.1063/1.1323224.
Hoang et al., "Ultrafast spontaneous emission source using plasmonic nanoantennas", Nature Communications, Jul. 27, 2015, vol. 6, No. 7788, pp. 1-7.
Hotze et al., "Nanoparticle Aggregation: Challenges to Understanding Transport and Reactivity in the Environment", J. Environ. Qual., Nov. 2010, vol. 39, pp. 1909-1924, published online May 20, 2010.
Hunter et al., "Phenazine Content in the Cystic Fibrosis Respiratory Tract Negatively Correlates with Lung Function and Microbial Complexity", American Journal of Respiratory Cell and Molecular Biology, Aug. 3, 2012, vol. 47, No. 6, pp. 738-745, doi: 10.1165/rcmb.2012-0088OC.
Adams et al., "Directing Cluster Formation of Au Nanoparticles from Colloidal Solution", Langmuir, Mar. 8, 2013, vol. 29, No. 13, pp. 4242-4251, https://doi.org/10.1021/la3051719.
Alharbi, "Simultaneous multiplexed quantification of nicotine and its metabolites using surface enhanced Raman scattering", Analyst, Jul. 2014, vol. 139, pp. 4820-4827, DOI: 10.1039/c4an00879k.
Ardila et al., "End-to-end lung cancer screening with three-dimensional deep learning on low-dose chest computed tomography", Nat. Med., Jun. 2019, vol. 25, No. pp. 954-961, published online May 20, 2019, doi: 10.1038/s41591-019-0447-x.
Ballinger et al., "DeepHeart: Semi-Supervised Sequence Learning for Cardiovascular Risk Prediction", in Thirty-Second AAAI Conference on Artificial Intelligence, 2018, 9 pgs.
Baltekin et al., "Antibiotic susceptibility testing in less than 30 min using direct single-cell imaging", PNAS, Aug. 22, 2017, vol. 114, No. 34, pp. 9170-9175, https://doi.org/10.1073/pnas.1708558114.
Belenky et al., "Bactericidal Antibiotics Induce Toxic Metabolic Perturbations that Lead to Cellular Damage", Cell Reports, Nov. 3, 2015, vol. 13, pp. 968-980, http://dx.doi.org/10.1016/j.celrep.2015.09.059.
Bhattacharjee et al., "Rhamnolipids Mediate an Interspecies Biofilm Dispersal Signaling Pathway", ACS Chem. Biol., Sep. 13, 2016, vol. 11, No. 11, 3068-3076, https://doi.org/10.1021/acschembio.6b00750.
Bodelon et al., "Detection and imaging of quorum sensing in Pseudomonas aeruginosa biofilm communities by surface-enhanced resonance Raman scattering", Nature Materials, Aug. 7, 2016, vol. 15, No. 11, pp. 1203-1211, DOI: 10.1038/nmat4720.
Bos et al., "Volatile Metabolites of Pathogens: A Systematic Review", PLoS Pathogens, May 9, 2013, vol. 9, Issue 5 | e1003311, pp. 1-8, doi: doi:10.1371/journal.ppat.1003311.
Brynildsen et al., "Potentiating antibacterial activity by predictably enhancing endogenous microbial ROS production", NIH Public

(56) References Cited

OTHER PUBLICATIONS

Access, Author Manuscript, published in final form as: Nat Biotechnol., Feb. 2013; vol. 31, No. 2, pp. 160-165, doi:10.1038/nbt.2458.

Burckhardt et al., "Using matrix-assisted laser desorption ionization-time of flight mass spectrometry to detect carbapenem resistance within 1 to 2.5 hours", Journal of Clinical Microbiology, Sep. 2011, vol. 49, No. 9. pp. 3321-3324, published online Jul. 27, 2011, doi: 10.1128/JCM.00287-11.

Caliendo et al., "Point-Counterpoint: The FDA Has a Role in Regulation of Laboratory-Developed Tests", Journal of Clinical Microbiology, Apr. 2016, vol. 54, No. 4, pp. 829-833, doi:10.1128/JCM.00063-16.

Chang et al., "Excessive mechanical loading promotes osteoarthritis through the gremlin-1-NF-κb pathway", Nature Communications, Mar. 29, 2019, vol. 10, No. 1442, doi: 10.1038/s41467-019-09491-5.

Cheng et al., "Computer-Aided Diagnosis with Deep Learning Architecture: Applications to Breast Lesions in US Images and Pulmonary Nodules in CT Scans", Science Reports, Apr. 15, 2016, vol. 6, No. 24454, doi: 10.1038/srep24454.

Chiu et al., "Quantification of biomolecules responsible for biomarkers in the surface-enhanced Raman spectra of bacteria using liquid chromatography-mass spectrometry", Physical Chemistry Chemical Physics, Mar. 2018, vol. 20, No. 12, pp. 8032-8041, Epub Mar. 7, 2018, https://doi.org/10.1039/C7CP07103E.

Cortes et al., "Support-Vector Networks", Machine Leaning, 1995, vol. 20, pp. 273-297.

Dwyer et al., "Unraveling the physiological complexities of antibiotic lethality", Annu. Rev. Pharmacol. Toxicol., 2015, vol. 55. pp. 313-332, published online Sep. 10, 2014, doi: 10.1146/annurev-pharmtox-010814-124712.

Esteva et al, "Dermatologist-level classification of skin cancer with deep neural networks", Nature, Feb. 2, 2017, vol. 542, No. 7639, pp. 115-118, Epub Jan 25, 2017, doi:10.1038/nature21056.

Figueiredo et al., "Identification of the naturally occurring genes encoding carbapenem-hydrolysing oxacillinases from Acinetobacter haemolyticus, Acinetobacter johnsonii, and Acinetobacter calcoaceticus", Clinical Microbiology and Infection, 20112, vol. 18, pp. 907-913, published online Oct. 27, 2011, doi: 10.1111/j.1469-0691.2011.03708.x.

Fleming-Dutra et al., "Prevalence of Inappropriate Antibiotic Prescriptions Among US Ambulatory Care Visits, 2010-2011", Journal of the American Medical Association, May 3, 2016, vol. 315, No. 17, pp. 1864-1873, doi:10.1001/jama.2016.4151.

Galvan et al., "Surface-Enhanced Raman Scattering for Rapid Detection and Characterization of Antibiotic-Resistant Bacteria", Advanced Healthcare Materials, Jul. 2018, vol. 7, No. 13. e1701335. 27 pgs., first published Mar. 5, 2018, doi: 10.1002/adhm.201701335.

Guo et al., "ECMDB: The *E. coli* Metabolome Database", Nucleic Acids Research, 2013, vol. 41, Database issue D625-D630, published online Oct. 29, 2012, doi:10.1093/nar/gks992.

Ho et al., "Rapid identification of pathogenic bacteria using Raman spectroscopy and deep learning", Nature Communications, 2019, vol. 10, No. 4927, pp. 1-8, DOI: 10.1038/s41467-019-12898-9.

Holcomb et al., "Host-Based Peripheral Blood Gene Expression Analysis for Diagnosis of Infectious Diseases", Journal of Clinical Microbiology, Feb. 2017, vol. 55, Issue 2, pp. 360-368. https://doi.org/10.1128/JCM.01057-16.

Hrabak et al., "Carbapenemase activity detection by matrix-assisted laser desorption ionization-time of flight mass spectrometry", Journal of Clinical Microbiology, Sep. 2011, vol. 49. No. 9, pp. 3222-3227, published online Jul. 20, 2011, doi: 10.1128/JCM.00984-11.

Jung et al., "Evaluation of a Semiquantitative Matrix-Assisted Laser Desorption Ionization—Time of Flight Mass Spectrometry Method for Rapid Antimicrobial Susceptibility Testing of Positive Blood Cultures", Journal of Clinical Microbiology, Nov. 2016, vol. 54, No. 11, pp. 2820-2824.

Kingma et al., "Adam: A Method for Stochastic Optimization", arXiv.org, Retrieved from: https://arxiv.org/abs/1412.6980v1 [cs.LG], Dec. 22, 2014, 9 pgs.

Kingma et al., "Auto-Encoding Variational Bayes", arXiv:1312.6114v1 [stat.ML], Dec. 20, 2013, 9 pgs.

Larkin, "Infrared and Raman spectroscopy, principles and spectral interpretation", Elsevier 2011, 275 pgs.

Li et al., "Hierarchical Assembly of Plasmonic Nanoparticle Heterodimer Arrays with Tunable Sub-5 nm Nanogaps", Nano Letters, Jun. 11, 2019, vol. 19, No. 7, pp. 4314-4320, https://doi.org/10.1021/acs.nanolett.9b00792.

Israelachvili, "Intermolecular and Surface Forces", Intermolecular and Surface Forces, Revised Third Edition, (Academic Press, 2011), 706 pgs. (presented in four parts).

Ito et al., "The Vibrational Spectra of the Formate, Acetate, and Oxalate Ions", Canadian Journal of Chemistry, 1956, vol. 34, No. 2, pp. 170-178, doi: doi.org/10.1139/v56-021.

Jaquay et al., "Light-Assisted, Templated Self-Assembly of Gold Nanoparticle Chains", Nano Letters, Aug. 25, 2014, vol. 14, pp. 5184-5188, doi: 10.1021/nl502083m.

Kanipe et al., "Large Format Surface-Enhanced Raman Spectroscopy Substrate Optimized for Enhancement and Uniformity", ACS Nano, Aug. 2, 2016, vol. 10, pp. 7566-7571, doi: 10.1021/acsnano.6b02564.

Kasera et al., "Quantitative multiplexing with nano-self-assemblies in SERS", Scientific Report, Oct. 30, 2014, vol. 4, No. 6785, pp. 1-6.

Keleştemur et al., "Understanding and Discrimination of Biofilms of Clinically Relevant Microorganisms Using Surface-Enhanced Raman Scattering", Applied Spectroscopy, 2017, First Published Oct. 5, 2016, vol. 71, No. 6, pp. 1180-1188, doi: 10.1177/0003702816670916.

Kennemur et al., "Advances in polycarbodiimide chemistry", Polymer, 2011, vol. 52, pp. 1693-1710, available online Mar. 3, 2011.

Kim et al., "Reversible Tuning of SERS Hot Spots with Aptamers", Advanced Materials, Aug. 8, 2011, vol. 23, pp. 4152-4156, doi: 10.1002/adma.201101847.

Kim et al., "Template-assisted self-assembly of diblock copolymer micelles for non-hexagonal arrays of Au nanoparticles", RSC Advances, Apr. 20, 2016, vol. 6, pp. 41331-41339, doi: 10.1039/c6ra05530c.

Klein et al., "Single-slit split-ring resonators at optical frequencies: limits of size scaling", Optics Letters, May 1, 2006, vol. 31, No. 9, pp. 1259-1261, doi: 10.1364/ol.31.001259.

Kneipp et al., "Single Molecule Detection Using Surface-Enhanced Raman Scattering (SERS)", Physical Review Letters, Mar. 3, 1997, vol. 78, No. 9, pp. 1667-1670.

Koh et al., "Electron Energy-Loss Spectroscopy (EELS) of Surface Plasmons in Single Silver Nanoparticles and Dimers: Influence of Beam Damage and Mapping of Dark Modes", ACS Nano, Oct. 27, 2009, vol. 3, No. 10, pp. 3015-3022, doi: 10.1021/nn900922z, published online Sep. 22, 2009.

Kolter et al., "Microbial Sciences: The Superficial Life of Microbes", Nature, May 18, 2006, vol. 441, pp. 300-302.

Le Ru et al., "A Scheme for Detecting Every Single Target Molecule with Surface-Enhanced Raman Spectroscopy", Nano Letters, Oct. 10, 2011, vol. 11, pp. 5013-5019, doi: 10.1021/nl2030344.

Le Ru et al., "Proof of Single-Molecule Sensitivity in Surface Enhanced Raman Scattering (SERS) by Means of a Two-Analyte Technique", Journal of Physical Chemistry B, Jan. 10, 2006, vol. 110, pp. 1944-1948, doi: 10.1021/jp054732v.

Le Ru et al., "Surface Enhanced Raman Scattering Enhancement Factors: A Comprehensive Study", J. Phys. Chem. C, 2007, vol. 111, pp. 13794-13803.

Lee et al., "Quantitative Analysis of Methyl Parathion Pesticides in a Polydimethylsiloxane Microfluidic Channel Using Confocal Surface-Enhanced Raman Spectroscopy", Applied Spectroscopy, Apr. 6, 2006, vol. 60, No. 4, pp. 373-377, doi: 10.1366/000370206776593762.

Lee et al., "Tuning and Maximizing the Single-Molecule Surface-Enhanced Raman Scattering from DNA-Tethered Nanodumbbells", ACS Nano, Oct. 4, 2012, vol. 6, No. 11, pp. 9574-9584, doi: 10.1021/nn3028216.

Li et al., "Dimers of Silver Nanospheres: Facile Synthesis and Their Use as Hot Spots for Surface-Enhanced Raman Scattering", Nano

(56) References Cited

OTHER PUBLICATIONS

Letters, 2009, First Published Dec. 22, 2008, vol. 9, No. 1, pp. 485-490, doi: 10.1021/nl803621x.
Li et al., "Etching and Dimerization: A Simple and Versatile Route to Dimers of Silver Nanospheres with a Range of Sizes", Angewandte Chemie Int. Ed., 2010, First Published Dec. 22, 2009, vol. 49, pp. 164-168, doi: 10.1002/anie.200905245.
Liu et al., "Large-Area 2D Gold Nanorod Arrays Assembled on Block Copolymer Templates", Small, 2013, First Published Oct. 8, 2012, vol. 9, No. 4, pp. 505-510, doi: doi.org/10.1002/smll.201201503.
Liu et al., "Manipulating Magnetic Plasmon Propagation in Metallic Nanocluster Networks", ACS Nano, May 2, 2012, vol. 6, No. 6, pp. 5482-5488, doi: 10.1021/nn301393x.
Lorenz et al., "Cultivation-Free Raman Spectroscopic Investigations of Bacteria", Trends in Microbiology, May 2017, vol. 25, No. 5, pp. 413-424, doi: 10.1016/j.tim.2017.01.002.
Lucas et al., "Development of a Sensitive, Stable and EGFR-Specific Molecular Imaging Agent for Surface Enhanced Raman Spectroscopy", Journal of Raman Spectroscopy, Mar. 16, 2015, vol. 46, pp. 434-446, doi: 10.1002/jrs.4678.
Lyandres et al., "Real-Time Glucose Sensing by Surface-Enhanced Raman Spectroscopy in Bovine Plasma Facilitated by a Mixed Decanethiol/Mercaptohexanol Partition Layer", Analytical Chemistry, Oct. 1, 2005, vol. 77, No. 19, pp. 6134-6139, doi: 10.1021/ac051357u.
Malone et al., "Approaches to Biofilm-Associated Infections: The Need for Standardized and Relevant Biofilm Methods for Clinical Applications", Expert Review of Anti-infective Therapy, 2017, Fist Published Dec. 9, 2016, vol. 15, No. 2, pp. 147-156, doi: 10.1080/14787210.2017.1262257.
Marcus et al., "Implications of Modelling the Chromophore of Rhodopsin and Bacteriorhodopsin with Resonance Raman Spectra of Retinal Schiff Bases", Journal of Raman Spectroscopy, Feb. 1979, vol. 8, No. 1, pp. 22-25, doi: 10.1002/jrs.1250080106.
Maury et al., "Directed Assembly of Nanoparticles onto Polymer-Imprinted or Chemically Patterned Templates Fabricated by Nanoimprint Lithography", Advanced Materials, Sep. 29, 2005, vol. 17, pp. 2718-2723, doi: 10.1002/adma.200501072.
Mayer et al., "Template-Assisted Colloidal Self-Assembly of Macroscopic Magnetic Metasurfaces", Faraday Discussions, Feb. 22, 2016, vol. 191, pp. 159-176, doi: 10.1039/c6fd00013d.
Miller et al., "Quorum Sensing in Bacteria", Annual Review of Microbiology, 2001, vol. 55, pp. 165-199, doi: 10.1146/annurev.micro.55.1.165.
Mirkin et al., "A DNA-based method for rationally assembling nanoparticles into macroscopic materials", Nature, Aug. 15, 1996, vol. 382, pp. 607-609, doi: 10.1038/382607a0.
Moerland et al., "Subnanometer-Accuracy Optical Distance Ruler Based on Fluorescence Quenching by Transparent Conductors", Optica, Jan. 21, 2016, vol. 3, No. 2, pp. 112-117, doi: 10.1364/optica.3.000112.
Monahan et al., "Rapid Conversion of Pseudomonas Aeruginosa to a Spherical Cell Morphotype Facilitates Tolerance to Carbapenems and Penicillins but Increases Susceptibility to Antimicrobial Peptides", Antimicrobial Agents and Chemotherapy, Apr. 2014, early publication Jan. 13, 2014, vol. 58, No. 4, pp. 1956-1962, doi: 10.1128/AAC.01901-13.
Monti et al., "Simulation of Gold Functionalization with Cysteine by Reactive Molecular Dynamics", Journal of Physical Chemistry Letters, Jan. 5, 2016, vol. 7, pp. 272-276, doi: 10.1021/acs.jpclett.5b02769.
Mortier et al., "Electronegativity-Equalization Method for the Calculation of Atomic Charges in Molecules", Journal of the American Chemical Society, Jul. 1986, vol. 108, pp. 4315-4320, doi: 10.1021/ja00275a013.
Murray et al., "Self-Organization of CdSe Nanocrystallites into Three-Dimensional Quantum Dot Superlattices", Science, Nov. 24, 1995, vol. 270, pp. 1335-1338, doi: 10.1126/science.270.5240.1335.
Nadal et al., "Electrically induced interactions between colloidal particles in the vicinity of a conducting plane", Physical Review E, Jun. 25, 2002, vol. 65, pp. 061409-1-061409-8, doi: 10.1103/PhysRevE.65.061409.
Nakajima et al., "Mechanism of Amide Formation by Carbodiimide for Bioconjugation in Aqueous Media", Bioconjugate Chemistry, Jan. 1995, vol. 6, No. 1, pp. 123-130, doi: 10.1021/bc00031a015.
Nakano, "A Space-time-Ensemble Parallel Nudged Elastic Band Algorithm for Molecular Kinetics Simulation", Computer Physics Communications, Feb. 2008, vol. 178, pp. 280-289, 10.1016/j.cpc.2007.09.011, available online Oct. 7, 2007.
Nam et al., "Plasmonic Nanogap-Enhanced Raman Scattering with Nanoparticles", Accounts of Chemical Research, Nov. 8, 2016, vol. 49, pp. 2746-2755, doi: 10.1021/acs.accounts.6b00409.
Natan, "Concluding Remarks : Surface enhanced Raman scattering", Faraday Discussions, Mar. 28, 2006, vol. 132, pp. 321-328, doi: 10.1039/b601494c.
Nguyen et al., "Robust SERS Spectral Analysis for Quantitative Detection of Pycocyanin in Biological Fluids", Proceedings of SPIE, vol. 10352, Biosensing and Nanomedicine X, Sep. 19, 2017, pp. 1035205-1-1035205-8, doi: 10.1117/12.2267958.
Ni et al., "Cascaded Assembly of Complex Multiparticle Patterns", Langmuir, 2014, Dec. 19, 2013, vol. 30, pp. 90-95, doi: 10.1021/la403956e.
Novak et al., "Assembly of Phenylacetylene-Bridged Silver and Gold Nanoparticle Arrays", Journal of the American Chemical Society, Apr. 8, 2000, vol. 122, No. 16, pp. 3979-3980, doi: 10.1021/ja000477a.
Novotny et al., "Principles of Nano-Optics", Cambridge University Press, 2012, first published 2006. 578 pgs. (presented in four parts).
Oberdick et al., "Electrophoretic Deposition of Iron Oxide Nanoparticles on Templates", Journal of Physical Chemistry C, Aug. 14, 2013, vol. 117, pp. 18709-18718, doi: 10.1021/jp405395y.
Parker et al., "Raman Scattering by Silicon and Germanium", Physical Reviews, Mar. 15, 1967, vol. 155, No. 3, pp. 712-714, doi: 10.1103/PhysRev.155.712.
Pilo-Pais et al., "Surface-Enhanced Raman Scattering Plasmonic Enhancement Using DNA Origami-Based Complex Metallic Nanostructures", Nano Letters, Mar. 19, 2014, vol. 14, pp. 2099-2104, doi: 10.1021/nl5003069.
Plimpton, "Fast Parallel Algorithms for Short-Range Molecular Dynamics", Journal of Computational Physics, Mar. 1, 1995, vol. 117, pp. 1-19, doi: 10.1006/jcph.1995.1039.
Prieve et al., "2-D assembly of colloidal particles on a planar electrode", Current Opinion in Colloid & Interface Science, Jun. 2010, vol. 15, pp. 160-174, available online Jan. 28, 2010.
Prodan et al., "A hybridization model for the plasmon response of complex nanostructures", Science, Oct. 17, 2003, vol. 302, No. 5644, pp. 419-422.
Puchkova et al., "DNA Origami Nanoantennas with over 5000-fold Fluorescence Enhancement and Single-Molecule Detection at 25 µM", Nano Letters, Nov. 2, 2015, vol. 15, pp. 8354-8359, doi: 10.1021/acs.nanolett.5b04045.

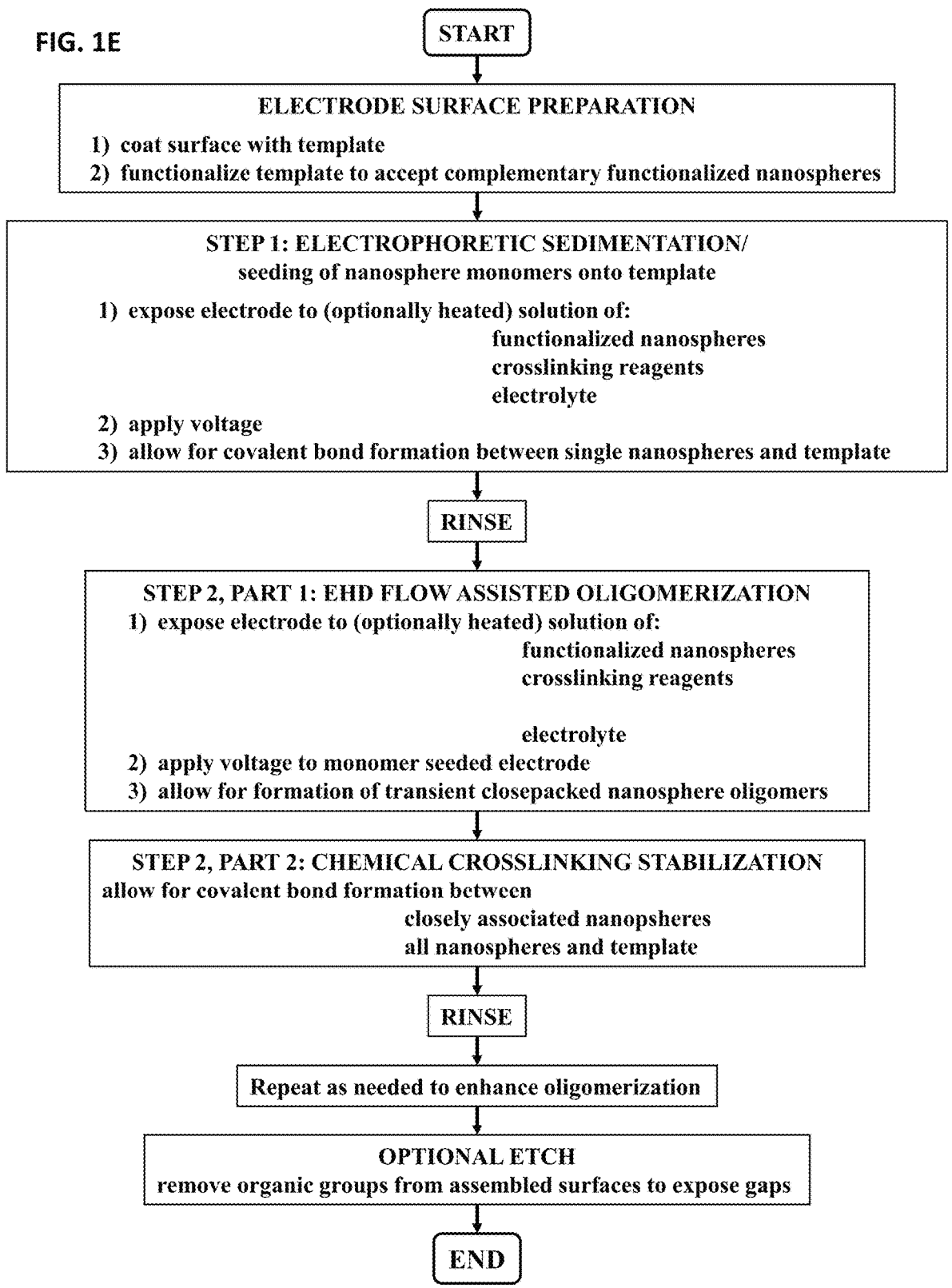

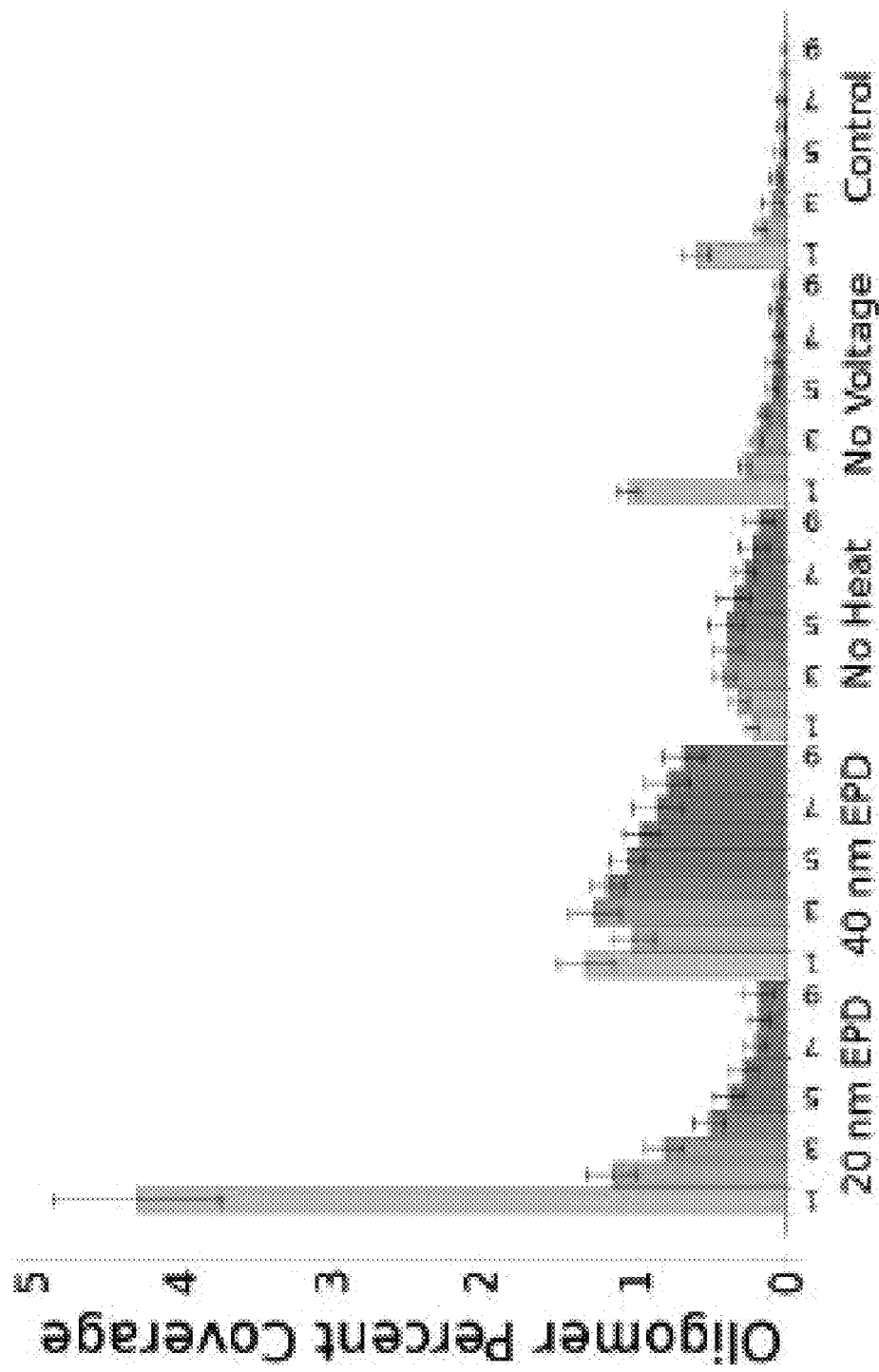

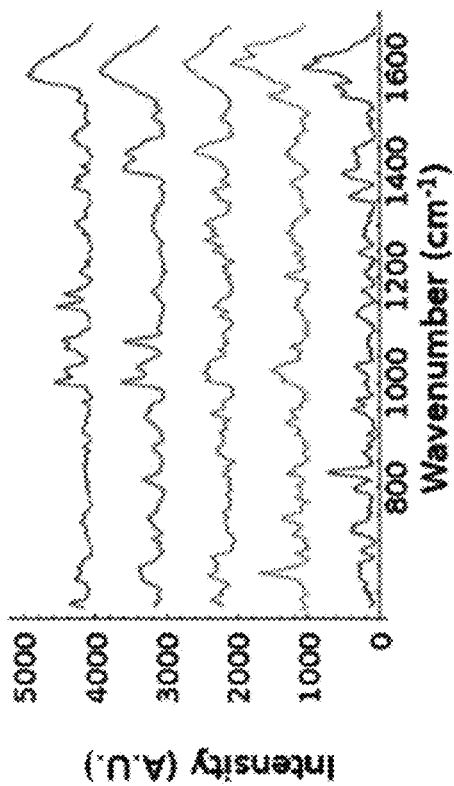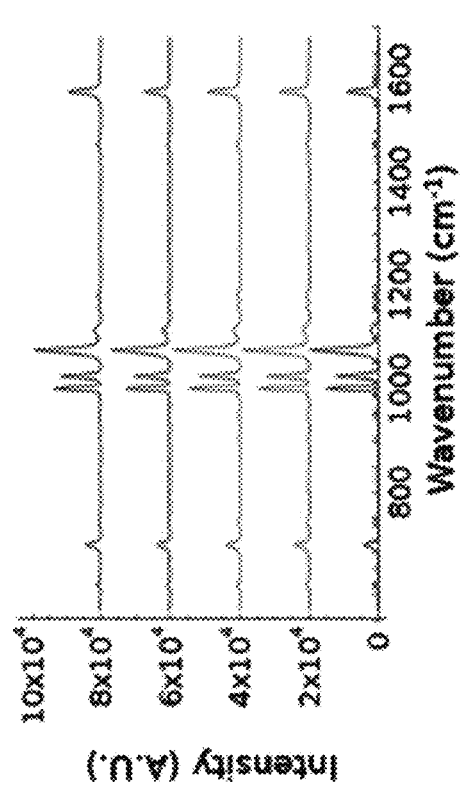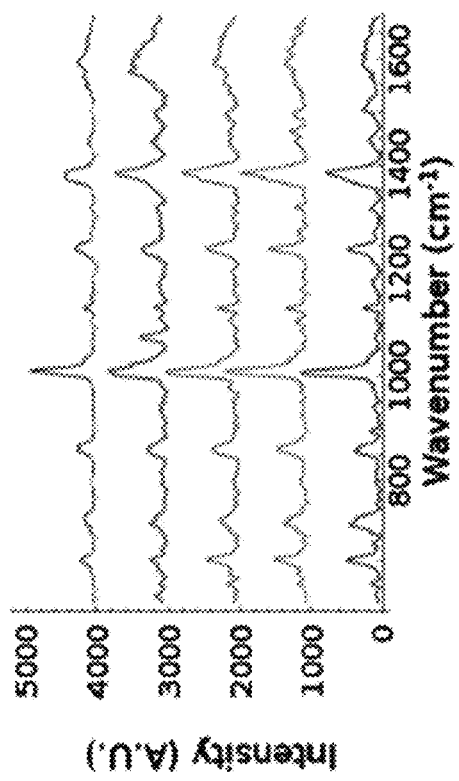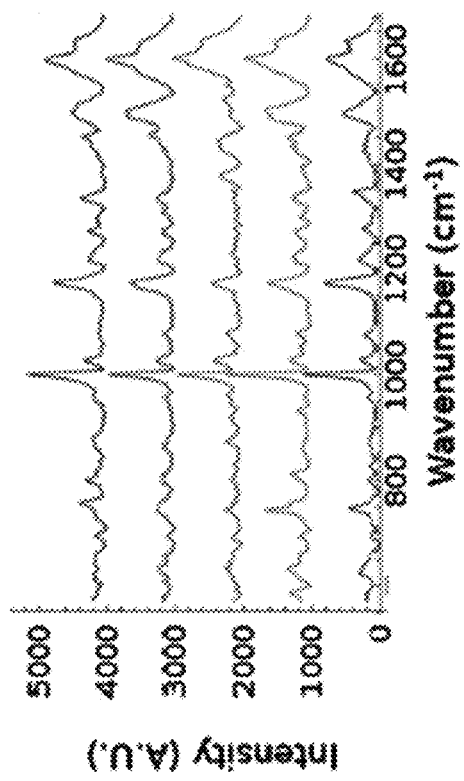

METASURFACES COMPRISED OF NANOSPHERE OLIGOMERS WITH UNIFORM NARROW GAP SPACINGS, THEIR METHOD OF FABRICATION AND APPLICATIONS IN SENSING

CROSS-REFERENCE TO RELATED APPLICATIONS

The current application claims priority to U.S. Provisional Patent Application No. 62/549,903, filed Aug. 24, 2017, the disclosure of which is incorporated herein by reference.

STATEMENT REGARDING FEDERALLY SPONSORED RESEARCH

This invention was made with Government support under Grant No. 1449397, awarded by the National Science Foundation. The Government has certain rights in this invention.

FIELD OF THE INVENTION

The invention is generally directed to nanoarchitectures comprised of subwavelength nanosphere oligomers in 2-dimensional close packed structures with uniform narrow gap spacings for plasmonic and metamaterial devices, as well as methods of fabrication thereof, biosensor systems based thereon, and methods of detection of pathogenic or other organisms using the same.

BACKGROUND OF THE INVENTION

Metal nanoarchitectures can serve as antennas at optical frequencies by efficiently controlling propagating radiation and localized fields at sub-wavelength dimensions. Precisely engineered assemblies of such antennas are termed plasmonic devices, metamaterials, or, in the case of 2-dimensional structures—metasurfaces. Nanoparticles from colloidal solution—with controlled composition, size, and shape—serve as excellent building blocks for plasmonic devices and metasurfaces. In particular, colloidal nanoparticles allow for a scalable self-assembly and, as such, for fabrication of high-density light matter controlling architectures over large areas.

Raman spectroscopy is a versatile spectroscopic technique, which provides information on molecular vibrations and crystal structures. It is based on measuring Raman scattering, which is unique to the chemical bonds in the system and allows the chemical composition of a sample to be analyzed and characterized. Surface-enhanced Raman spectroscopy or surface-enhanced Raman scattering (SERS) is an extension of Raman spectroscopy, wherein metallic nanostructures are used to enhance the intensity of Raman scattering and, as a result, to substantially improve the limit of detection, allowing very small concentration of substances to be detected and identified. More specifically, SERS is a surface-sensitive technique that enhances Raman scattering by molecules adsorbed on rough metal surfaces or by nanostructures such as, for example plasmonic-magnetic silica nanotubes. SERS enhancement factor can be as much as $10^{10}$ to $10^{11}$, which means the technique may, in theory, detect single molecules.

In particular, SERS spectroscopy has the relatively unique capacity to reach trace molecular detection limits (near parts-per-trillion) in a label-free format. Consequently, SERS has potential applications in various fields from analytical chemistry to environmental monitoring and forensic sciences. As a more specific example, SERS detection of bacterial metabolites at low concentrations in fluids with complex background allows for applications ranging from detecting biomarkers of respiratory infections to identifying contaminated medical instruments.

SUMMARY OF THE INVENTION

Embodiments of the invention are generally directed to 2-dimensional nanoarchitectures comprised of subwavelength nanosphere oligomers with uniform narrow gap spacings for plasmonic and metamaterial devices, as well as methods of fabrication thereof, biosensor systems based thereon, and methods of detection of pathogenic or other organisms using the same.

One embodiment of the invention is a metasurface including: an electrode having a surface area; a template at least partially functionalized with chemically active functional groups and disposed on the surface area of the electrode; and at least one cluster comprised of at least two nanospheres disposed on top of the template, wherein each of the at least two nanospheres is crosslinked to one of the following: the template, at least one other nanosphere of the at least two nanospheres of the at least one cluster, or to both via a molecular linker, such that the attachment between the at least two nanospheres of the at least one cluster can be selectively broken on demand to reveal a gap spacing of more than 0.5 nm and less than 3 nm wide. In addition, the metasurface is characterized by an electric field enhancement in the hotspot region.

In a further embodiment, the metasurface is characterized by a high cluster density, a uniformity of the gap spacing over approximately 75% or more of the surface area, and an electric field enhancement in the hotspot region of above 300.

In a still further embodiment, the metasurface is characterized by the electric field enhancement in the hotspot region of on the order of 600.

In another embodiment, the electrode of the metasurface includes one of the materials selected from the list: silicon, graphene, indium tin oxide-coated glass, copper, nickel, gold or gold coated glass.

In yet another embodiment, the surface area of the electrode of the metasurface is between 1 $\mu m^2$ and 1 $cm^2$.

In still another embodiment, the template of the metasurface includes a block copolymer including chemically reactive and chemically inert domains or a self-assembled monolayer.

In an additional embodiment, the template of the metasurface includes a diblock copolymer poly(styrene-b-methyl methacrylate).

In yet a further embodiment, the template of the metasurface including a diblock copolymer poly(styrene-b-methyl methacrylate) further includes PMMA domains functionalized with amine functional groups.

In yet another embodiment, the metasurface includes at least two nanospheres including one of the elements chosen from the list: Au, Ag, or Si.

In a further additional embodiment, the metasurface includes at least two nanospheres of between 20 and 100 nm in diameter.

In still another embodiment, the metasurface includes at least two nanospheres of 20 to 40 nm in diameter excited by a 633 nm excitation source.

In another embodiment, the metasurface includes at least two nanospheres of 40 to 100 nm in diameter excited by a 785 nm excitation source.

In an additional embodiment, the metasurface includes at least two nanospheres of 40 nm in diameter.

In yet a further embodiment, the gap spacing between at least two nanospheres of the metasurface is 0.5 to 1.5 nm wide.

In still another embodiment, the gap spacing between at least two nanospheres of the metasurface is approximately 0.9 nm wide.

Another further embodiment is a method of fabricating the metasurface including: providing a colloid solution including: nanospheres, wherein each nanosphere of the nanospheres is functionalized with at least one functional group, such that, upon exposure to at least one crosslinking reagent, the at least one functional group becomes chemically active and capable of crosslinking with one or both itself and functional groups of a deposition template; at least one crosslinking reagent capable of facilitating crosslinking between the nanospheres and between the nanospheres and the deposition template; an electrolyte; providing an electrode having a surface area; providing a counter electrode at a distance from the electrode; preparing a deposition surface to guide and stabilize the fabrication, including: coating the surface area of the electrode with the deposition template configured to guide the deposition, and controllably functionalizing the deposition template with functional groups capable of crosslinking with the nanospheres in the presence of the at least one crosslinking reagent and stabilizing the deposition; seeding the deposition surface with the nanospheres to guide the fabrication and enable electrohydrodynamic flow forces, including: exposing the deposition surface to the colloid solution, applying a voltage to the electrode to induce an electrohydrodynamic flow in the solution, and allowing electrophoretic sedimentation of the nanospheres onto the deposition surface and crosslinking between the nanospheres and the deposition template to occur for a period of time sufficient to ensure even distribution of the nanosphere seeds over an entirety of the deposition surface; rinsing the deposition surface; assembling transient clusters of the nanospheres onto the deposition surface under the influence of the electrohydrodynamic flow forces and stabilizing the transient clusters of the nanospheres with chemical crosslinking to form discreet oligomeric cluster structures on the deposition surface, including: exposing the deposition surface to the colloid solution, applying the voltage to the electrode to induce an electrohydrodynamic flow and allowing the period of time, such that the nanospheres are arranged into a close-packed configuration under the influence of the electrohydrodynamic flow forces, and such that the closely associated nanospheres are cross-linked and the nanospheres and the deposition template are cross-linked to form discreet oligomeric cluster structures; and rinsing the deposition surface to yield the metasurface, wherein each of the oligomeric clusters has a nanosphere gap spacing of between 0.5 to 3 nm, and wherein the overall metasurface demonstrates an electric field enhancement in a hotspot region.

In a further embodiment, the metasurface of the method is characterized by the electric field enhancement in the hotspot region of above 300.

In yet a further embodiment, the metasurface of the method is characterized by the electric field enhancement in the hotspot region of on the order of 600.

In another embodiment, the method includes repeated exposure of the deposition surface to the colloid solution, followed by rinsing, to enhance growth of the oligomeric clusters.

In a still another embodiment, the method includes treating the metasurface with a chemical agent configured to selectively break crosslinking between the nanospheres deposited on the metasurface to expose the gap spacings.

In a still further embodiment, the chemical agent of the method configured to selectively break crosslinking between the nanospheres deposited on the metasurface to expose the gap spacings is chosen from the list: oxygen plasma, chemical base, chemical acid.

In yet a further embodiment, the chemical agent of the method configured to selectively break crosslinking between the nanospheres deposited on the metasurface to expose the gap spacings is ammonium hydroxide.

In an additional embodiment, the colloid solution of the method is heated to a temperature that is above room temperature.

In yet another embodiment, the temperature of the colloid solution of the method is between 10 and 80° C.

In a further embodiment, the temperature of the colloid solution of the method is between 60° C.

In another embodiment, the nanosphere gap spacings of the method are 0.5 to 1.5 nm.

In yet another embodiment, the nanosphere gap spacings of the method are approximately 0.9 nm.

In an additional embodiment, the electrode of the method includes one of the materials selected from the list: silicon, graphene, indium tin oxide-coated glass, copper, nickel, gold or gold coated glass.

In still another embodiment, the surface area of the electrode of the method is between 1 $\mu m^2$ and 1 $cm^2$.

In a further embodiment, the deposition template of the method includes a block copolymer including chemically reactive and chemically inert domains or a self-assembled monolayer.

In yet further embodiment, the deposition template of the method includes a diblock copolymer poly(styrene-b-methyl methacrylate).

In still another embodiment, the PMMA domains of the deposition template of the method including a diblock copolymer poly(styrene-b-methyl methacrylate) are functionalized with amine functional groups.

In an additional embodiment, the method includes nanospheres including one of the elements chosen from the list: Au, Ag, Si.

In a further embodiment, the method includes nanospheres of between 20 and 100 nm in diameter.

In yet a further embodiment, the method includes nanospheres of 20 to 40 nm in diameter excited by a 633 nm excitation source.

In still a further embodiment, the method includes nanospheres of 40 to 100 nm in diameter excited by a 785 nm excitation source.

In another embodiment, the method includes nanospheres of 40 nm in diameter.

In a still further embodiment, the method includes nanospheres functionalized with at least one functional group from the list: carboxylic acid, alcohol, amine, azide, terminal alkyne, trichlorosilane, triethoxysilane, halide.

In still another embodiment, the method includes at least one crosslinking reagents including 1-ethyl-3-[3-(dimethylamino)propyl]carbodiimide hydrochloride and N-hydroxy sulfosuccinimide.

In an additional further embodiment, the method includes an electrolyte selected from the list: 2-(N-morpholino)-ethanesulfonic acid salt, KCl, NaCl, $NaHCO_3$, HCl, or any combination thereof.

In still another embodiment, the method includes a counter electrode including platinum or platinum mesh.

In an additional embodiment, the distance between the electrode and the counter electrode of the method is from 90 µm to 1.5 mm and the voltage is AC or DC.

In yet another further embodiment, the distance between the electrode and the counter electrode of the method is from 90 to 500 µm, the voltage is AC and is 5 to 8V.

In a still further another embodiment, the distance between the electrode and the counter electrode of the method is 0.5 to 1.5 mm, the voltage is DC and is 1.0-1.4V.

In yet another embodiment, the voltage of the method is DC and is 1.2 V.

In still another embodiment, the duration of a deposition cycle of the method is 5 to 60 minutes long.

In yet another embodiment, the duration of a deposition cycle of the method is 10 minutes long.

A further embodiment is a biosensor for detection of bacterial metabolites including: a metasurface including: an electrode having a surface area; a template at least partially functionalized with chemically active functional groups and disposed on the surface area of the electrode; at least one cluster including at least two nanospheres disposed on top of the template, wherein each of the at least two nanospheres is crosslinked to one of the following: the template, at least one other nanosphere of the at least two nanospheres of the at least one cluster, or to both via a molecular linker, such that the attachment between the at least two nanospheres of the at least one cluster can be selectively broken on demand to reveal a gap spacing of more than 0.5 nm and less than 1.5 nm wide; and the metasurface is characterized by an electric field enhancement in the hotspot region of above 300 and detection limits of parts per billion or lower; and a sensor configured to interrogate the metasurface to achieve detection of metabolites in contact with the metasurface.

A still further embodiment is a microfluidic device for longitudinal detection of bacterial metabolites including: at least one microfluidic channel including a metasurface, wherein the metasurface includes: an electrode having a surface area; a template at least partially functionalized with chemically active functional groups and disposed on the surface area of the electrode; at least one cluster including of at least two nanospheres disposed on top of the polymeric template, wherein each of the at least two nanospheres is crosslinked to one of the following: the template, at least one other nanosphere of the at least two nanospheres of the at least one cluster, or to both via a molecular linker, such that the attachment between the at least two nanospheres of the at least one cluster can be selectively broken on demand to reveal a gap spacing of more than 0.5 nm and less than 3 nm wide; and wherein the metasurface is characterized by an electric field enhancement in the hotspot region of above 300 and detection limits of parts per billion or lower; and wherein the at least one microfluidic channel is connected to at least one analyte source, a pump, a laser, and a spectrometer.

Another further embodiment is a method for detection of bacterial metabolites comprising: providing a biosensor including: a metasurface including: an electrode with a surface area; a template at least partially functionalized with chemically active functional groups and disposed on the surface area of the electrode; at least one cluster including at least two nanospheres disposed on top of the template, wherein each of the at least two nanospheres is crosslinked to one of the following: the template, at least one other nanosphere of the at least two nanospheres of the at least one cluster, or to both via a molecular linker, such that the attachment between the at least two nanospheres of the at least one cluster can be selectively broken on demand to reveal a gap spacing of more than 0.5 nm and less than 3 nm wide; and wherein the metasurface is characterized by an electric field enhancement in the hotspot region of above 300 and detection limits of parts per billion or lower; and a sensor configured to interrogate the metasurface to achieve detection of metabolites in contact with the metasurface; and exposing the metasurface to an analyte; and collecting data from the sensor.

In still another embodiment, the method for detection of bacterial metabolites includes analyzing the data using a multivariate machine learning algorithm based on a large number of training data sets.

In further another embodiment, the method for detection of bacterial metabolites includes the multivariate analysis that is a partial least square regression analysis.

Additional embodiments and features are set forth in part in the description that follows, and in part will become apparent to those skilled in the art upon examination of the specification or may be learned by the practice of the disclosed subject matter. A further understanding of the nature and advantages of the present disclosure may be realized by reference to the remaining portions of the specification and the drawings, which forms a part of this disclosure.

BRIEF DESCRIPTION OF THE DRAWINGS

These and other features and advantages of the present invention will be better understood by reference to the following detailed description when considered in conjunction with the accompanying data and figures, wherein:

FIGS. 1A through 1E provide various schematics of the metasurface and fabrication set-ups and procedures according to embodiments, wherein FIG. 1B also describes fabrication based on Brownian motion according to the prior art.

FIGS. 5A through 5F illustrate data analysis collected from experiments probing various metasurface fabrication parameters according to embodiments with statistical data (FIG. 5A) and SEM images (FIGS. 5B through 5F).

FIG. 17C compares the predictive model using data from the metasurface of embodiments (circles) with a standard detection method and UV absorption (triangles), while FIG. 17D compares optical density.

FIGS. 23A through 23D demonstrate reproducibility and stability of SERS response from metasurface assembled according to embodiments.

DETAILED DISCLOSURE

Figure 1A:
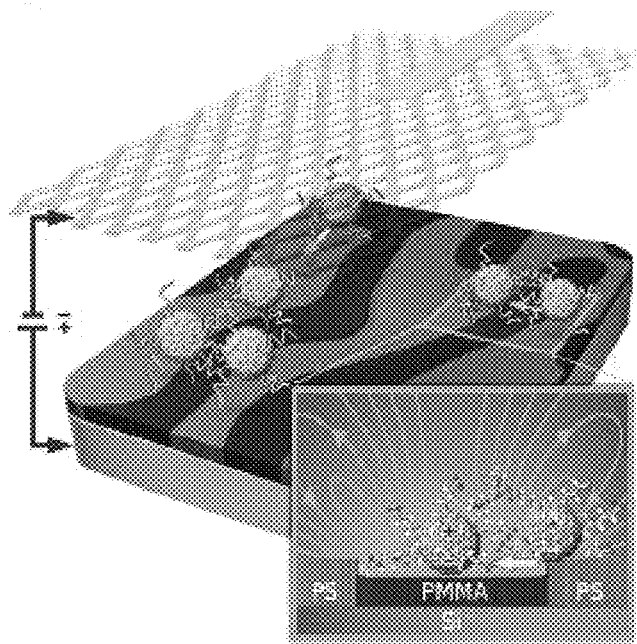

Turning now to the drawings, schemes, and data, 2D nanoarchitectures comprised of subwavelength nanosphere oligomers with uniform narrow gap spacings for plasmonic and metamaterial devices are described, as well as methods of fabrication thereof, a biosensor system based thereon, and methods of detection of pathogenic or other organisms (e.g., bacteria) using the same. It will be understood that the embodiments of the invention described herein are not intended to be exhaustive or to limit the invention to precise forms disclosed. Rather, the embodiments selected for description have been chosen to enable one skilled in the art to practice the invention.

Advances in understanding chemical and physical driving forces in molecular and particle self-assemblies now allow the fabrication of unique nanoarchitectures. Much of the effort in the assembly of nanospheres from colloids has led to long-range order in superlattice thin films on the wafer scale, marking significant progress in the ability to structure matter from molecular to mesoscopic length scales. (See, Murray, C. B., et al. Science 1995, 270, 1335-1338; Gaulding, E. A., et al. Adv. Mater. 2015, 27, 2846-2851; Gong, J., et al. Nat. Commun. 2017, 8, 14038; the disclosures of which are incorporated herein by reference.) In contrast, embodiments of methods and systems demonstrate metal nanoparticle architectures self-assembled from colloidal solutions into discrete structures (not films) that have shown great promise as building blocks for plasmonic and metamaterial devices. More specifically, it has been demonstrated that metal nanoparticles from colloids can be assembled over large self-organized chemical patterns that produce enhanced electromagnetic fields. (See, Choi, J. H., et al. Nanotechnology 20, 65301 (2009), the disclosure of which is incorporated herein by reference.) The advantages of the colloidal self-assembly methods for metasurface applications, include good control over the composition, size, and shape of nanoparticles, as well as scale up capabilities, which, together, allow for consistent fabrication of large area devices.

Furthermore, colloid-based assembly methods are often preferred over conventional optical lithography methods in fabrication of narrowly spaced discreet nanoparticle assemblies. The discrete nanoparticle assemblies are often preferred over closed-packed films for 2D plasmonics and metasurfaces, wherein the discrete assemblies are often referred to as oligomers, as the electromagnetic (optical) response is analogous with energy shifts with formation of molecular bonds. (See, Prodan, E., et al. Science 2003, 302, 419-422, the disclosure of which are incorporated herein by reference.) For example, devices that rely on narrow-band resonances—i.e., Fano resonances—based on "dark" (i.e., low scattering) electric and magnetic resonances can be advantageously realized via formation of discrete sub-wavelength metal nanoparticle clusters. (See, Ye, J. et al. Nano Lett. 12, 1660-1667 (2012); Zhang, Y., et al. Proc. Natl. Acad. Sci. (2013); Campione, S., et al. Opt. Lett. 38, 5216-5219 (2013); and Campione, S., et al. ACS Photonics 1, 254-260 (2014); the disclosures of which are incorporated herein by reference.) In this example, the conventional split-ring resonators, that in principle could provide narrow band resonances, are prohibitively difficult to scale down to optical wavelengths, which is necessary to counteract the fading of the natural magnetism at infrared and optical frequencies. (See Klein, et al. Opt. Lett. 31, 1259 (2006), the disclosure of which are incorporated herein by reference.) In contrast, discrete clusters of coupled nanospheres can be properly scaled. (See Alù, A. & Engheta, N. Phys. Rev. B 78, 85112 (2008); Liu, N. et al. ACS Nano 6, 5482-5488 (2012); the disclosures of which are incorporated herein by reference.) As another example, surface enhanced Raman scattering (SERS) sensors also exhibit better physical performance with discrete metal nanoparticle clusters rather than hexagonally close packed nanoparticle layers. (See, Adams, S. M., et al. Langmuir 29, 4242-4251 (2013); Campione, S., Adams, S. M., et al. Opt. Express 21, 7957 (2013); the disclosures of which are incorporated herein by reference.)

In the instances of metasurfaces comprised of discrete nanoparticle clusters, such as those described in the examples above or others, the gap spacings between the nanoparticles within a cluster are an important parameter in tuning the device optical response. Specifically, when using optical antennas to enhance spontaneous emission, it is critical to control the gap spacings to balance between increased spontaneous emission rate and losses resulting from optical spreading resistance and the skin effect. (See, Eggleston, M. S., et al. Proc. Natl. Acad. Sci. 112, 1704-1709 (2015), the disclosure of which is incorporated herein by reference.) Furthermore, it has been shown by Novotny, L. & Hecht, B. in Principles of Nano-Optics Cambridge University Press, 2012, the disclosures of which are incorporated herein by reference) that when electromagnetic radiation impinges on nanoantennas (i.e. oligomers) with small gaps (i.e., hotspots), the electric field is greatly enhanced. In metal nanoarchitectures, this enhancement is induced by localized surface plasmon resonance and increases with decreasing gap spacings until the gap spacings are approximately 0.5 nm wide. As such, nanoscale optical devices produced to take advantage of the performance enhancements resulting from narrower gap spacings rival bulk devices.

However, fabrication of devices with sufficiently narrow nanoparticle gaps via the traditional optical lithography methods is challenging. Specifically, although electron beam lithography (see Zhu, W. & Crozier, K. B. Nat. Commun. 5, 5228 (2014), the disclosures of which are incorporated herein by reference) can produce gap spacings as narrow as approximately 0.5 nm, which reaches (and even surpasses) the quantum mechanical tunneling regime, achieving gaps near this limit over large areas remains an on-going challenge for device fabrication. Therefore, new robust fabrication methods for assembly of nanoparticles into discrete, yet dense (narrowly spaced) clusters over large area surfaces are needed for development of a new generation of compact optical devices.

Nanoparticle colloids can provide metamolecule building blocks wherein not only composition, size, and shape of the nanoparticle, but the geometry of resultant oligomers, gap spacings, and dielectric environment provide additional degrees of freedom for tuning the electromagnetic response. As such, it has been demonstrated that metal nanoparticles from colloids can be assembled in oligomers over large areas using self-organized chemical patterns that produce enhanced electromagnetic fields for SERS sensors. (See, Adams, S. M., et al. Small 2012, 8, 2239-2249, the disclosures of which are incorporated herein by reference.) Moreover, use of diffraction-limited sources to define patterns for large oligomers or random deposition of isolated nanoparticles on surfaces has since produced ultrathin quarter-wave plates, perfect absorbers, and ultrafast spontaneous emission sources. (See, respectively: Chen, W. et al. Nano Lett. 15, 5254-5260 (2015); Akselrod, G. M. et al. Adv. Mater. 27, 8028-8034 (2015); and Hoang, T. B. et al. Ultrafast spontaneous emission source using plasmonic nanoantennas. Nat. Commun. 6, 7788 (2015); the disclosures of which are incorporated herein by reference). (Sub)nanometer gaps between plasmonic nanoparticles have led to light-matter interactions including single-molecule surface-enhanced Raman scattering (SERS) spectroscopy, room-temperature single-molecule strong coupling, and second-harmonic generation. (See, e.g.: Kneipp, K., et al. Phys. Rev. Lett. 1997, 78, 1667-1670; Chikkaraddy, R. et al. Nature 2016, 535, 127-130; Biswas, S., et al. Nano Lett. 2015, 15, 1836-1842, the disclosures of which are incorporated herein by reference.) However, fabrication of discrete assemblies at nanoscale (sub-100 nm) dimensions with controlled (sub) nanometer gap spacing and at high densities over large areas remains challenging. (See, Hamon, C., et al. Chem.—Eur. J. 2015, 21, 9956-9963; Nam, J.-M., et al. Acc. Chem. Res. 2016, 49, 2746-2755, the disclosures of which are incorporated herein by reference.)

Nevertheless, efforts towards fabrication of the very desirable discrete, yet narrow-spaced, assemblies from colloid solution continue. For example, long-range driving forces (~μm scale) have been used extensively in colloidal assembly, including capillary forces, convection, optical tweezing, electrophoresis, and electrokinetic phenomena (electrically driven fluid flow and particle motion). (See, respectively: Greybush, N. J., et al. ACS Nano 2017, 11, 2917-2927; Flauraud, V., et al. Nat. Nanotechnol. 2017, 12, 73-80; Ni, S., et al. Langmuir 2014, 30, 90-95; Fleck, N. A., et al. Langmuir 2015, 31, 13655-13663; Ye, R., et al. Langmuir 2013, 29, 1796-1801; Jaquay, E., et al. Nano Lett. 2014, 14, 5184-5188; Oberdick, S. D., et al. J. Phys. Chem. C 2013, 117, 18709-18718; Yilmaz, C., et al. ACS Nano 2014, 8, 4547-4558; Work, A. H. & Williams, S. J. Soft Matter 2015, 11, 4266-4272; Wang, K.-C., et al. Lab Chip 2014, 14, 3958-3967; Ristenpart, W. D., et al. Langmuir 2008, 24, 12172-12180, the disclosures of which are incorporated herein by reference.) In yet another approach, self-assembly using salt-induced aggregation was used and produced the desirable small gap spacings between nanoparticle clusters, yet such aggregation was difficult to control and resulted in large variability in both oligomer morphology and gap spacing. (See, e.g., Li, W. et al. Angew. Chem. 122, 168-172 (2010); Yang, M. et al. Phys. Chem. Chem. Phys. 12, 11850 (2010); Sreeprasad, T. S. & Pradeep, T. Langmuir 27, 3381-3390 (2011); Li, W., et al. Nano Lett. 9, 485-490 (2009), the disclosures of which are incorporated herein by reference.)

Short-range driving forces, such as electrostatic interactions, van der Waals forces, and chemical crosslinking, are also essential to control gap spacings, which has a profound impact on the optical response of plasmonic assemblies. Of these, chemical crosslinks, including DNA origami, Cucurbit[n]uril, small molecules, protein linkers, and polymer encapsulation provide the most flexibility and control in architectures achieved from colloidal dispersions. (See, e.g., Mirkin, C. A., et al. A Nature 382, 607-609 (1996); Thacker, V. V. et al. Nat. Commun. 5, 3448 (2014); Gür, F. N., et al. L. ACS Nano 10, 5374-5382 (2016); Taylor, R. W. et al. ACS Nano 5, 3878-3887 (2011); Sigle, D. O. et al. J. Phys. Chem. Lett. 7, 704-710 (2016); Van Haute, D., et al., J. M. Adv. Mater. 27, 5158-5164 (2015); Novak, J. P. & Feldheim, D. L. J. Am. Chem. Soc. 122, 3979-3980 (2000); Sardar, R., et al. J. Am. Chem. Soc. 129, 5356-5357 (2007); Zon, V. B., et al. J. Nanoparticle Res. 15, 1-10 (2013); Kim, N. H., et al. M. Adv. Mater. 23, 4152-4156 (2011); Zhang, L. et al. Langmuir 31, 1164-1171 (2015); Qian, X., et al. J. Am. Chem. Soc. 131, 7540-7541 (2009); and Zhu, M.-Q., et al. J. Am. Chem. Soc. 126, 2656-2657 (2004), the disclosures of which are incorporated herein by reference.) In fact, chemical crosslinking of colloidal nanospheres has produced among the smallest (down to sub-nanometer) gap spacings. As such, chemically crosslinked nanoparticle oligomers have found applications in surface enhanced Raman spectroscopy (SERS), surface enhanced fluorescence, and surface enhanced circular dichroism. (See, e.g., Pilo-Pais, M., et al., G. Nano Lett. 14, 2099-2104 (2014); Kasera, S., et al. Sci. Rep. 4, 6785 (2014); Puchkova, A. et al. Nano Lett. 15, 8354-8359 (2015); and Wang, R.-Y. et al. J. Phys. Chem.

C 118, 9690-9695 (2014); Zhao, Y. et al. Nano Lett. 14, 3908-3913 (2014), the disclosures of which are incorporated herein by reference.) However, while many of these crosslinking-based assembly methods are successful at producing oligomers in solution, depositing nanoclusters onto a substrate in a reproducible manner to generate uniform reproducible electromagnetic response over large area sample remains an ongoing challenge. Therefore, assemblies fabricated using chemical crosslinking methods that rely solely on diffusion typically have low oligomer density and/or incomplete assemblies.

In addition, to further address the uniformity and architecture control issues, directed self-assembly of nanospheres on templates fabricated using top-down assembly methods has been developed. (See, e.g., Fan, J. A. et al. Nano Lett. 12, 5318-5324 (2012); Mayer, M. et al. Faraday Discuss (2016) doi:10.1039/C6FD00013D; Maury, P., et al., J. Adv. Mater. 17, 2718-2723 (2005); Wang, P. et al. J. Am. Chem. Soc. (2016) doi:10.1021/jacs.6b03966, the disclosures of which are incorporated herein by reference.) However, while these methods have also found broad applicability in SERS, second harmonic generation, photon upconversion, and projection lithography, top-down fabrication of templates typically yields sparse architectures. (See, e.g., Yap, F. L., et al. ACS Nano 6, 2056-2070 (2012); Biswas, S. et al. Nano Lett. 15, 1836-1842 (2015); Greybush, N. J. et al. ACS Nano 8, 9482-9491 (2014); and Gonidec, M. et al. Nano Lett. (2016) doi:10.1021/acs.nanolett.6b00952, the disclosures of which are incorporated herein by reference.) In summary, the primary difficulties with fabrication of metasurfaces from colloids remain in achieving a high yield of oligomers that simultaneously possess all of the following characteristics: small (because field enhancement of large oligomers is reduced by loss), dense, yet discrete (to avoid inter-oligomer coupling), have uniform gap spacing, and optically uniform (in terms of both size of probe at the μm scale, and point to point over cm scale distances).

Embodiments are, accordingly, at least partly directed to metasurfaces and methods for fabrication of metasurfaces comprising densely packed, discreet nanosphere clusters (oligomers) characterized by sub-nanometer and uniform gap spacings with large scale uniformity in hot spot intensity and, therefore, suitable for uses in plasmonic and metamaterial devices, including SERS-type biosensors. More specifically, in many embodiments, and as illustrated in FIGS. 1A through 1D, the metasurfaces comprise an electrode coated with an assembly-guiding template and clusters of nanospheres covalently bound to the template, wherein some of the nanospheres in a given cluster are attached directly to the template, while others only to other nanospheres in the cluster, while yet others to both, via a small molecule linker. Furthermore, in many embodiments the attachments between nanospheres in a cluster can be selectively broken on demand to reveal gap spacings of more than 0.5 nm and less than 3 nm wide. In many embodiments, the gap spacings between the nanoparticles of metasurface clusters are 0.5 to 1.5 nm. In many such embodiments the gap spacings are approximately 0.9 nm. In many embodiments these gap spacings are uniform over the entirety of the metasurface. In many embodiments, the assembly electrode is made of one of the materials selected from the list: silicon, graphene, indium tin oxide (ITO)-coated glass, Cu, Ni, Au, Au-coated glass, or other known electrode material, and has a surface area of between 1 μm$^2$ and 1 cm$^2$. In many embodiments, the assembly-guiding template comprises a polymeric material or a self-assembly monolayer (SAM), that can be controllably functionalized with chemically active functional groups. In many such embodiments, the template comprises a block copolymer comprising chemically reactive and chemically inert domains. In many embodiments, the template comprises a diblock copolymer poly(styrene-b-methyl methacrylate) and, in many such embodiments, the PMMA domains of the template are further functionalized with amine or other functional groups. In many embodiments, the nanoparticles are comprised of one or more of: gold (Au), silver (Ag), or silicon (Si). Furthermore, in many embodiments, the nanoparticles are between 20 and 100 nm in diameter. In many embodiments, the nanoparticles are 20 to 40 nm in diameter when used with a 633 nm excitation source. In many embodiments, the nanoparticles are 40 to 100 nm in diameter when used with a 785 nm excitation source. In many embodiments, the nanoparticles are functionalized with chemically active end groups that, upon activation by a crosslinking reagent or reagents, enable them to attach to each other and/or to the assembly guiding template deposited on the electrode surface of the metasurfaces of the embodiments. In many such embodiments, the nanoparticles are functionalized with carboxylic acid end groups. In many embodiments, the metasurface assemblies of the application exhibit high field enhancements with plasmon resonances in the range of 615 nm-875 nm full width half maximum. In many embodiments, these nanoantenna surfaces produced according to the methods of the application exhibit uniform hotspot intensity (due to uniform gap spacing), and are excited by a 785 nm excitation source, as confirmed by full wave simulations, ultraviolet-visible spectroscopy, and surface enhanced Raman scattering (SERS). In addition, full wave simulations for the nanoantennas of the application show field enhancements of at least 600, correlating well with measured average SERS enhancement of $1.4 \times 10^9$, with a relative standard deviation of 10% over a 1 mm$^2$ area. Accordingly, in many embodiments, the electric field enhancement in the hotspot regions of the metasurfaces of embodiments is above 300. In many such embodiments, the electric field enhancement in the hotspot regions is on the order of 600. In some embodiments, the nanoantenna surfaces of the instant application are excellent candidates for SERS biosensing applications and applications related to metabolomics studies of small molecules. In other embodiments, the nanoantenna surfaces of the instant application are useful in applications that utilize light-matter interactions, such as harmonic generation, surface enhanced fluorescence, enhanced spontaneous emission, and other similar applications.

In many embodiments, the method of fabrication the application relies on a combination of long range and short range driving forces, wherein the self-assembly of colloidal nanoparticles on an assembly guiding chemically functionalized template is driven by both chemical crosslinking and electrohydrodynamic (EHD) flow. More specifically, in many embodiments, induced charge electroosmosis, also referred to as electrohydrodynamic flow, provides a long range driving force that brings nanospheres together for chemical crosslinking on a working electrode surface under a DC or AC potential with a counter electrode (FIG. 1A). Here, the distance between the working electrode and the counter electrode (the platinum mesh in FIG. 1A) is defined by the choice of DC or AC fabrication/deposition potential. For example, in some embodiments, the distance between the working electrode and the counter electrode is from 90 to 500 μm and the applied voltage is AC and is 5 to 8V. In many such embodiments, the distance between electrodes is 90 μm, and the AC voltage is 5V. In other embodiments, the distance between the working electrode and the counter electrode is 0.5 to 1.5 mm, and, accordingly the voltage is DC and is 1.0-1.4V. In many such embodiments, the distance between electrodes is 1 mm and the DC voltage is 1.2V. Precaution should be taken not to exceed these parameters, as larger electric fields may lead to electrolysis of water (colloid solvent). However, in many embodiments, much smaller potentials will lead to less coverage of metasurfaces by nanospheres.

The transient EHD assemblies are next "frozen" by crosslinking according to the embodiments to yield oligomer architectures with narrow gap spacings on a length scale ideal for field enhancement, that is larger than the quantum mechanical limit for charge transfer plasmon modes leading to depolarization. In many embodiments, the resulting gap spacings are 0.5 to 3 nm wide. In some more preferred embodiments, the gap spacings are 0.5 to 1.5 nm wide. In many embodiments, the gap spacings are approximately 0.9 nm wide. In many embodiments, EHD facilitates nanoparticle crosslinking by both promoting the formation of the anhydride bridges and their retention.

Furthermore, in many embodiments, the nanospheres are deposited onto an assembly guiding template and chemically attached to it via selective chemistry. In many such embodiments, the templated deposition of the method of the application produces oligomers with a narrower wavelength bandwidth and higher hotspot intensity than monolayer structures produced without a template. Therefore, in many embodiments, a deposition template is chosen such that it can be patterned with functional chemical groups. In many embodiments, the template comprises a polymeric material or a SAM. In many embodiments, wherein the template comprises a polymeric material, the template is comprised of poly(styrene-b-methyl methacrylate) (PS-b-PMMA), wherein the PMMA domains of the template are further functionalized with amine or other functional groups. Overall, the fabrication method of the instant application based on templated chemical crosslinking enhanced with an electric field external driving force overcomes many of the challenges associated with colloidal deposition (i.e. low oligomer density and loss associated with large oligomers), provides excellent control over colloidal nanoparticle assembly, and produces large area hotspots with a uniform, narrow gap spacing and a narrow optical response.

Figure 1B:
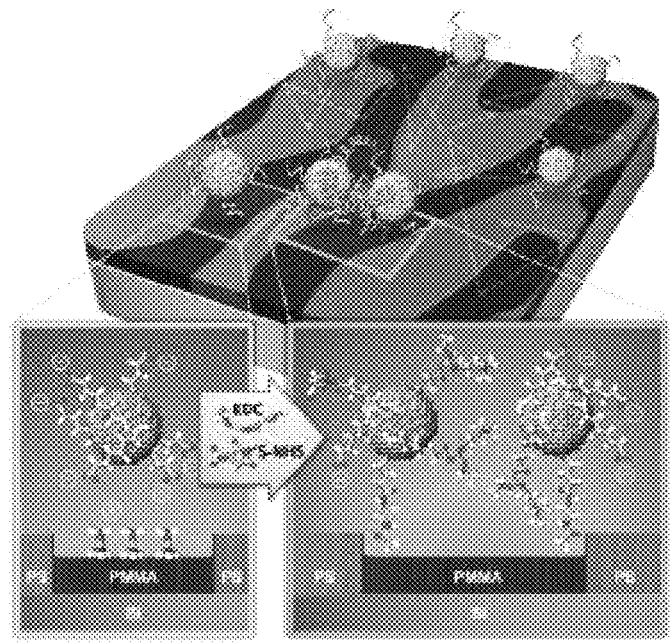

Accordingly, in many embodiments, the fabrication of metasurfaces comprising nanoparticle oligomers and characterized by uniformly distributed electromagnetic hotspots over large areas is achieved by utilizing EHD flow to drive chemical crosslinking to form nanogaps with sub-nanometer gap spacing. In many such embodiments, the chemical assembly is facilitated using a two-step growth process illustrated by the scheme in FIG. 1E: (Step 1) electrophoretic sedimentation driving chemical crosslinking of nanoparticle seeds onto a working electrode and (Step 2) growing oligomers via EHD flow (Part 1) and stabilizing them via chemical crosslinking (Part 2). More specifically, in STEP 1 of the deposition method of the embodiments, during electrophoresis depicted in FIG. 1C, functionalized nanoparticle monomer seeds are chemically assembled on complimentary functionalized templated working electrode with help of crosslinking reagents (inset). Next, in Step 2 of the deposition process of the embodiments, an applied field deforms the ionic double layer around the Au seeds, shown on the right of FIG. 1C, inducing an osmotic flow toward the seeds' equator, termed the EHD flow. These flow fields entrain nearby nanospheres and drive them toward nanoparticle seeds to form transient close-packed oligomers (Part 1 of Step 2), which are subsequently stabilized through a crosslinking reaction that forms covalent bond bridges between nanospheres, as shown in FIG. 1D. These bridges result in oligomers with uniform narrow inter-particle gap spacings, wherein the gap spacings widths correlate well with the length of the bridging functionality, as calculated from atomistic simulations and observed in transmission electron microscopy. It will be understood that any of the variants to gap spacing, surface density, etc. previously discussed may be implemented in accordance with these embodiments.

Oligomer Deposition—Template

Chemical assembly on self-organized templates has been shown to allow for the formation of discrete oligomers (that may serve as nanoantennas) over large areas. Therefore, in many embodiments, polymeric or SAM templates that can be controllably functionalized or otherwise chemically patterned serve as oligomer deposition templates in the method of the application to guide the deposition and secure the oligomer nanostructures on the assembly electrode/substrate. In many embodiments, the template is chosen to distribute nanoparticle monomer seeds evenly over the entire substrate surface. In many preferred embodiments, the assembly guiding template is comprised of a block copolymer comprising chemically active and inert blocks spaced to evenly distribute nanoparticles of embodiments over the substrate surface. In many such embodiments the template comprises poly(styrene-b-methyl methacrylate) (PS-b-PMMA) diblock copolymer. In general, PS-b-PMMA has been used to produce regular, nanometer-scale hotspots that enhance light-matter interactions. (See, e.g., Liu, Z., et al. Small 9, 505-510 (2013); Kim, S.-S. & Sohn, B.-H. RSC Adv 6, 41331-41339 (2016); and Adams, S. M. et al. Small 8, 2239-2249 (2012), the disclosures of which are incorporated herein by reference.) Specifically, PS-b-PMMA is known to minimizes interfacial energy between the two polymer blocks by self-organizing into poly-methyl methacrylate (PMMA) domains with widths of approximately 40 nm separated by polystyrene (PS) domains (FIGS. 1A and 1B). In many embodiments, the PS-b-PMMA template is composed of PMMA lamella domains with widths of 40 nm and a fractional surface coverage of 28%. Accordingly, in many embodiments, the method of the application comprises coating an electrode with a lamella PS-b-PMMA block copolymer and then annealing it. In many embodiments, PS-b-PMMA is spin-coated onto the electrode surface and annealed. In many embodiments, the electrode is one of: a heavily doped Si wafer, graphene membrane, indium tin oxide (ITO)-coated glass, Cu, Ni, Au, Au-coated glass, or other known electrode material. In many embodiments, the surface area of the electrode (substrate) is between 1 $\mu m^2$ and 1 $cm^2$.

In many embodiments, the PMMA domains of the PS-b-PMMA block copolymer template are selectively functionalized with surface chemically reactive end groups for attachment to complementary functionalized nanoparticles to be assembled on the template. In many embodiments, the surface functional end groups are amines. To this end, in many embodiments, PS-b-PMMA template is exposed to ethylenediamine reagent prior to nanoparticle deposition. In such embodiments, the PMMA domains of the template selectively react with the amination reagent to form surface amine end groups, while the PS regions are chemically inert towards ethylenediamine and remain intact. In many such embodiments, the nanoparticles to be assembled on the template are functionalized with complimentary terminal carboxylic acid groups.

Oligomer Deposition—Nanosphere Crosslinking and Template Binding

Figure 2:
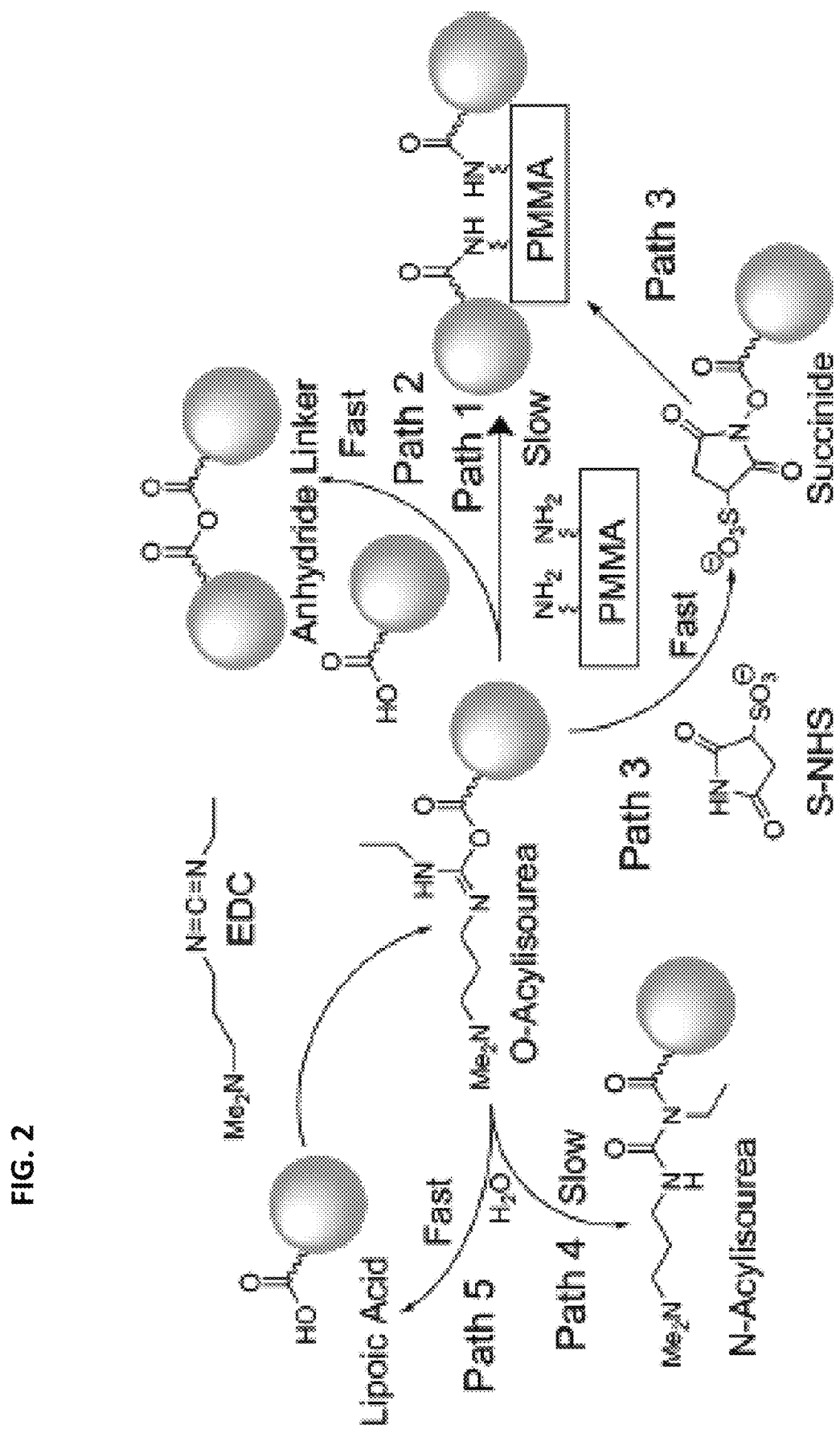
FIG. 2 provides chemical pathways behind deposition and crosslinking aspects of the metasurface fabrication according to embodiments.

In many embodiments, a bioconjugation-inspired assembly process utilizing carbodiimide crosslinker or another controlled crosslinking chemistry enables the assembly of nanospheres into discrete oligomers on the self-organized template described above. FIG. 2 illustrates the chemical pathways of carbodiimide crosslinking chemistry employed in the lipoic acid functionalized gold nanoparticle deposition method of the application. However, in some embodiments, nanoparticles comprised of different elements, such as Ag and Si, can also be used. In such embodiments, a different crosslinking chemistry, including different crosslinking reagent or reagents and different functionalization of the nanospheres and the template may be used. In some such embodiments, for example, a hydroxyalkanethiol (HO $(CH_2)_n$ SH, wherein $4<n<10$) may be used to functionalize Ag-based nanospheres or (3-Aminopropyl)triethoxysilane (APTES) may be used to functionalize Si nanospheres for depositions of embodiments via carbodiimide or another crosslinking chemistry. In some embodiments, crosslinking chemistry of azide-alkyne cycloaddition may be exploited in the deposition methods of the embodiments. In such embodiments, for example, various combinations of a 6-mercaptohexanoic acid (MHA) and 1-amino-3-butyne linkers may be used with Au and Ag nanospheres in the presence of EDC or another reagent. In some other exemplary embodiments, a combination of 3-bromopropyltrichlorosilane with sodium azide or 3-Aminopropyl)triethoxysilane (ATPES) with 4-pentynoic acid in the presence of EDC can be used in the deposition of silicon nanospheres. In many embodiments, such as those depicted in FIG. 2, the reagent that facilitates both the crosslinking of the nanoparticles and the attachment of the nanoparticles to the template is 1-Ethyl-3-(3-dimethylaminopropyl)-carbodiimide (EDC) (FIG. 2, Paths 1 and Path 2). In addition, in many embodiments, the addition of Sulfo-(N-hydroxysulfosuccinimide) (S—NHS) reagent to the deposition process also promotes attachment of nanoparticles to the template (FIG. 2, Path 3). In many embodiments, carboxylic acid terminated nanospheres are linked to the amine functionalized PMMA domains of the deposition template via peptide bond formation through consecutive reactions with EDC, similarly to the processes described in, for example, Hermanson, G. T. Bioconjugate Techniques. (Academic Press, 2013), the disclosure of which is incorporated herein by reference.

More specifically, in the embodiments involving EDC crosslinking chemistry, nanospheres are assembled on the substrate surface via two paths. First carbodiimide activates the carboxylic acid on the particle forming the isourea species, which then forms an amide bond with PMMA, labeled Path 1. Amide bond formation with PMMA can also be accelerated with S—NHS via intermediate succinimide formation, labeled Path 3. However, the activated isourea may also react with carboxylic acids, yielding anhydride bonds as labeled in Path 2. (See, Nakajima, N.; et al. Bioconjugate Chem. 1995, 6, 123-130, the disclosures of which are incorporated herein by reference.) Anhydride bond formation is not frequently observed, and, when observed, it has been attributed to the close proximity between carboxylic acid groups during polymer crosslinking and related to the Thorpe-Ingold effect in cyclization reactions. (See, Yan, Q., et al. RSC Adv. 2015, 5, 69939-69947, the disclosures of which are incorporated herein by reference.)

Oligomer Deposition—Electrohydrodynamic (EHD) Flow

Figure 1C:
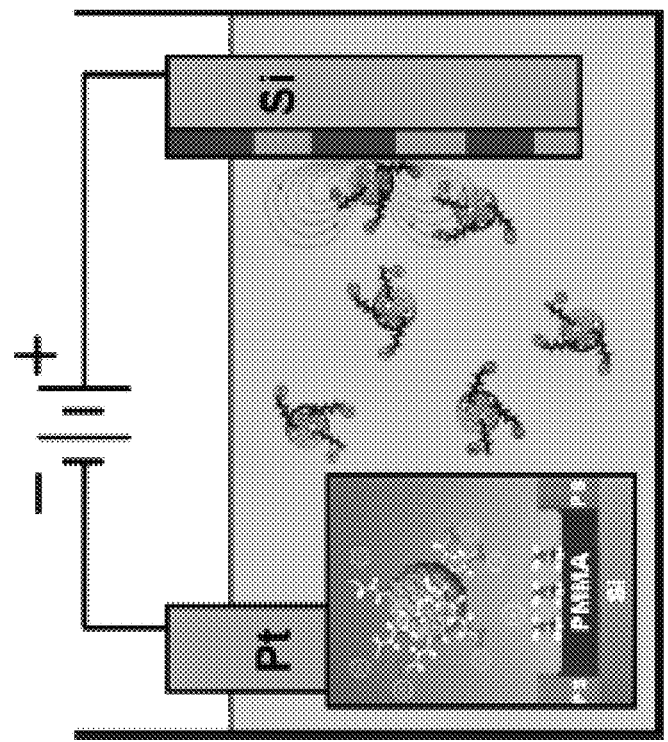
Figure 1D:
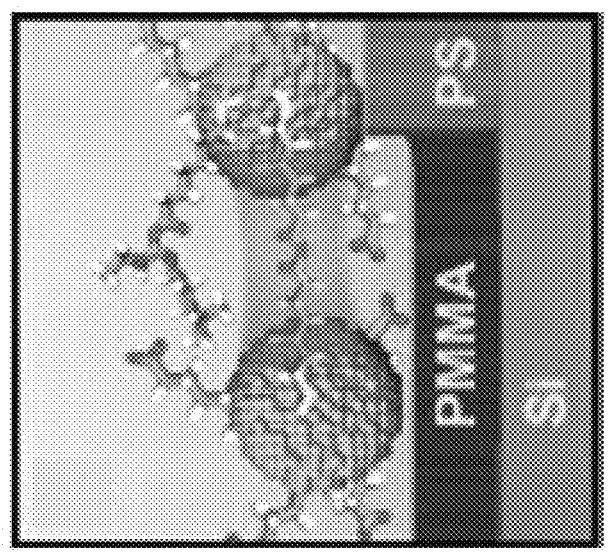

In many embodiments the oligomer deposition on the assembly template is assisted by an applied electric field (FIGS. 1A, 1C, and 1D). In such embodiments, an applied electric field drives the nanospheres toward the template surface in a process termed electrophoretic sedimentation or electrophoretic deposition (EPD). Additionally, in many such embodiments, the applied potential generates EHD flow. (See, Woehl, T. J., et al. Langmuir 30, 4887-4894 (2014), the disclosure of which is incorporated herein by reference.) EHD flow is an electrokinetic phenomenon that arises from lateral potential gradients within an electrode polarization layer and has been studied for both ac and dc applied potentials. (See, Trau, M., et al. Langmuir 1997, 13, 6375-6381; Squires, T. M., et al. J. Fluid Mech. 2004, 509, 217-252; Saini, S., et al. Langmuir 2016, 32, 4210-4216; Prieve, D. C.; et al., Curr. Opin. Colloid Interface Sci. 2010, 15, 160-174; the disclosures of which is incorporated herein by reference.) The resultant flow can be radially attractive toward the source of the gradient and in the deposition method of the application a seeded nanosphere in the lateral plane of an electrode is used to generate the gradient. EHD flow has been primarily studied in the context of micrometer-scale particles, where particles become entrained in flow fields resulting in 2-dimensional close-packed assemblies. Resultant structures are transient and are typically imaged in situ using confocal microscopy, making it difficult to understand assembly behavior at sub-100 nm dimensions.

More specifically, in the course of the applied electric field assisted nanoparticle deposition according to the method of the application, a local inhomogeneous electric field is generated due to the polarization of the nanospheres initially bound to the assembly template coated electrode surface. This field, in turn, drives ion motion, and, thus, fluid flow. In other words, the source of the fluid flow upon application of a current is equilibrium charge electroosmosis due to Faradaic currents, wherein the general term for fluid flow generated by this and other related mechanisms is electrohydrodynamic (EHD) flow. (See, e.g., Prieve, D. C., et al. Curr. Opin. Colloid Interface Sci. 15, 160-174 (2010), the disclosure of which is incorporated herein by reference.) The net result is a lateral attractive force between nanospheres at the colloid solution/electrode interface that causes the nanospheres to aggregate. Furthermore, during EPD, the electric field leads to electrolysis that reduces the pH at electrode surfaces, and, thus, minimizes the electrostatic repulsion between carboxylate end groups on the nanospheres. Therefore, in many embodiments, the oligomer deposition comprises at least two EPD deposition cycles, wherein the first deposition cycle generates high density nanosphere seeds on the templated electrode surface to serve as perturbation sites necessary for EHD flow, and the second deposition cycle promotes the formation of oligomers. In many embodiments, each deposition cycle lasts no more than 10 minutes to minimize decomposition of the activated O-acylisourea into an inert N-acylisourea, which prevents further oligomer growth. However, in some embodiments, a deposition cycle may last from 5 to 60 minutes. In addition, in many embodiments, EHD flow, which is a combination of electroosmotic flows, is enabled by the presence of an electrolyte in the colloid solution. In some embodiments, the electrolyte is selected from the list: 2-(N-morpholino)-ethanesulfonic acid (MES) salt, KCl, NaCl, NaHCO$_3$, HCl, or any combination thereof. In some embodiments, 2.3 mM MES salt is included in the colloidal solution. FIG. 1A includes a schematic inset showing the flow field and the mechanism behind long range EHD driving force bringing nanospheres together.

Figure 3:
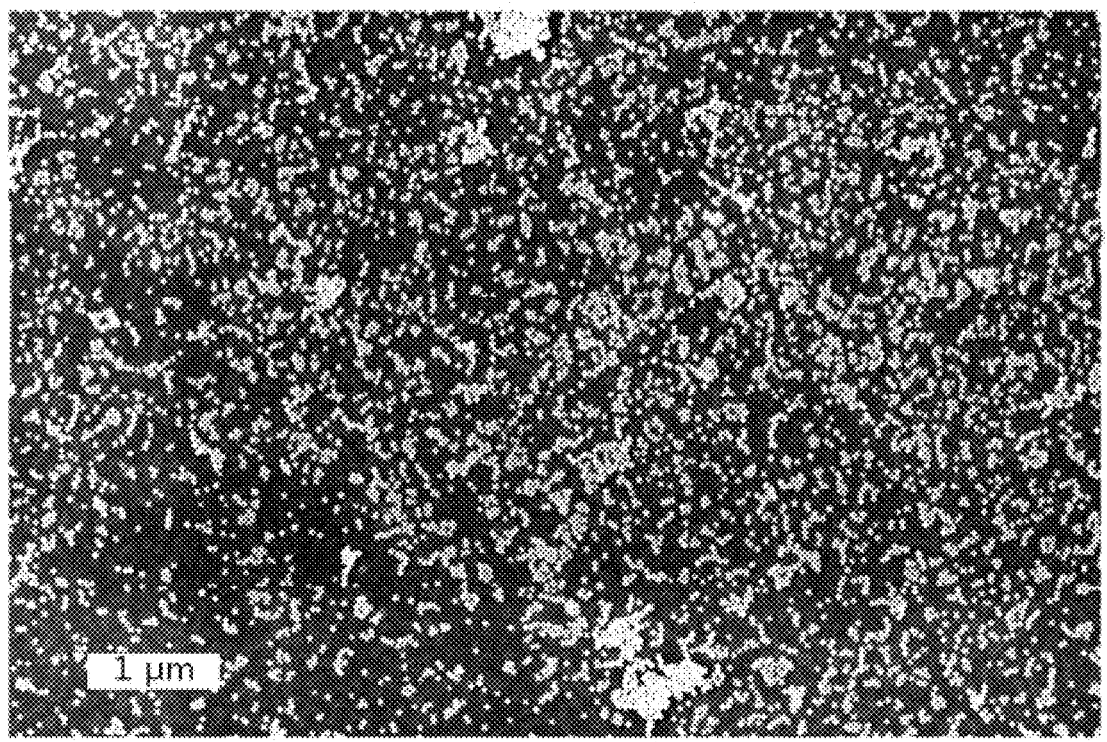
FIG. 3 provides an SEM image of the metasurface assembled according to embodiments and illustrating effects of repeated discreet oligomerization procedures.

In many embodiments, multiple deposition steps may be used to increase the degree of oligomerization on a substrate sample. For example, FIG. 3 depicts a scanning electron microscopy (SEM) image of a sample prepared according to the EHD flow assisted method of the application after four deposition steps. A much greater oligomer density is observed after four deposition than for any sample prepared with two deposition step. However, FIG. 3 also indicates the formation of three-dimensional oligomers, probably due to electrophoresis driving new nanospheres onto the existing oligomers, which might be undesirable for some applications.

Figure 4A:
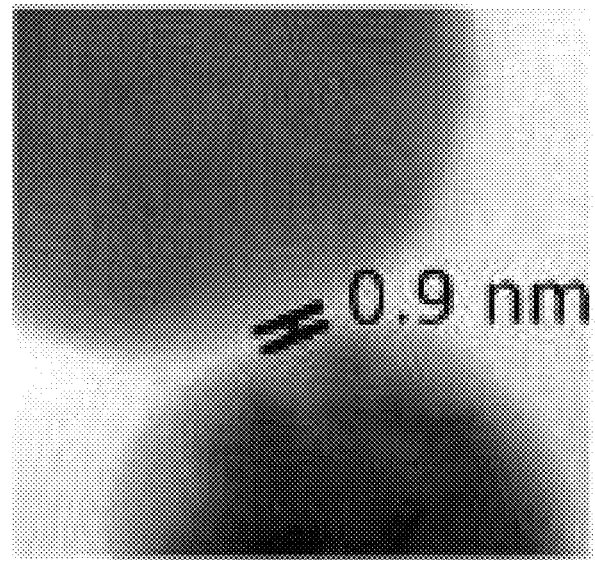
FIG. 4A provides a TEM image of a gap spacing between nanospheres on the metasurface assembled according to embodiments from gold nanospheres of 20 nm diameter, while FIG. 4B provides a TEM image of the same, but assembled according to prior art.
Figure 4B:
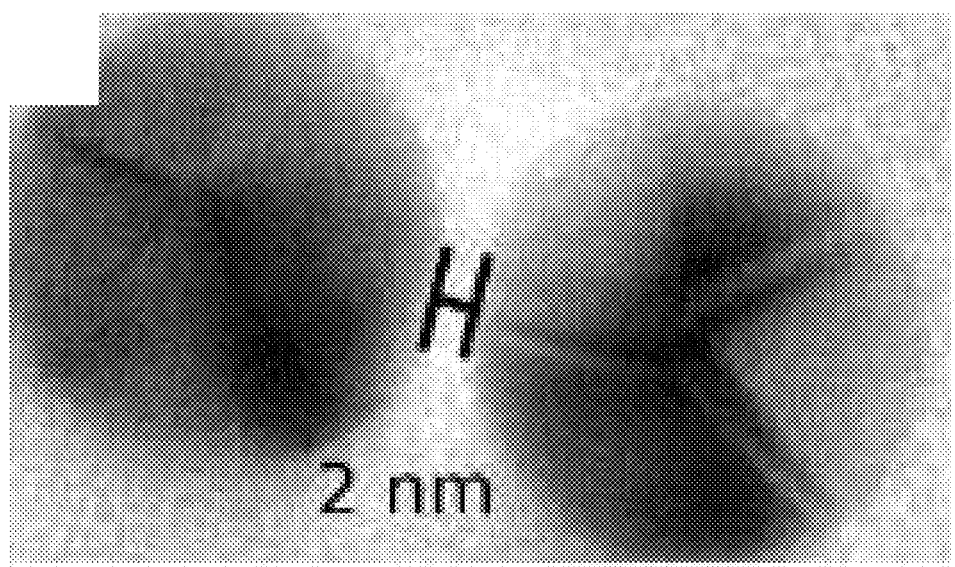

In many embodiments, the gap spacings observed in oligomer depositions performed according to the EHD flow enhanced deposition method of the application are exquisitely small (approaching the quantum tunneling limit) and are among the smallest ever achieved over large deposition area. In many embodiments, EHD flow is critical to achieving such narrow gap spacings between deposited oligomers. For example, incorporation of EHD flow into an otherwise identical deposition procedure reduces the gap spacings in at least half. More specifically, FIGS. 4A and 4B show transmission electron microscopy (TEM) images of a 20 nm Au nanosphere dimer deposited using either EHD flow enhanced deposition method of the application (FIGS. 1A and 4A) or a similarly set-up deposition, which relies solely on the Brownian motion (zero bias-voltage control, FIGS. 1B and 4B). In this experiment, both deposition methods comprised exposing identical polymer template coated Si substrates to identical colloidal solutions of gold nanospheres and relevant reagents, however, in the zero bias-voltage deposition only Brownian motion drives the diffusion of Au nanospheres to randomly collide with the substrate surface. As is seen from the images, zero bias-voltage control deposition results in gap spacings as low as approximately 2 nm (which falls into the 2-7 nm range previously reported for nanospheres assembled without bias), while the EHD flow enhanced methods of the application yields gap spacings of approximately 0.9 nm. Notably, the 2 nm gap spacings observed for the zero bias-voltage control deposition corresponds to the length of two lipoic acid-stabilizing ligands. On the other hand, the ~0.9 nm EPD gap spacings are shorter than the length of two lipoic acid ligands, which indicates the chemical reaction between nanoparticles. While narrow, the gap spacings obtained from the EHD flow enhanced method of the application are still large enough to avoid the depolarization of their dipolar resonances due to quantum tunneling, which has been shown to reduce coupling efficiency when gap spacings are smaller than 0.5 nm. Overall, it should be noted, that while oligomers are produced with both deposition methods, EHD flow has been observed to increase the formation of oligomers and reduce the gap spacings.

Accordingly, in many embodiments, EHD flow generated during the nanoparticle deposition not only brings the nanospheres to the substrate surface, but also in close proximity to each other and facilitates their chemical crosslinking. In turn, in many embodiments, the chemical crosslinking of the nanoparticles to both the assembly guiding template and other nanospheres is critical to retaining the transient structures resulting from the EHD flow, which would disassemble in the absence of thereof.

Oligomer Deposition—Additional Parameters

Figure 5D:
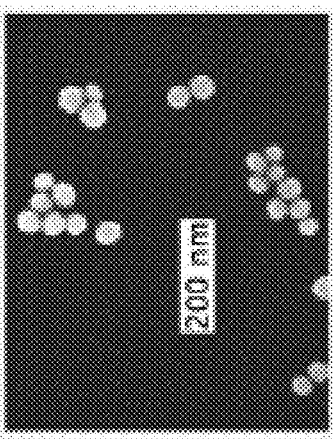
Figure 5C:
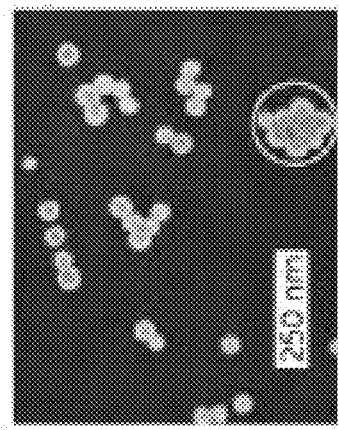
Figure 5B:
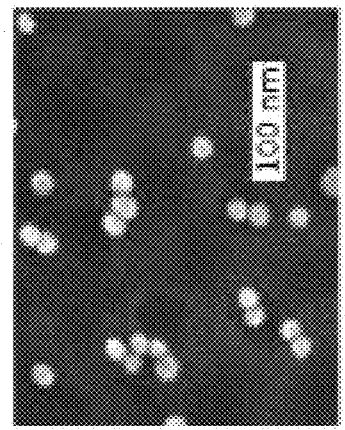
Figure 5F:
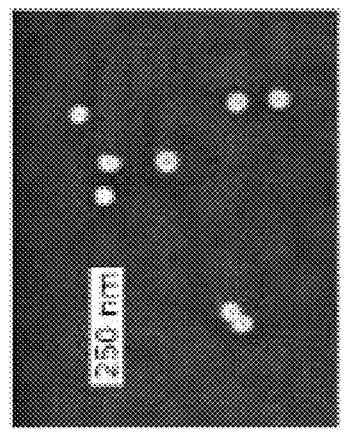
Figure 5E:
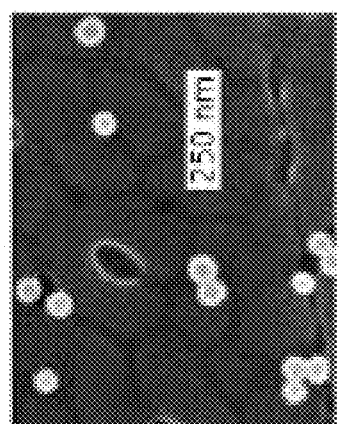

In many embodiments, both the nanosphere size and the temperature of the deposition process influence the gap spacings, areal density, morphology, and oligomerization (i.e. the tendency to form oligomers with an increased number of nanospheres) aspects of the oligomer deposition method of the application, although the temperature effect is secondary to the applied bias. For example, FIG. 5A plots the average oligomer distribution statistics of nanoantenna samples prepared from nanospheres with two different diameters and under different deposition conditions listed in Table 1. Here, percent coverage data is useful for direct comparison of oligomers with different monomer diameter. For reference, it should be noted that the area under the curve for the sample prepared with 40 nm nanospheres and EHD flow assistance is 15% coverage, which corresponds to 54% of the surface area of PMMA domains of deposition template. The relative calculated oligomer densities per micrometer squared are listed in Table 2. In addition, FIGS. 5B through 5F show representative SEM images of the surfaces of the corresponding samples.

TABLE 1

Summary of experimental conditions used in the deposition of the various samples

|  | 20 nm EPD | 40 nm EPD | No Heat | No Voltage | Control |
|---|---|---|---|---|---|
| Nanosphere Diameter | 20 nm | 40 nm | 40 nm | 40 nm | 40 nm |
| Applied Voltage | 1.2 V | 1.2 V | 1.2 V | 0 V | 0 V |
| Temperature | 60° C. | 60° C. | 20° C. | 60° C. | 20° C. |

TABLE 2

Summary of the oligomer number density ratio (%) between dimers and monomers (single nanospheres), trimers and monomers, and quadrumers and monomers. The average number of nearest neighbors for a given nanoparticle is listed in parenthesis.

|  | EPD 20 nm | EPD 40 nm | No Heat | No Voltage | Control |
|---|---|---|---|---|---|
| Total Coverage | 10.4% (1.7% σ) | 14.6% (1.5% σ) | 3.7% (0.2% σ) | 2.5% (0.9% σ) | 1.1% (0.3% σ) |
| Dimer:Monomer Ratio | 13.2% (1.6% σ) | 36.7% (4.9% σ) | 62.7% (19.7% σ) | 11.7% (1.7% σ) | 12.7% (3.2% σ) |
| Trimer:Monomer Ratio | 5.9% (0.9% σ) | 29.2% (3.7% σ) | 55.0% (18.0% σ) | 5.7% (1.2% σ) | 4.6% (2.6% σ) |
| Quadrumer:Monomer Ratio | 2.8% (0.7% σ) | 20.3% (2.8% σ) | 40.2% (14.3% σ) | 3.3% (0.9% σ) | 2.0% (1.5% σ) |
| Average Number of Nearest Neighbors | 1.21 | 2.06 | 2.23 | 1.19 | 0.66 |

Overall, the experimental results with different nanosphere radii further elucidate physical and chemical mechanisms affecting oligomerization in accordance with embodiments. Specifically, increasing the diameter of the colloidal nanosphere leads to substantial differences in oligomerization since EHD forces are size dependent (the driving force increases with size). For one, in many embodiments, the surface coverage of the oligomer deposition method of the application increases with increasing nanospheres radii. More specifically, FIG. 5A and Table 2, show a larger area under the oligomer distribution curve for the '40 nm EPD' samples than for the '20 nm EPD' nanosphere samples—both fabricated using EPD-assisted method of the application—indicating a greater tendency for 40 nm metal nanospheres to bind to the templated surface. One factor favoring the higher efficiency of chemical attachment to the template surface is the lower curvature of 40 nm nanospheres than 20 nm nanospheres, which relatively increases the number of O-acylisourea groups in contact with the amine-functionalized PMMA template domains during a nanosphere-template surface collision event.

In addition, in many embodiments, the density of the surface coverage of the oligomer deposition method of the application also increases with increasing nanosphere radii. More specifically, as tabulated in Table 2, the '40 nm EPD' sample exhibits nearly double the number of nearest neighbors to a given particle (2.06) as compared to the '20 nm EPD' sample (1.21). These figures of merit provide information on the strength of the driving force to form oligomers on a sample, where 0 would be a monomer, and 6 would be a perfect hexagonally close packed lattice. A low pH near the working electrode is expected to reduce the electric double layer, promoting the reversible aggregation of lipoic acid-functionalized nanoparticles near the substrate surface. Yet, if one assumes that the aggregation of Au nanospheres into oligomers is driven by Van der Waal's forces overcoming electric double layer forces, as described by Derjaguin Landau Verwey Overbeek (DLVO) theory, one would expect somewhat greater aggregation for the 20 nm nanospheres which have a smaller zeta potential as used here. (See, e.g., Israelachvili, J. N. Intermolecular and Surface Forces: Revised Third Edition. (Academic Press, 2011), the disclosure of which is incorporated herein by reference.) However, this expectation is not consistent with the data obtained for the EHD-assisted method of the application, wherein the 40 nm nanosphere samples exhibit a higher degree of oligomerization (as confirmed by the oligomer-to-monomer ratios and average nearest neighbor counts listed in Table 2). Although not to be bound by theory, these results may indicate that in methods in accordance with embodiments, the thinning of the double layer is not a strong driving force in the nanoparticle oligomerization and that the oligomerization is, thus, driven by a EHD flow.

Furthermore, 3-dimensional aggregates and large fractal structured aggregates, which are characteristic of aggregation in solution due to reduced electrostatic repulsion, are not commonly observed in SEM images of samples prepared according to the methods of the application. In addition, the observation of a large fraction of monomers in the 'No Voltage' and 'Control' samples, compared to '40 nm EPD' and 'No Heat' samples exhibiting a preference for oligomerization, indicates that standard carbodiimide crosslinking is not strongly driving oligomer formation. More specifically, if carbodiimide crosslinking were the main driving force of nanosphere assembly into oligomers, the deposition would be expected to yield a large number of substrate surface monomers, with a monotonically decreasing occurrence frequency of larger oligomers, since the electrostatic repulsion between nanospheres would favor monomer formation. However, while this trend was observed for deposition of 20 nm nanosphere samples, it did not hold for 40 nm nanospheres. Accordingly, in many embodiments EHD driving forces increasingly scale as nanoparticle radii increase, and, as such, the EHD flow may be used in the templated formation of oligomers beyond providing a driving force to bring nanospheres toward the surface via electrophoretic sedimentation. In many embodiments, the radii of nanoparticles chosen for the assembly of the metasurfaces of the embodiments is between 20 and 100 nm. In many such embodiments, the nanoparticles have a 40 nm radius.

In many embodiments, the oligomer deposition procedures are conducted at an elevated processing temperature of 60° C. Therefore, experiments were conducted to decouple the role of temperature in the deposition process. To this end, 40 nm metal nanospheres were deposited on the templated surface of the method of the application under the following experimental parameter variations (listed in Table 1): zero bias-voltage at T=60° C. ('No Voltage'), room temperature at an external bias of V=1.2V ('No Heat'), and zero bias-voltage and room temperature ('Control'). Unsurprisingly, the oligomer distribution statistics of the 'Control' sample (FIG. 5A, Table 2) exhibited few nanospheres on the surface. In the absence of any bias, the deposition relies solely on Brownian motion, which is expectedly reduced at the lower temperature, leading to fewer collisions between nanospheres and the deposition template and, thereby, lower surface coverage. The measured statistics for the 'Control' sample also showed virtually no oligomers over size 4. However, comparison of the surface coverage of the 'No Voltage' and 'No Heat' samples (FIGS. 5A, 5D, 5E) shows that an applied bias has an even greater impact on surface coverage than temperature. Notably, the oligomer to monomer ratios of the 'No Heat' samples are the largest, albeit at the expense of uniformity, as measured by the standard deviation. Overall, the greater degree of oligomerization is clearly due to the bias, through either EHD flow or electrophoretic sedimentation.

Figure 6:
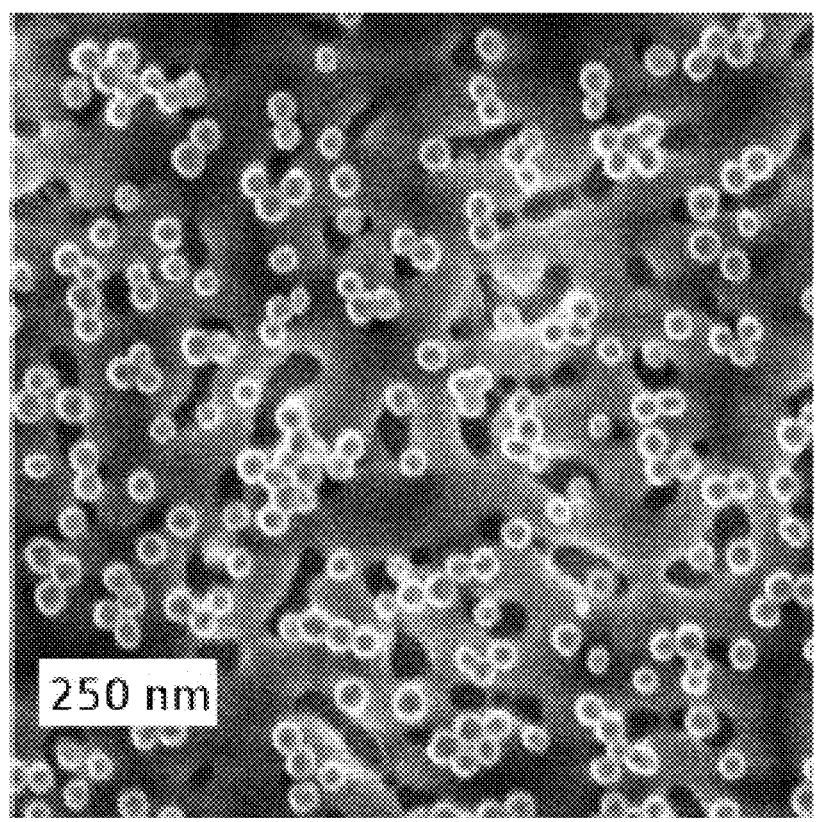
FIG. 6 provides a SEM image of the metasurface assembled according to embodiments and illustrating the positioning of gold nanospheres relevantly to the underlying diblock polymeric template.

In addition, it is observed that oligomers formed with a bias voltage according to the method of the application are not necessarily aligned with the underlying amine functionalized PMMA domains of the deposition template. For example, FIG. 6 depicts 40 nm Au nanosphere oligomers assembled according to the method of the application. In this image, the underlying template visible under the imaging conditions. Specifically, PMMA template domains can be observed in SEM images taken under lower current and accelerating voltage, wherein they appear darker with bright edges due to topography changes during the ethylenediamine functionalization step. Furthermore, FIG. 6 shows that nanospheres within the oligomers are observed on the amine-functionalized PMMA domains (dark with bright borders) and on PS regions. Similarly, 'No Heat' samples are also observed to have oligomerized nanospheres directly over the chemically inert PS domains of the deposition template. Furthermore, in both cases, the PS domains adjacent oligomerized nanospheres are not directly attached to the template, but to other nanospheres that are situated over PMMA (see circled area in FIG. 5C). In contrast, the nanospheres in the 'No Voltage' and 'Control' samples are observed to be positioned only directly above PMMA domains, as expected for carbodiimide crosslinking attachment of nanospheres to the template's amine functionalities. This observation, together with the observation that temperature has a profound effect on oligomerization (as shown by the comparison between the 'No Heat' and the '40 nm EPD' samples), demonstrates that, in many embodiments the temperature parameter may be adjusted to optimize the oligomerization of nanospheres during the deposition process of the application. Accordingly, in many embodiments, the temperature is adjusted between just below room temperature of approximately 10° C. to up to 80° C. More specifically, in some embodiments, wherein the rate of the chemical reactions of the deposition is temperature dependent, the deposition temperatures below 10° C. will slow such chemical reactions to a halt. In many embodiments, the deposition temperatures above 80° C. may lead to uncontrollable aggregation of the nanospheres.

The importance of EHD forces beyond nanoparticle sedimentation is furthermore confirmed by the apparent effects of nanosphere radii on the deposition results of the method of the application. Specifically, on one hand, the greater frequency of monomers on the '20 nm EPD' sample surfaces, as compared to all other samples, appears to be an effect of electrophoretic sedimentation, as the smaller radii reduces Stokes drag, which, in turn, increases sedimentation. On the other hand, the samples of larger 40 nm nanospheres appear to behave differently in deposition with and without applied bias voltage. Specifically, applying a bias of 1.2V at room temperature ('No Heat') leads to over a 2.5-fold reduction in the number of monomers over the Control sample. This observation indicates that in the case of the 40 nm particles the EHD flow is more impactful on the oligomerization than on electrosedimentation. Overall, the obtained data is consistent with the fact that EHD driving forces incorporated into the methods of the instant application scale with nanosphere radii.

Figure 7A:
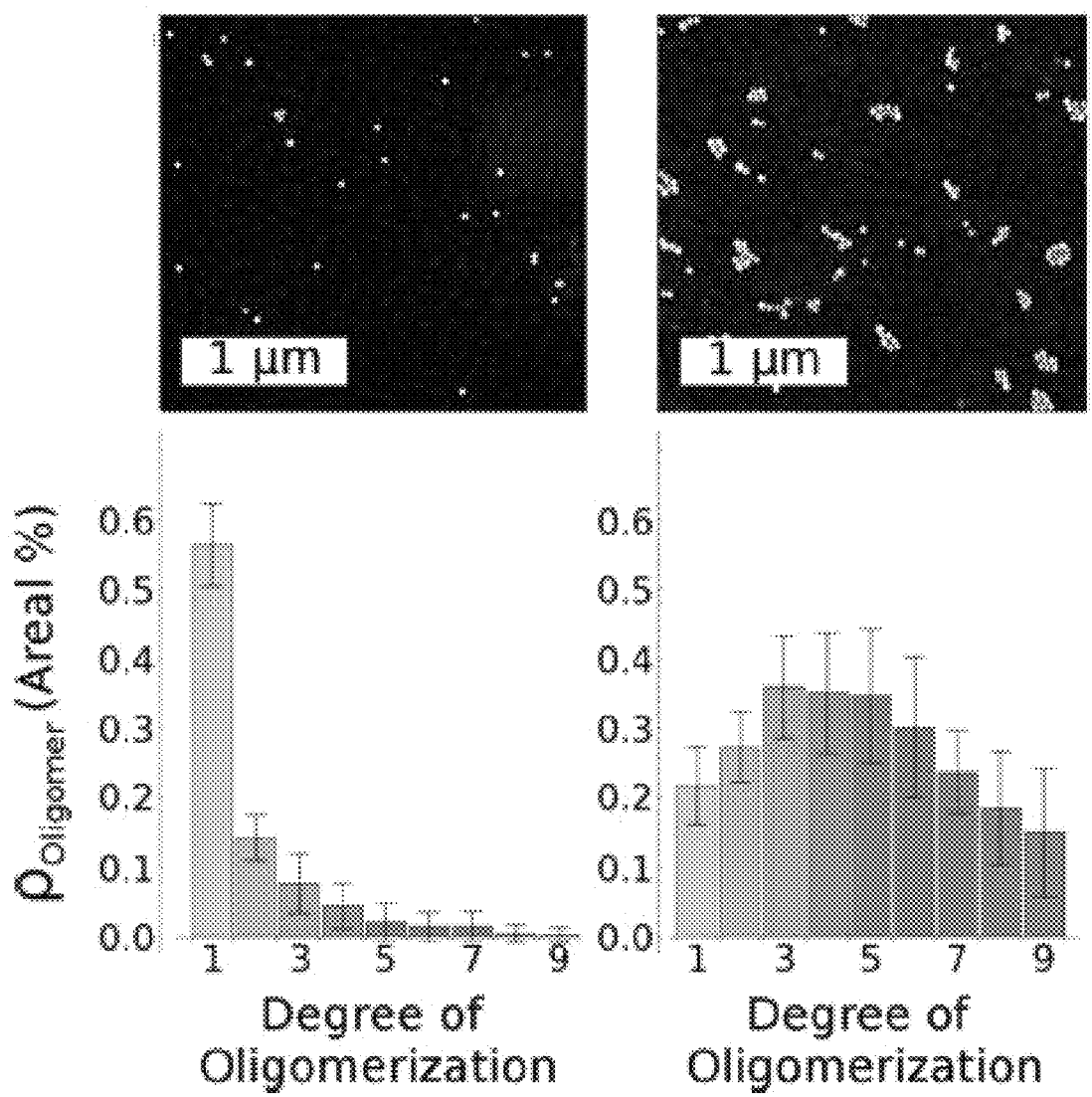
FIGS. 7A through 7C illustrate data analysis collected from experiments probing various metasurface fabrication parameters according to embodiments with SEM images and statistical data.
Figure 7B:
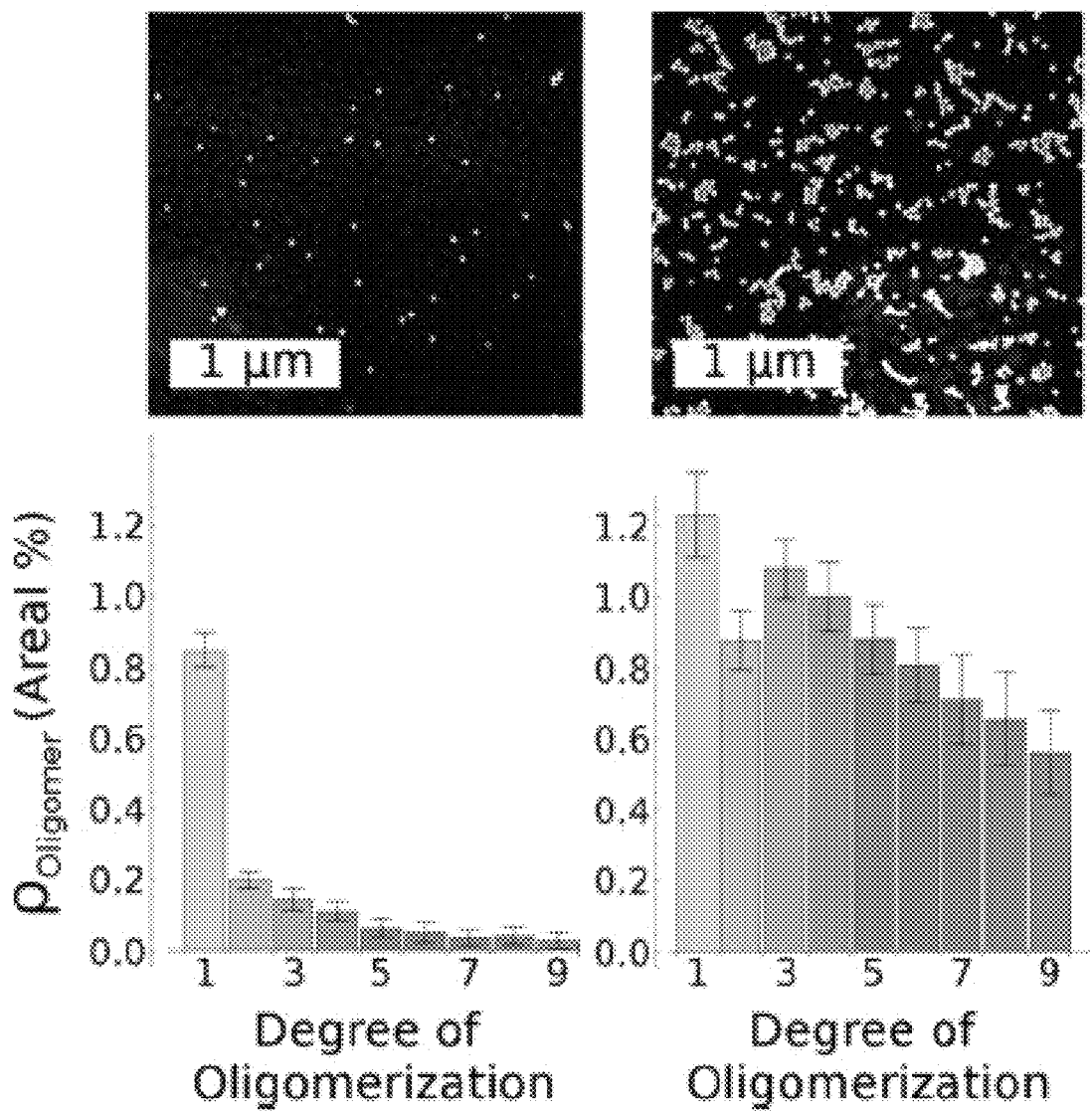
Figure 7C:
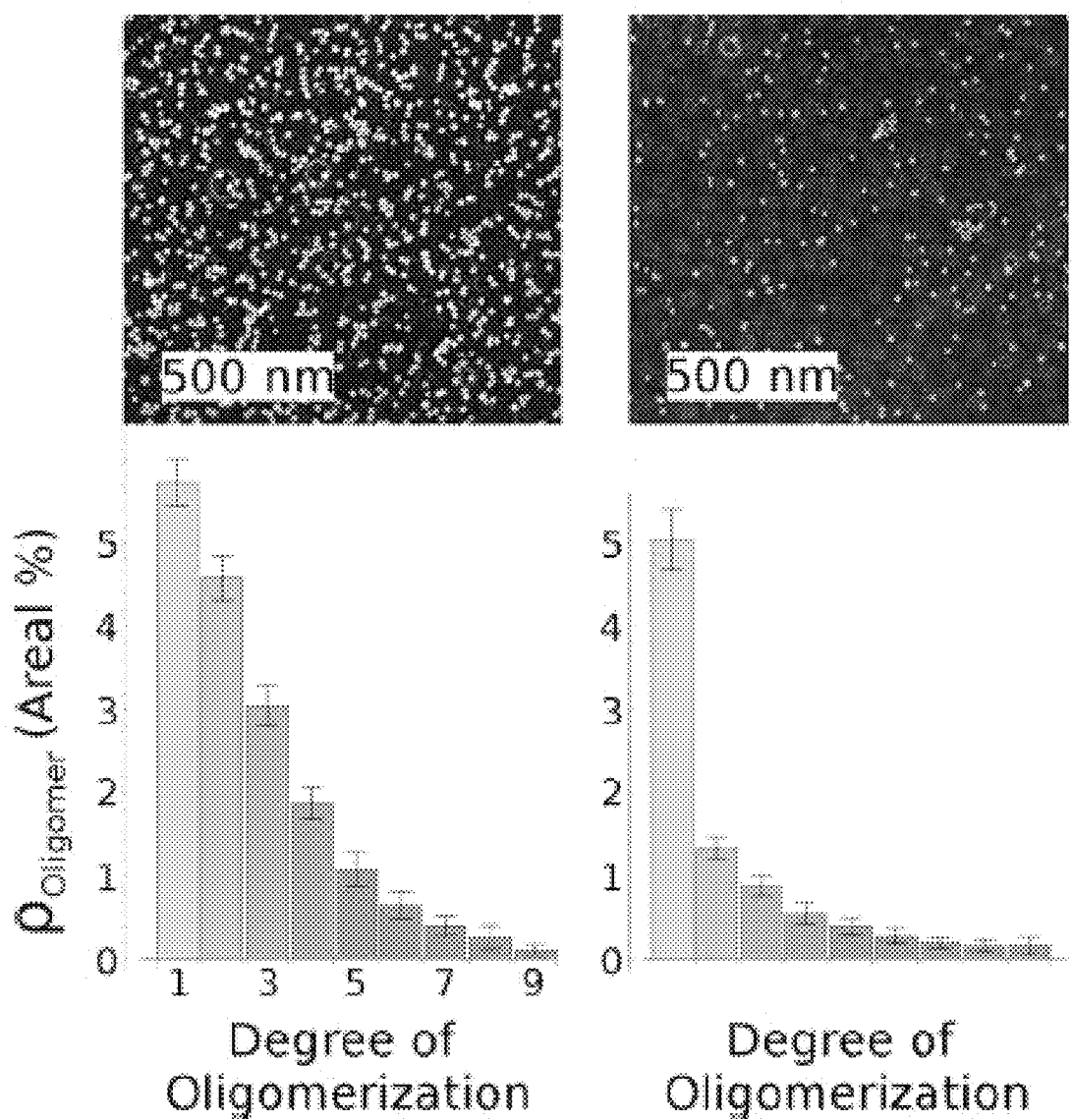

FIGS. 7A through 7C illustrate additional experiments with varying nanoparticle diameter and deposition conditions conducted to further investigate the driving forces behind the assembly method of the embodiments. Specifically, these experiments further probe how EHD flow induced anhydride cross-linking of the method of the application affects density and geometry of oligomers deposited on substrates. First, oligomer formation from 40 nm gold nanospheres on substrates assembled without applied bias and without heating (i.e. room temperature assembly) was examined. FIG. 7A (top row) depicts representative SEM images of substrate surfaces assembled at room temperature without (left side) and with (right side) an applied bias. Here, it is important to consider that in the absence of applied bias, the nanosphere assembly on the template is driven by Brownian motion, which propels the nanospheres to randomly collide with the substrate surface. Such collisions, in turn, can result in a reaction between an O-acylisourea on the nanosphere and an amine functionality on the surface, covalently binding nanospheres to the PMMA domains via an amide bond. In this scenario, an oligomer is formed when another nanosphere reacts with the PMMA surface near a monomer. The tendency to grow beyond a monomer is referred to as oligomerization. Oligomer configuration (measured as number of nearest neighbors) and oligomerization are examined by measuring percent coverage of various oligomers (monomer, dimer, trimer, etc.) on the substrates' surfaces. Percent coverage statistics are determined via analysis of SEM images over 25 adjacent regions with dimensions 8.0 μm×5.5 μm as detailed in the Supporting Information below. The respective coverage statistic data are shown in the bottom row of FIG. 7A. Unsurprisingly, the "no-bias" substrates exhibit a steep decrease in percent coverage beyond a monomer, due to electrostatic repulsion between nanospheres, and a monotonic decrease in percent coverage beyond a dimer.

Comparison of statistics in FIG. 7A shows a 336% increase in nanosphere coverage for the sample assembled with applied bias compared to the no-bias sample. The increase in coverage can partially be attributed to electrophoretic sedimentation due to the applied bias. However, careful examination of data also shows dramatically increased oligomerization, few monomers, and many close-packed oligomers—a signature of EHD flow driven assembly—on the EHD-assisted assembly substrate. More specifically, the average number of nearest neighbors per particle increases from 0.66 to 2.2 (where 0 is an isolated particle and 6 is a 2D hexagonally close-packed lattice) from the no-bias to biased substrate. If electrophoresis were the only driving force, surfaces would exhibit a monotonically decreasing oligomerization distribution similar to the no-bias substrate. Instead, the biased substrate has the distribution is centered around quadrumers (FIG. 7A bottom right), and anhydride linking induced by EHD flow leads to over a 2.5-fold reduction in the number of monomers with respect to the no-bias substrate. This observation is consistent with the seeded growth assembly mechanism where seed monomers are consumed when they oligomerize via anhydride attachment with nanospheres in a colloid due to the presence of an applied bias driving EHD flow.

It is also important to consider how Brownian motion competes with EHD flow during oligomer formation. The effect of Brownian motion can be evaluated by examining oligomer configuration statistics after assembly when the colloid is heated to 60° C. during deposition. To this end, FIG. 7B (top row) depicts representative SEM images of substrate surfaces assembled at 60° C. without (left side) and with (right side) an applied bias. Without voltage (FIG. 7B, left), a nearly 2-fold increase is observed in the number of nanospheres attached to the surface in comparison to no-voltage room temperature deposition (FIG. 7A, left). With voltage (FIG. 7B, right), a dramatically increased density of oligomers is observed with respect to all other assembly conditions. The total nanosphere surface coverage for the 60° C. voltage-assisted assembly substrate is 15%, while the surface coverage for the room temperature voltage-assisted assembly substrate is only 3.7% (FIG. 7A, right). The data at the bottom of FIG. 7B depict the oligomerization statistics obtained from the no-bias and bias-assisted assembly substrates to understand the more complex behavior at elevated temperature. First, Brownian motion is expected to increase the number of nanosphere collisions with the surface, increasing the number of monomer seeds. Monomers indeed dominate in frequency on the 60° C. no-bias assembly substrate, as observed in the SEM image in FIG. 7B, top left, and corresponding statistics in FIG. 7B, bottom left. The bias-assisted substrate deposited at 60° C. shows a reduced degree of oligomerization (FIG. 7B, bottom right) when compared to the room temperature biased deposition (FIG. 7A, bottom right). In addition, a slight shift to smaller oligomers on average is observed when deposition occurs at 60° C. versus room temperature, e.g. trimers are observed with the higher frequency over quadrumers. However, oligomers are still observed to be close packed (with an average of 2.06 nearest neighbors per particle) in assembly at 60° C., indicating that EHD is still a major long-range driving force. These data, indicate that EHD flow competes with Brownian motion, yet Brownian motion does not completely overwhelm EHD flow in determining oligomer morphology during assembly of nanospheres of 40 nm diameter. Indeed, in many embodiments, the increase in temperature is a means for limiting the size of oligomers and increasing their density on the surface by increasing the number of seed monomers on the template surface. In fact, for many applications, for example SERS sensors, the higher surface coverage of the substrates resulting from the deposition method of the application conducted at elevated temperature is desirable for high hotspot density. However, in some embodiments, precaution should be taken to not overheat the deposition process, as the deposition temperatures above 80° C. may lead to uncontrollable aggregation of the nanospheres. Moreover, in many embodiments, the increased oligomer density and reduced degree of oligomerization from a slight increase in deposition temperature synergistically improves optical response uniformity of the substrates assembled according to the method of the application. Accordingly, in many embodiments, the deposition temperature can be raised to as high as 80° C.

The relative contributions of EHD flow, Brownian motion, and electrophoretic sedimentation can be further elucidated by comparing oligomerization of particles with different dimensions. While long-range forces associated with EHD flow increase with increasing particle diameter, and those associated with Brownian motion decrease with increasing particle diameter, electrophoretic mobility is primarily dependent on zeta potential. FIG. 7C shows representative SEM images (top row) and oligomerization statistics (bottom row) for samples assembled from 20 nm diameter Au nanosphere colloids at room-temperature (left) and at 60° C. (right). All other deposition parameters are identical to the 40 nm diameter Au nanosphere depositions reported in FIGS. 7A and 7B. Oligomerization statistics in FIG. 7C (bottom row), are determined from 25 SEM images with dimensions of 4.0 µm×2.7 µm. As seen from FIG. 7C (left) the room-temperature 20 nm nanoparticle sample has significantly greater total surface coverage than its 40 nm diameter counterpart (FIG. 7A, left), 17% compared to 3.7%, likely due to the reduced Stokes drag on the smaller particles. FIG. 7C (top right) shows that increasing deposition temperature to 60° C. greatly reduces EHD flow induced oligomerization, likely due to the significant increase of the average velocity of the 20 nm particles at the higher temperature. These data show that increased Brownian motion competes with EHD flow, and that the faster moving nanospheres have a reduced probability of being entrained by EHD flow. Overall, the 20 nm diameter substrates appear to be significantly less oligomerized than the 40 nm substrates, which is consistent with the fact that EHD flow force density scales with particle size. As such, in many embodiments in which EHD flow is an important driving force for colloidal assembly nanospheres are provided having a diameter in the range of 20 to 100 nm, consistent with observations using optoelectrokinetic flows.

Together, all the data presented in FIGS. 5A through 7C and the related discussion presented above provide additional insight into the combined roles of EHD flow, carbodiimide crosslinking (including template binding), nanosphere radii, deposition temperature and other deposition process variables in driving the assembly and oligomerization of the nanospheres when deposited according to the method of the application. Accordingly, without being bound by any theory, the analysis of the data presented in this disclosure suggests the following deposition and oligomerization mechanism for the EHD flow-assisted deposition method in accordance with embodiments. Two-dimensional growth of metal nanosphere oligomers over areas as large as 1 cm² occurs via a two-step seeded growth method where oligomer growth from functionalized metal nanosphere seeds is driven by electrohydrodynamic (EHD) flow. After growth, oligomers are stabilized by chemical cross-linking that also provides uniform gap spacings. The process of oligomer growth and cross-linking, in accordance with embodiments, is depicted in FIGS. 1A, 1C, and 2, and the mechanism is as follows: (1) Electrophoretic sedimentation guides functionalized metal nanospheres toward a doped working electrode coated with an assembly assisting template. Next, designer cross-linking chemistry covalently binds these nanosphere seeds on complimentary functionalized template regions. The template is chosen to distribute monomer nanoparticle seeds evenly over the entire substrate surface. (2) The presence of bound metal nanosphere monomer seeds on the working electrode promotes oligomer growth by generating EHD flow. EHD flow then entrains nearby nanospheres, extending approximately four particle diameters, dragging them toward the source of the perturbation (the nanoparticle seed) in the plane of the electrode, leading to the growth of oligomers. At least a second growth step with a fresh nanosphere solution is used to further grow oligomers. (3) The cross-linking chemistry stabilizes oligomers after formation—as the oligomers formed by EHD flow are transient, their formations will dissolve back into the bulk solution upon removal of the voltage without a strong attractive force with the surface. Deposition steps may be repeated to continue oligomer growth, as desired. In addition, the EHD flow force appears to increase with increasing nanoparticle size. Finally, temperature of the deposition process can also be adjusted to manipulate the desired oligomerization and/or substrate surface coverage. Overall, incorporating the EHD flow into the metal nanoparticle deposition method of the embodiments has profound implications on the uniformity of the produced metasurface gap spacings and their optical properties.

EXAMPLARY EMBODIMENTS

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., s or sec, second(s); min, minute(s); h or hr, hour(s); and the like.

Example 1

Molecular Dynamics Simulations to Probe the Assembly Mechanism

Figure 8A:
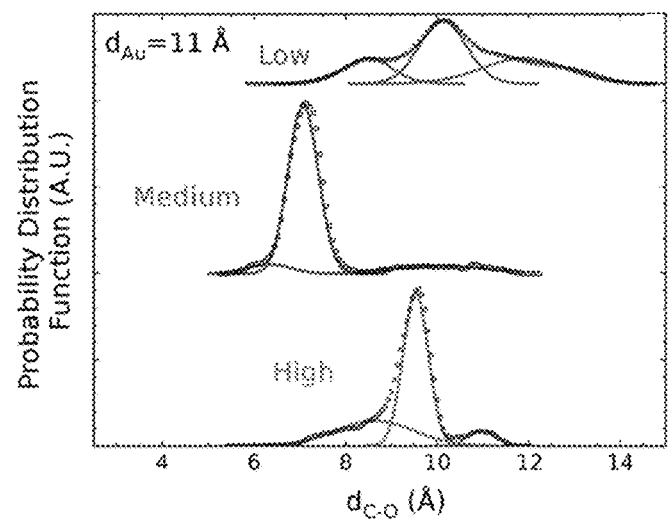
FIGS. 8A through 8D illustrate molecular dynamic simulation analysis of the driving forces behind chemical reactions in the metasurface fabrication according to embodiments.
Figure 8B:
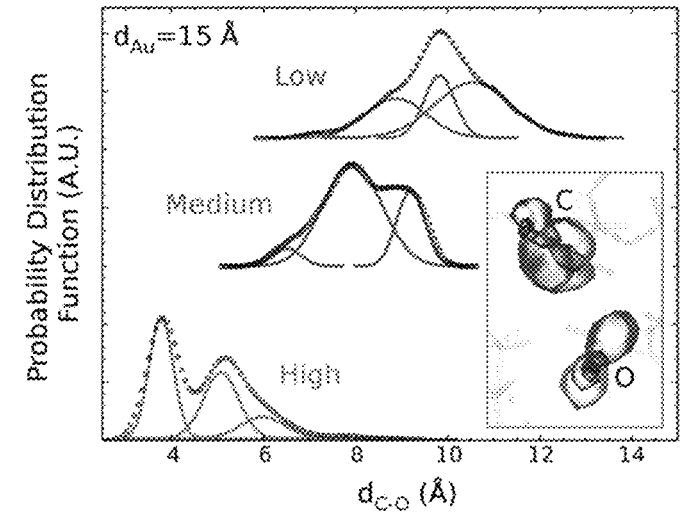
Figure 8C:
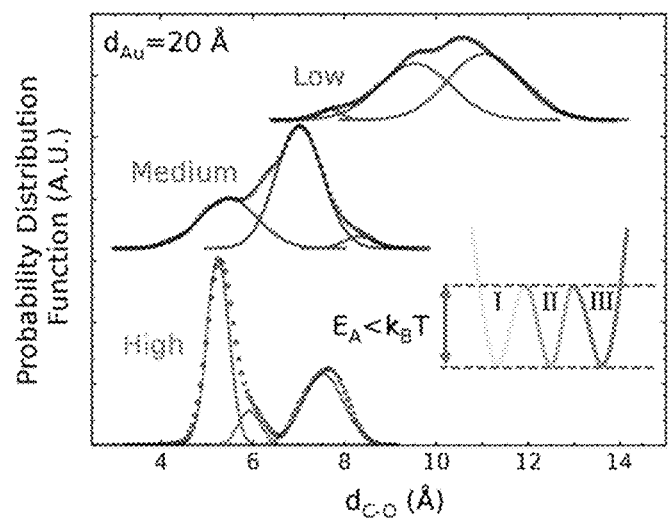
Figure 8D:
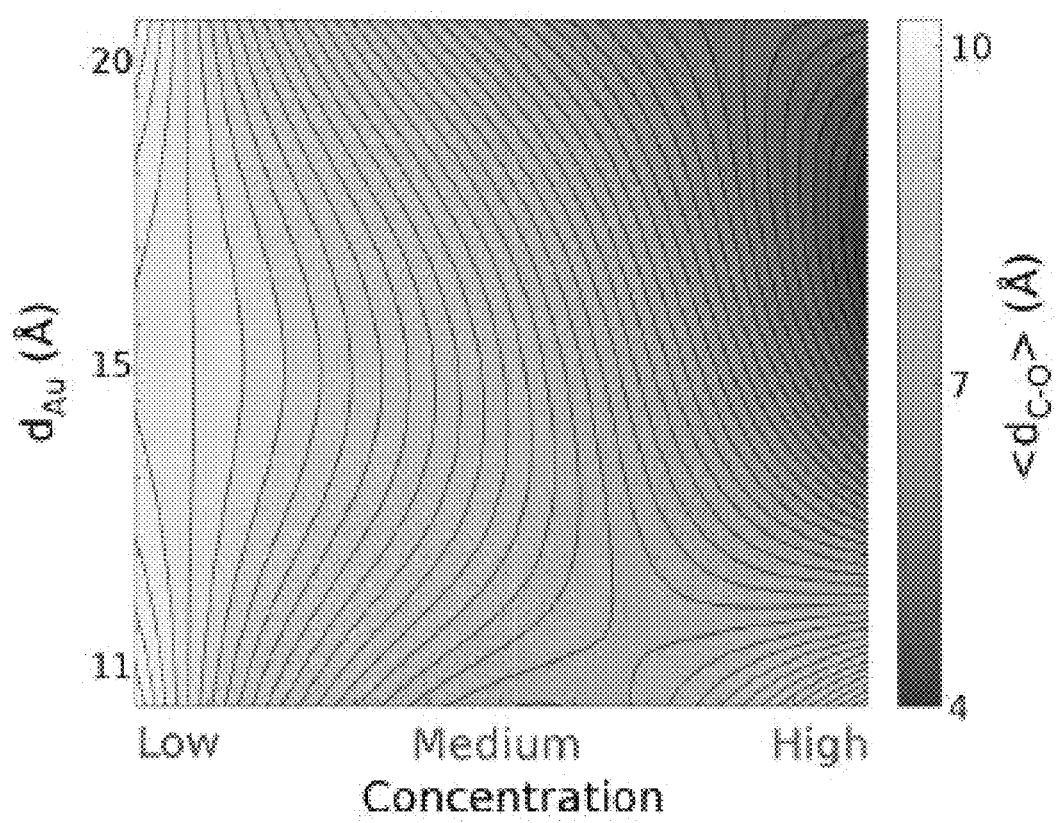

Reactive molecular dynamics (MD) simulations illuminate the origin of the EHD-driven anhydride cross-linking. The stability of Au nanospheres in solution with a carbodiimide cross-linker indicates that the anhydride pathway is a rare event. Here, this hypothesis is examined by analyzing the probability distribution function of the distance between the reactive carbon atom in O-acylisourea (OA) and the deprotonated oxygen atom in lipoic acid (LA) ($d_{C-O}$) using the transferable ReaxFF potential. The exact concentration of LA and OA ligands on the surface may vary from nanosphere to nanosphere, so three concentrations are analyzed: one OA to one LA (low), one OA to four LA (medium), and two OA to four LA (high) concentrations. The concentrations investigated are in the range of LA ligands observed on the surface of gold nanospheres. In simulations, ligands are connected to opposing faces of an Au (111) slab at 11, 15, and 20 Å nanogap separations, $d_{Au}$. Simulation parameters are further detailed in the Materials and Methods section. FIGS. 8A-8C (dotted curves) depict the distributions of $d_{C-O}$ in the various cases, with FIG. 8D providing an interpolated contour map of the relationship between $d_{Au}$, $d_{C-O}$, and ligand concentration. Two features of the nanogap chemistry are salient: (1) 17 Å corresponds to fully extended LA and OA ligands and is thus the minimum $d_{Au}$ for the reaction to occur. This minimum distance for reaction is not observed in TEM images obtained from control samples assembled without EHD flow. (2) Regardless of ligand concentration and $d_{Au}$, the proximity required for reaction ($d_{C-O}$=2.9 Å) is at least 4 standard deviations from the mean $d_{C-O}$. These results indicate that EHD flow is necessary for maintaining close proximity between nanoparticles in timeframes reasonable for reaction.

Interesting ligand dynamics also emerge from the MD study, indicating entropy's role in this reaction. Gaussian mixture analysis of $d_{C-O}$ trajectory, depicted in FIGS. 8A-8C as solid curves, identifies three normal distributions regardless of concentration and nanogap distance. The inset of FIG. 8B visualizes these trajectory states for the carbon (C) and oxygen (O) molecules in the configuration space. These three states are separated by energy barriers comparable to thermal fluctuations, $k_BT$, schematically illustrated in FIG. 8C's inset. MD simulations probe these three degenerate states via a diffusive mechanism, which is entropic in nature. It is found that the average $d_{C-O}$ decreases with increasing concentration except for the case of high concentration at small nanogap distances, $d_{Au}$=11 Å. The latter is strongly affected by the presence of large steric forces between OA and LA groups that ultimately hinder the mobility of reaction sites in the nanogap. The minimum average proximity, $d_{C-O}$=4.1±0.3 Å, occurs at high concentration, when the nanogap separation is 15 Å. Yet, this distance is greater than the proximity required for reaction, 2.9 Å, and only the tail end of the probability distribution function samples this space. Therefore, it can be concluded that entropic effects play a critical role in bringing reactive cores in proximity to each other, an event that occurs rarely as a result of competition with steric effects. Furthermore, our results confirm that the probability of bringing reactive groups in proximity to one another is dependent on both the concentration and nanogap size, $P_{entropy}$=$P_{entropy}$(C, $d_{Au}$), hypothesized in previous work to drive anhydride bond formation via carbodiimide crosslinking.

Figure 9:
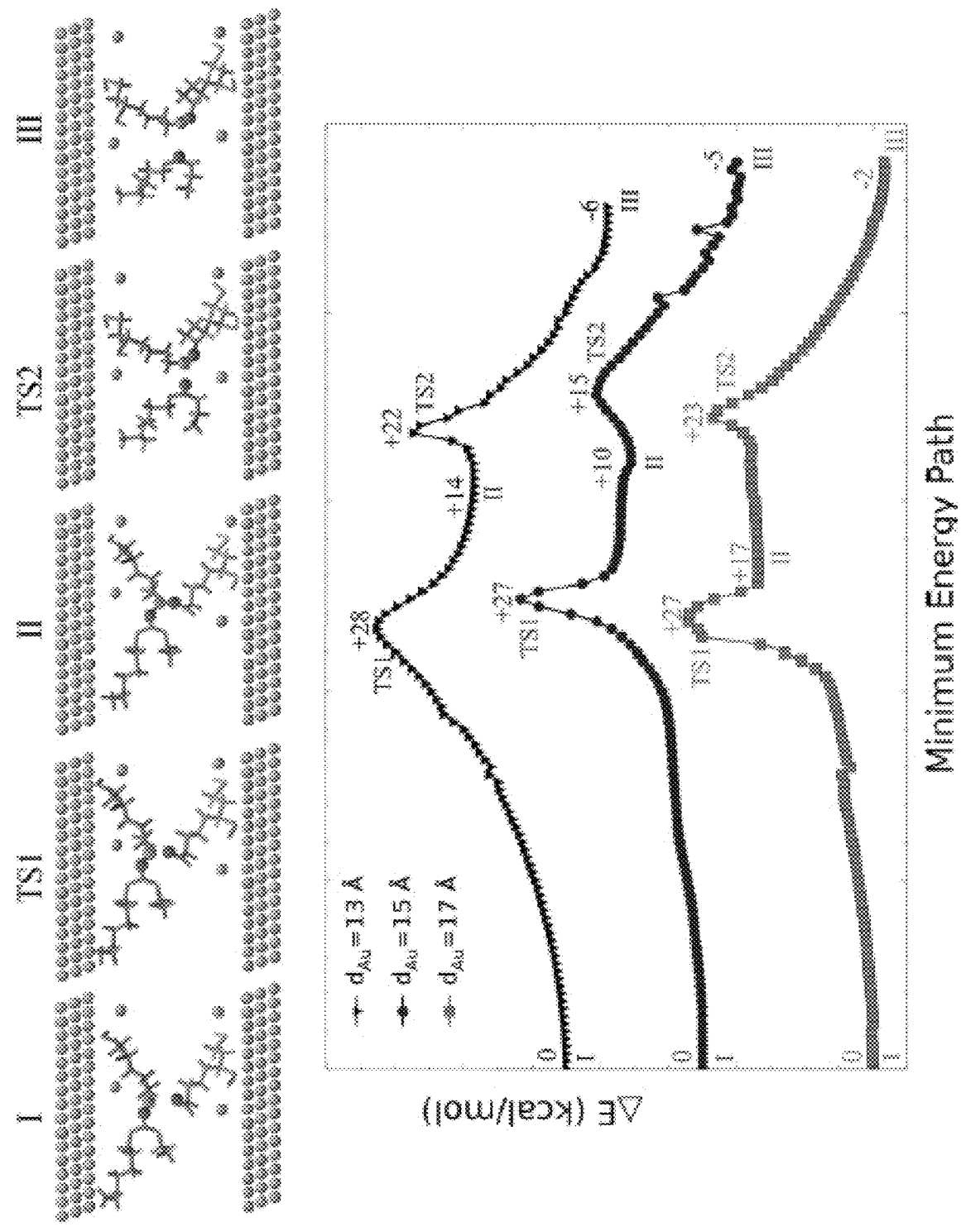
FIG. 9 illustrates molecular dynamic simulation analysis of the driving forces behind the chemical reactions in the metasurface fabrication according to embodiments.

With the role of entropy understood, it is possible to turn to consider enthalpic processes. Observation of rare chemical reactions with the MD framework is facilitated via a harmonic bias potential that favors small $d_{C-O}$. At high temperatures anhydride formation is indeed observed, consistent with the premise that EHD flow is necessary to facilitate this reaction. A nudged elastic band (NEB) technique is employed to probe the minimum energy path (MEP), given low $d_{C-O}$. FIG. 9 depicts the MEP of low concentration LA-OA (I) reaction to form an anhydride (III), exhibiting two enthalpic reaction barriers (TS1 and TS2) and a metastable intermediate complex (II) at different $d_{Au}$. The configurations at the top of FIG. 9 provide a schematic representation of successive reaction stages extracted from NEB simulations. The enthalpy of reaction is found to vary between −2 and −6 kcal/mol, indicating an exothermic process. The TS1 activation energy barrier is roughly 27 kcal/mol (~45 $k_BT$ at ambient conditions) irrespective of $d_{Au}$. This activation energy is comparable to that of imine carbons on polycarbodiimides measured in $^{13}C$ CP/MAS NMR spectroscopy. The intermediate complex further dissociates to yield anhydride with a TS2 activation energy barrier estimated at 5-8 kcal/mol. NEB calculations indicate that transition through TS1 is the rate-controlling step in the anhydride formation. This enthalpic rate is controlled neither by the concentration nor by the nanogap size. Therefore, the probability of such enthalpic reaction, in terms of external variables, is just a function of temperature, $P_{enthalpy}$=$P_{enthalpy}$(T), in our system. Thus, the probability of reaction $P_{Reaction}$=$P_{entropy}$(C, $d_{Au}$)×$P_{enthalpy}$(T)×$P_{Collision}$ is tuned on the nanosphere assembly surface by modifying $P_{Collision}$ via EHD flow.

In summary, atomistic simulations discussed here help elucidate parameters affecting assembly of the metasurfaces of the embodiments. In particular, these studies further agree with the notion that the EHD flow is a factor in the assembly process of the embodiments, as this force increases the probability of nanosphere-nanosphere collisions, which, ultimately, result in crosslinking/bridging bond formation between nanospheres, and helps drive oligomerization process forward.

Example 2

Oligomer Optical Properties

Figure 10A:
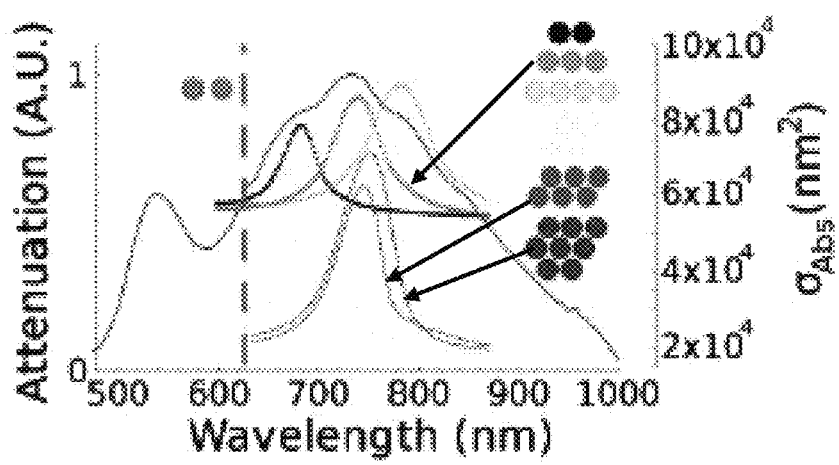
FIGS. 10A through 10C illustrate UV-Vis (optical) analysis of the optical properties of the metasurface fabrication according to embodiments and comparison to prior art (FIG. 10B).
Figure 10B:
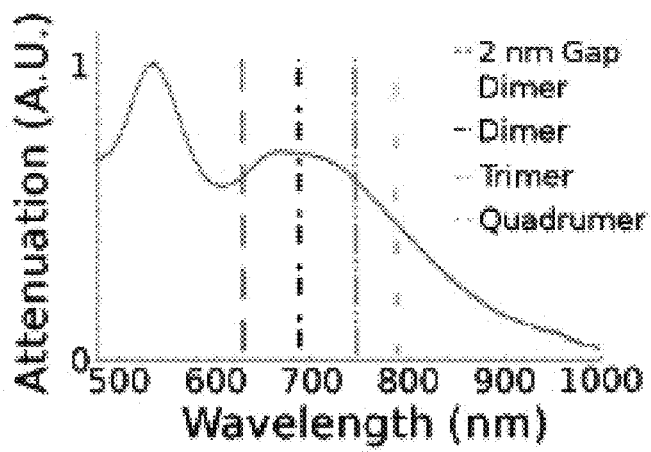
Figure 10C:
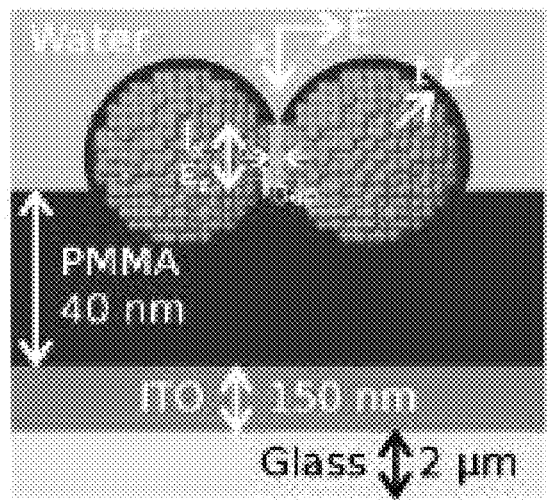

The motivation for utilizing a long-range driving force to induce chemical crosslinking in the deposition method of the application is uniformity of coverage over large areas. Therefore, UV-vis spectroscopy was used to probe the uniformity of the large-area optical response of nanoantenna samples prepared according to the methods of the application from 40 nm Au nanospheres. An area of 9 mm×0.5 mm was measured, and normalized attenuation spectra of a '40 nm EPD' sample, and, for comparison, a 'Control' sample are plotted in FIGS. 10A and 10B, respectively. Samples were prepared on transparent conductive substrates as detailed in the Materials and Methods section provided below and immersed in water during measurements to simulate the environment in a biosensing experiment. The absorption spectra of differing oligomer geometries with 0.9 nm gap spacings was simulated with the full-wave finite element method (schematic of structure of a simulated dimer is illustrated in FIG. 10C). FIG. 10A shows the simulated oligomer geometries (on the right, as detailed in the Materials and Methods section below) and the simulations overlaid as dotted curves with the measured attenuation spectrum as a solid line. This data shows that it is these different geometries that contribute to the measured attenuation spectrum.

Four distinct peaks are readily observable within the '40 nm EPD' substrate's attenuation spectrum. Simulations identify these peaks to be associated with monomers (536 nm, in good agreement with Mie scattering theory), dimers (686 nm), trimers (740 nm), and quadrumers (782 nm) with 0.9 nm gap spacings. The dashed line represents where the peak of a dimer with a 2 nm gap would appear. The absence of this peak and the other simulation results indicate that the large-area optical response is dominated by anhydride-linked oligomers with characteristic 0.9 nm gap spacing (the calculated length of an anhydride bridge). This is further corroborated by examining the attenuation spectrum of the 'Control' substrate, shown in FIG. 10B. Unsurprisingly the spectrum is dominated by monomer attenuation. Dashed, dot-dashed, dot-dot-dashed, and dotted lines representing the absorption maximum, determined from full-wave simulations of dimers with 2 nm gap, and dimer trimers, and quadrumers with 0.9 nm gaps, respectively depicted in FIG. 10B for visual clarity. No discrete oligomer peaks can be observed in the UV-vis spectrum from the 'Control' sample. Considering the absorption maximum of a 2 nm gap dimer geometry, as calculated in simulations and plotted with a dashed line in FIG. 10A, the dimer absorption peak is shifted by nearly 50 nm from the 0.9 nm dimer case. The blurring of the oligomer response for the control substrate is attributed to the lack of anhydride-mediated control of gap spacings, which results in a continuous distribution of spectral position for any given oligomer geometry.

Interestingly, UV-vis data and simulations demonstrate that oligomer gap spacings have a more profound impact on the spectral shift of an oligomer resonance than the geometry of the oligomer. These results are unsurprising when one considers that the plasmon mode is only slightly perturbed by the addition of a nanosphere on an oligomer when it is not in the polarization direction of the incident excitation beam. (Darvishzadeh-Varcheie, M., et al. Opt. Express 2016, 24, 28337-28352, the disclosure of which is incorporated herein by reference.) Consider the spectral position in the simulated absorption spectra of FIG. 10A of a linear trimer (shown in the curve with an arrow from the trimer illustration) is only blue-shifted by 4 nm from a hexamer (curve and geometry illustration are connected by an arrow). Adding two more particles to this configuration (8-particle geometry on the bottom), results in a further 3 nm spectral shift. This is a much smaller broadening than occurs when the gap spacing increases from 0.9 nm to 2 nm. The region where the resonance of a 2 nm dimer is expected is highlighted with a dashed line where the measured signal is decaying. This observation is key to understanding why the optical response is narrower than one might expect from the oligomerization statistics in FIG. 7B. As EHD flow drives the formation of close-packed oligomers, most oligomers have between three and four particles along any given polarization axis. Consider that the first circular perfectly close packed oligomer to have greater than four particles in a row contains 21 particles; 98% of oligomers observed in the 40 nm EPD substrate contain fewer than 21 particles. More significantly, the distribution statistics by number show that 93% of the surface is composed of oligomers of nine nanospheres or less. Thus, the clear majority of oligomers can be excited with a laser wavelength between the linear trimer and linear quadrumer resonance wavelengths. The peak maximum observed in the UV-vis absorption data of FIG. 10A is associated with a trimer. By exciting a surface with densely packed oligomers, observed for example in FIG. 7B (right) it is possible to excite a reproducible distribution of oligomers in any given laser spot diameter.

In summary, the UV-vis microscopy studies illustrate the effect the nanoparticle oligomer variations have on the large area optical response of the metasurface of the embodiments. In particular, using electromagnetic full-wave simulations to elucidate individual oligomer contributions to metasurface optical response shows that the optical response depends more strongly on gap spacings dimensions than oligomer geometry. In other words, the plasmon resonance is less affected by close-packed oligomer size than the resultant field enhancement in the nanogaps when the spacing decreases below 2 nm. As such, the controlled gap spacing afforded by the fabrication methods of embodiments enables, for example, exquisitely uniform SERS intensity (as discussed below in Example 3).

Example 3

Characterization of Electric Field Enhancement Via Surface Enhanced Raman Scattering (SERS)

While the TEM results support anhydride bond formation, it is also possible to spectroscopically probe molecules between nanospheres and, thus, to characterize the electric field enhancements provided by nanoantenna oligomers assembled according to the method of the application. Specifically, surface-enhanced Raman scattering (SERS) spectra provide a means to interrogate molecules near the center of the gap, where the electric field intensity is maximum. More specifically, SERS is measured by depositing a standard analyte (self-assembled monolayer) on a nanoantenna sample and observing the inelastic scattering of light—termed Raman scattering—with an energy shift that is associated with the vibrational modes present in the analyte. Here, the signal enhancement is proportional to the electric field enhancement approximately taken to the fourth power, making SERS extremely sensitive to the performance of the antenna sample.

Figure 11A:
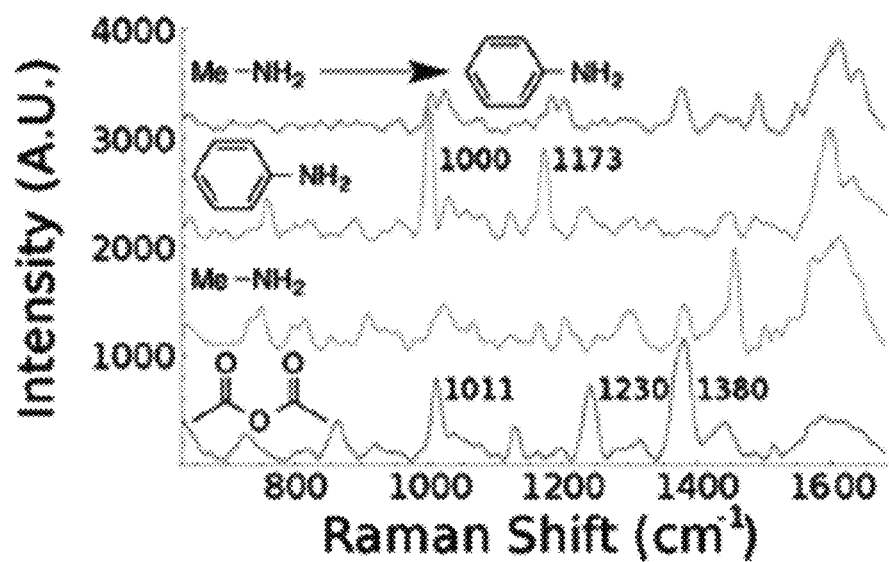
FIGS. 11A and 11B illustrate SERS analysis of the chemistry in nanogaps and ability to perform chemical reactions in nanogaps.

First, just the substrate surface prepared according to the embodiments of the application was analyzed. FIG. 11A (bottom curve) depicts a SERS spectrum of a sample prepared according to the embodiments from with 40 nm Au nanospheres. Vibrational bands associated with anhydride crosslinking groups are observed at 1011, 1230, and 1380 cm$^{-1}$, corresponding to the C—H rocking, C—O stretch, and C—H scissoring modes, respectively. These vibrational bands are used to identify anhydride moieties, as there is good contrast with carboxylic acid moieties and little overlap with N-acylisourea vibrational modes.

Next, the ability to monitor local chemistry in the gap by cleaving anhydride linkages via nucleophilic substitution was probed. The second from the bottom curve in FIG. 11A depicts a SERS spectrum observed after overnight treatment of a sample with 0.5 mM methylamine, a molecule with weak Raman bands. Notably, the vibrations associated with anhydride groups no longer stand out above the background, indicating they have been cleaved by methylamine. In order to further probe chemistry in the gaps, nucleophilic substitution of the anhydride linker with aniline, a molecule with a higher Raman cross section than methylamine, was examined. As such, the third from the bottom curve in FIG. 11A depicts a SERS spectrum observed after overnight treatment of a sample with 0.5 mM aniline. Characteristic peaks are observed at 1000 and 1173 cm$^{-1}$. For comparison, subsequent treatment of first methylamine (to cleave anhydride bonds) and then aniline (where selective attachment in the hotspot will now not occur since anhydride bonds have been cleaved) indeed shows a much weaker SERS signal for aniline. This spectrum is shown in the top curve of FIG. 11A. Here any indication of aniline in the spectrum would be due to binding to the gold surface via amine-Au interactions. This does not appear to be occurring at a significant rate, and this is reflected in the SERS spectrum. The SERS spectra showing the presence of vibrations associated with anhydride groups and then aniline groups indicate molecules can be placed in the gaps via a reaction with the cross-linking molecular group. Thus, the cross-linking chemistry used to assemble oligomers may also be used in embodiments to sense nucleophilic compounds.

Figure 11B:
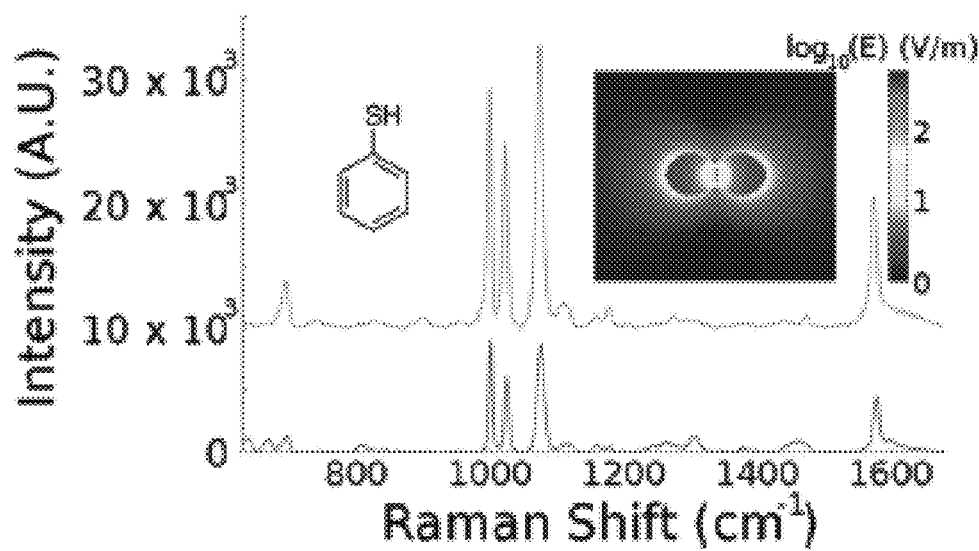

The SERS data of FIG. 11A demonstrate that functional groups used for chemical assembly and other molecules in the gaps are observable in spectra due to high electric field enhancement in the nanometer gaps. Full-wave finite elements method simulations show an electric field enhancement on the order of 600 in the hotspot region of a dimer due to the narrow gap spacing (the electric field profile on a cross section passing through the middle of the dimer is shown on a logarithmic scale in the inset of FIG. 11B). Next, field enhancements using a standard Raman reporter molecule benzenethiol (BZT) was measured. To this end, FIG. 11B (lower curve) shows SERS spectra of an oligomer sample after exposure to BZT. However, if anhydride bonds reside in the "hottest" region, BZT cannot access this region. Therefore, in order to get BZT analyte into the hotspot and maximize its signal intensity, an oxygen plasma treatment was performed on the substrate prior to exposure to BZT to remove ligands from nanosphere surfaces and clear the access to the gaps. The oxygen plasma etch reacts with the functional groups on the Au nanosphere's ligands and removes them. Removing these ligands frees additional occupation spots in the hotspots for the BZT to occupy and further reduces effects from charge transfer plasmon modes. The upper curve in FIG. 11B shows a SERS spectrum acquired after BZT exposure to the oxygen plasma treated substrate. After oxygen plasma treatment, the SERS signal from BZT increases up to 258%. The increased SERS signal is concomitant with the increased hotspot occupation volume by BZT and can be attributed to diffusion of BZT into the hotspot that is possible after removal of the anhydride from the gaps between nanospheres. Interestingly, comparison of the 1076 $cm^{-1}$ in-plane ring deformation superimposed with the C—S stretch and the 998 $cm^{-1}$ in-plane ring deformation shows greater enhancement of the 1076 $cm^{-1}$ band after removing the anhydride linker; the two peaks show approximately equal intensity in SERS data before plasma etching. This further indicates that the C—S bond has displaced the anhydride previously located in the hotspot, as the relative intensity of the vibrational modes is related to the molecular orientation in the gap. The ability to remove anhydride groups in the gaps is important for label-free SERS sensing applications, where analyte molecules in hotspots will yield lower detection limits.

Figure 12A:
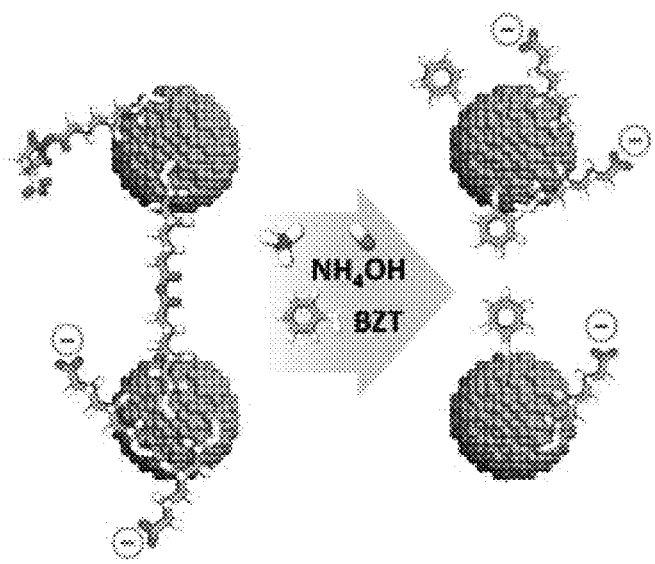
FIGS. 12A through 12C further illustrate SERS analysis of the chemistry in the nanogaps and ability to perform chemical reactions in the nanogaps.
Figure 12B:
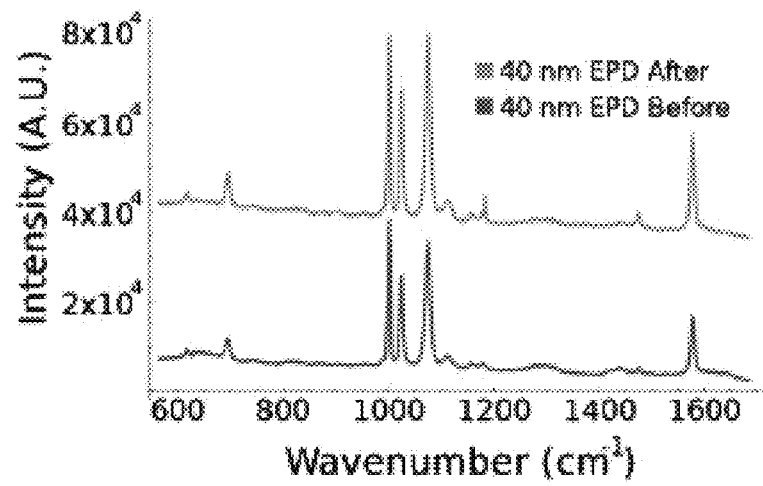

Accordingly, while anhydride bridging between metal nanospheres is useful in achieving narrow and uniform gaps between nanospheres, it also prevents a SERS analyte from residing in a hot spot. Therefore, to further test the effects of the anhydride bridges on nanoantenna sensitivity, the anhydride groups were again broken (but now via hydrolysis) in some '40 nm EPD' samples (FIG. 12A). The hydrolysis was achieved by treating the nanoantenna oligomer samples with 30% $NH_4OH$ solution for 90 minutes, with a 1 minute DI water rinse every 30 minutes. (See, e.g., Carey, F. A. Organic Chemistry. (McGraw-Hill, 2006), the disclosure of which is incorporated herein by reference.) FIG. 12B depicts SERS spectra of BZT from a '40 nm EPD' sample before and after the $NH_4OH$ base treatment. The spectra taken are from identical locations which are located by bleaching a 8 µm×5.5 µm polymeric template area through electron bombardment with SEM. A 145% improvement in signal of the 998 $cm^{-1}$ band is observed for the '40 nm EPD' sample after the base treatment. Although not to be bound by theory, the improvement in signal is believed to be due to two mechanisms arising from cleaving the anhydride bridging:

(1) the reduction of charge transfer plasmon modes that are non-radiative and do not contribute to the Raman signal, and
(2) freeing up occupation spots in the hotspot between nanospheres for BZT to occupy.

Mechanism (1) is explained by the increase of the 998 $cm^{-1}$ peak. However, mechanism (2) requires further analysis of individual peaks in the Raman spectra before and after hydrolysis of the anhydride bridge. To this end, after treatment, the 1076 $cm^{-1}$ peak—in-plane ring deformation superimposed with C—S stretch—increases in strength relative to the 998 $cm^{-1}$ peak—in-plane ring deformation. This suggests a change in the orientation of the BZT in the hotspot after base treatment, which alters the relative intensity of different Raman peaks. The 162% improvement of the 1076 $cm^{-1}$ mode—in comparison to 145% for 998 $cm^{-1}$ mode—implies that the C—S stretch vibration is enhanced more than the ring breathing vibration after base treatment. This indicates that Au—S bonds displace the anhydride bonds previously located directly between the Au nanospheres where the electric field is the largest. Furthermore, notably, the 634 $cm^{-1}$ and 667 $cm^{-1}$ peaks no longer appear in the spectra after base treatment. Vibrations of this energy are often C—H wagging modes and their disappearance suggests that they are C—H wagging modes of the anhydride bridge. These results further demonstrate that anhydride bridges form during oligomerization as described above. Accordingly, many embodiments incorporate these treatments in method of fabrication to allow for improved performance of embodiments as optical sensors.

Figure 12C:
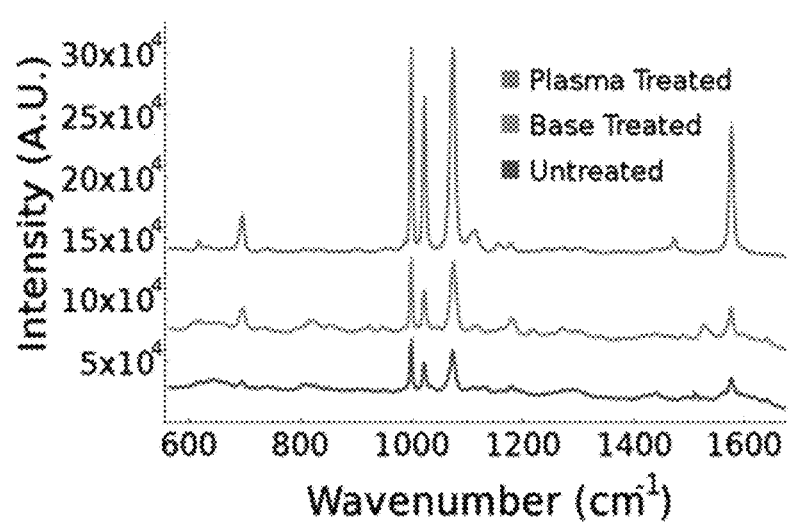

However, even further improvements to the SERS intensity are observed for the substrates treated with a 120 second oxygen plasma etch (FIG. 12C) instead of the base treatment. A 263% and 300% increase in signal compared to the untreated sample is observed for the 998 $cm^{-1}$ band and 1076 $cm^{-1}$ band, respectively. The baseline signal is also observed to decrease by nearly threefold after plasma treatment compared to the untreated sample, which contributes to the dramatic increase of the analyte's signal.

Figure 13A:
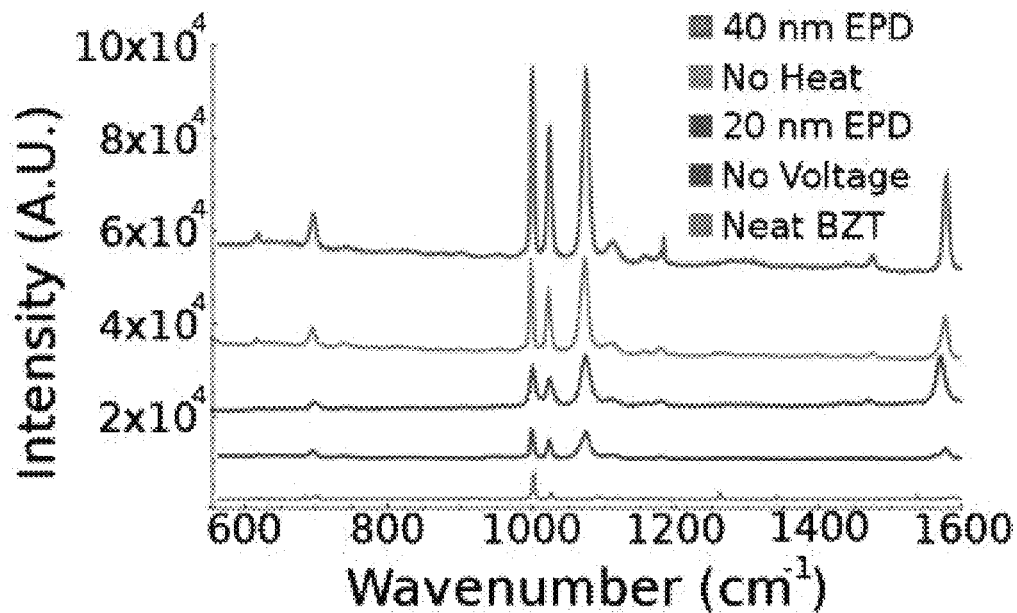
FIGS. 13A and 13B illustrate SERS performances of the metasurfaces prepared with varied metasurface fabrication parameters according to embodiments.

In addition, SERS performance of differently prepared samples of the disclosure was also compared. FIG. 13A depicts the Raman scattering spectra obtained with BZT analyte on various nanoantenna samples of the disclosure (all used after a base treatment) and of neat BZT solution. As outlined in the Supplemental Information section below, calculations of the number of molecules in the sampling volume in the neat measurement of the BZT solution contains seven to eight orders of magnitude more molecules than SERS measurements of the nanoantenna samples. This large disparity is observed because a 3D volume is probed for the neat measurements, while only a 2D self-assembled monolayer of BZT on the nanoantenna regions is probed for the samples of the disclosure. Thus, qualitatively, the nanoantenna sample's comparable magnitude of Raman scattering intensity clearly conveys the large electric field enhancement due to the nanoantenna oligomers prepared in accordance with the embodiments of the application.

Figure 13B:
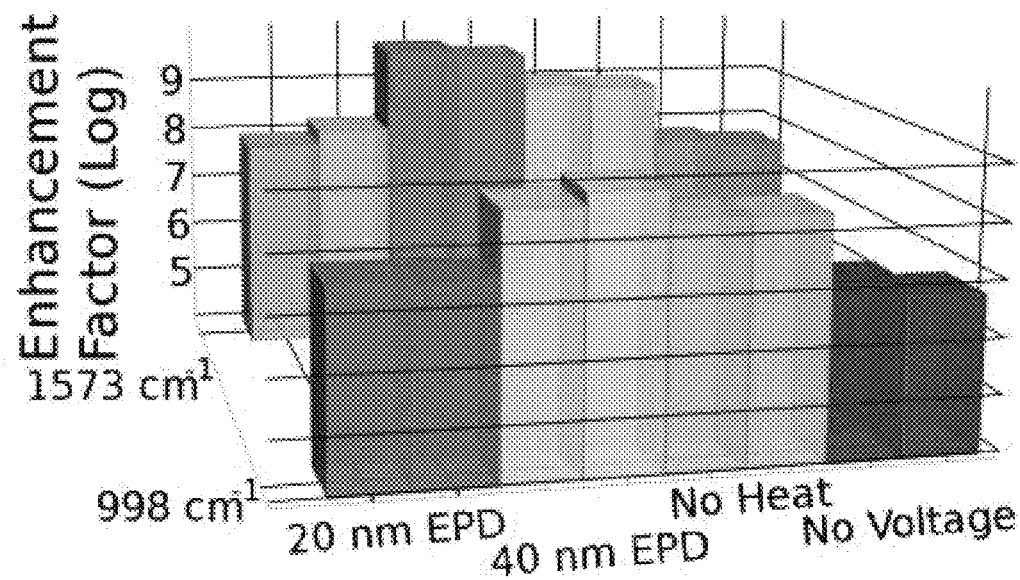

FIG. 13B quantifies the performance of the nanoantenna oligomer samples of the disclosure through the sample's enhancement factor (EF). Here, EF is defined by Equation 1:

$$EF=(I_{SERS}/N_{SERS})/(I_{NEAT}/N_{NEAT}) \quad \text{(Eq. 1)}$$

where $I_{SERS}$ is the SERS intensity from the sample, $I_{neat}$ is the neat Raman intensity from the bulk solution, $N_{SERS}$ is the number of molecules participating in the SERS, and $N_{neat}$ is the number of molecules participating in neat measurements. (See, e.g., Fleischmann, M.; et al., Chem. Phys. Lett.

26, 163-166 (1974), the disclosures of which are incorporated herein by reference.) Thus, the SERS EF is the ratio of Raman scattered intensity per molecule of the antenna sample to that of the neat analyte. Estimating the number of molecules is a common source of error in determining the SERS EF, so a method for determining EF that avoids these approximations is used here. Here, the control for the spot size is achieved by using the same water immersion microscope objective for all measurements, and the confocal collection depth is directly measured during the neat BZT measurement according to the method of Cai et al. (See, e.g., Cai, W. B. et al. Surf. Sci. 406, 9-22 (1998), the disclosure of which is incorporated herein by reference.) As such, all parameters involved in the EF calculation are directly measured. Indeed, using common assumptions in the literature estimating the number of molecules probed, unrealistic EFs in excess of $10^{11}$ are determined for the '40 nm EPD' sample of the disclosure. FIG. 13B shows the calculated EF taken from 'No Voltage', 'No Heat', '40 nm EPD' and '20 nm EPD' nanoantenna samples of the disclosure for both the 998 cm$^{-1}$ Ring out-of-plane deformation and 1573 cm$^{-1}$ C—H out-of-plane bending peaks. Raman scattering peaks from two different vibrational modes were used to calculate EF as the Raman scattering intensity may vary between vibrational modes for several reasons, including resonant enhancement due to charge-transfer transitions and other chemical enhancement pathways. (See, e.g., Saikin, S. K., Olivares-Amaya, R., Rappoport, D., Stopa, M. & Aspuru-Guzik, A. Phys. Chem. Chem. Phys. 11, 9401 (2009), the disclosure of which is incorporated herein by reference.)

Here, the '40 nm EPD' sample produces EFs on the order of $1.3 \times 10^9$ using the 1536 cm$^{-1}$ Raman band, outperforming all other samples (FIG. 13B). Specifically, first, the '40 nm EPD' sample outperforms the '20 nm EPD' sample by two orders of magnitude. Although not to be bound by theory, this performance is believed to be due to four factors:

(1) the additional anhydride bridging afforded for the 40 nm nanospheres due to increased force density generated by EHD flow;
(2) the intrinsically higher electric field enhancements that results from 40 nm nanospheres, (as observed in the simulation of a dimer depicted in FIG. 22);
(3) the 40 nm nanosphere-based oligomers, of any degree of oligomerization, are closer to resonance with the 785 nm excitation wavelength compared to the larger oligomers comprised of 20 nm nanospheres, which are off resonance at the 633 nm excitation;
(4) a greater number of occupation sites for BZT in the hotspot between 40 nm nanospheres than in the 20 nm nanospheres, which scales with surface area.

Next, the '40 nm EPD' sample also outperforms the 'No Heat' sample by nearly an order of magnitude. There is a greater fraction of oligomers composed of five or more nanospheres in the 'No Heat' sample composed in a linear arrangement, such structures are off resonance at 785 nm laser excitation. Consider that increased temperature increases Brownian motion, which in turn promotes monomer formation via increased collisions of nanospheres with the templated substrate surface. These seeded monomers lead to EHD flow, as outlined earlier in this disclosure, and promote further attachment of nanospheres to the template bound nanospheres. However, such growth is limited by jamming of the surface by other existing oligomers, so increased monomer deposition will prevent large oligomers from growing. This process is analogous to crystal growth, where a high density of nucleation sites leads to the formation of smaller grains. Therefore, the 'No Heat' sample are expected to have fewer monomers serving as "nucleation" sites and, as such, larger oligomers are expected to form in comparison with the heated '40 nm EPD' sample. The 'No Voltage' sample achieves an EF of $5 \times 10^7$, this enhancement factor corresponds to a >2 nm gap spacing in full wave simulations. Overall, the SERS data reaffirms the cluster statistics presented in FIGS. 5A through 7C and Tables 1 and 2, showing that the EHD flow has a profound impact on the formation and retention of anhydride bridges between nanospheres and, in turn, the macroscopic optical properties.

Figure 14:
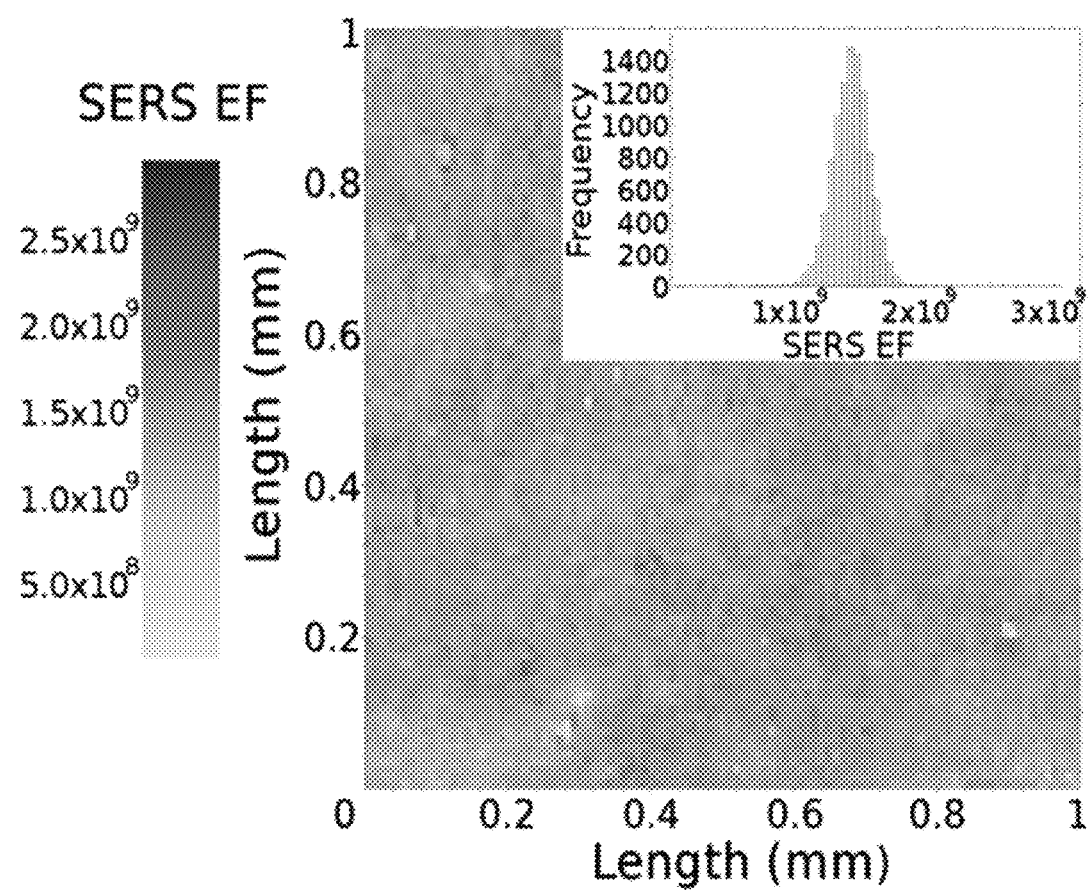
FIG. 14 illustrates uniformity of SERS intensity from the metasurface fabrication according to embodiments.

The large scale optical uniformity of the (oxygen plasma treated) '40 nm EPD' nanoantenna samples fabricated according to the embodiments of the application was further demonstrated by acquiring a 1 mm$^2$ SERS intensity and a SERS EF map when excited with a 785 nm laser source at 76 μW for 0.1 s exposure times, shown in FIG. 14 The small gap spacings in oligomers enabled by the (cleavable) anhydride cross-linker provided by template-seeded EHD flow should yield a model system for SERS. The EF is determined by assembling a self-assembled monolayer of BZT onto the substrate and observing the intensity of the 1573 cm$^{-1}$ vibration band. The raw SERS data are converted into an EF using Eq. 1. The number of BZT molecules participating in the SERS measurements is determined through the average surface coverage of nanospheres assumed to be coated with a self-assembled monolayer of BZT over the mapped region, obtained using SEM images. The average coverage is used for all EF calculations. The SERS map shows an average SERS EF value of $1.4 \times 10^9$. The data shows a 10% relative standard deviation (RSD) of the 1573 cm$^{-1}$ peak across the mapped area with a full-width at half maximum (FWHM) of $3.5 \times 10^8$, which is less than the proposed variability for an acceptable spot to spot variation in an effective SERS sensor. (See, e.g., Natan, M. J. Faraday Discuss. 132, 321 (2006), the disclosure of which is incorporated herein by reference.) This is extremely useful for diagnostic studies requiring fast analysis and low power, as is often the case in biosensing applications. In addition, it should also be noted that all SERS samples prepared according to the embodiments of the application were reusable, and had a shelf life on the order of years. For example, re-immersing the nanoantenna samples in benzenethiol solution every few days yielded the same SERS results. Overall, the SERS EF is approximately proportional to the electric field enhancement taken to the fourth power, indicating that the oligomers prepared according to the embodiments of the application achieve extraordinarily large electric field enhancements while providing point-to-point uniformity in the spot size of the optical beam. The low signal deviation is a result of the seeded growth oligomerization method of the application that is optimized by controlling the temperature, block copolymer template, and EHD flow in accordance with embodiments, as described above.

In summary, the SERS studies indicate that the electric field enhancement produced by oligomers assembled according to embodiments appears to be relatively uniform over a 1 mm$^2$ area, with a relative standard deviation in signal of 10%, which is significant because the SERS enhancement factor has an average value of $1.4 \times 10^9$. Furthermore, the SERS studies results demonstrate that the colloidal assembly method of embodiments, which uses long-range driving forces to drive chemical cross-linking between nanospheres, produces exquisite plasmonic devices, capable of overcoming the typical to SRES measurements trade-offs between uniformity and high electric field enhancements in SERS. Overall, the uniform SERS response with large enhancements over large area enables the use of the SERS substrates of embodiments in device architectures. Of further significance, the same properties of the metasurfaces of embodiments also enable the acquisition of large data sets needed for statistical analysis enabling quantitative detection of small molecules (as discussed below in Example 4).

Example 4

Longitudinal Monitoring of Biofilm Formation Via SERS Quantification of *Pseudomonas aeruginosa*-Produced Metabolites During biofilm formation, differential gene expression is regulated through a cell density-dependent mechanism called quorum sensing (QS). Soon after surface attachment, bacteria begin producing extracellular polymeric substances and QS signaling molecules. Once formed, a combination of physical mechanisms and genetic and metabolic adaptations within the biofilms imparts extreme antibiotic tolerance or resistance to the constituent cells, which can withstand up to 1000 times higher doses of antibiotics than their free floating planktonic counterparts. For example, *Pseudomonas aeruginosa* (*P. aeruginosa*) is a biofilm-forming, opportunistic pathogen that is associated with the contamination of medical devices and respiratory infections in immunocompromised patients and is one of the most common bacteria isolated in chronic wounds. Among the many virulence factors and QS compounds that *P. aeruginosa* produces is pyocyanin, a redox-active secondary metabolite, which can act as a terminal signaling factor in the QS process. While new antimicrobial strategies are being developed to combat antibiotic resistance, sensing bacterial metabolites associated with QS, such as pyocyanin, for early detection of biofilm formation (at a stage where antibiotic treatment has higher efficacy) might be an equally useful strategy.

Interestingly, recent Raman spectroscopy-based studies have demonstrated the ability to distinguish between species of bacteria, identify molecules enriched in particular species, and even detect specific local metabolic activity in environmental samples using stable isotope probing techniques. (See, respectively: Lorenz, B., et al. Trends Microbiol. 2017, 25, 413-424; Wu, X., et al. Talanta 2015, 139, 96-103; Ghebremedhin, M., et al. J. Clin. Microbiol. 2017, 55, 2480-2490; Berry, D., et al. Proc. Natl. Acad. Sci. U.S.A. 2015, 112, E194-E203, the disclosures of which are incorporated herein by reference.) For example, Raman spectroscopy has been demonstrated to outperform matrix-assisted laser desorption ionization-time of flight mass spectrometry in accurately discriminating between *Acinetobacter baumannii* strains. In particular, most usefully, Raman spectra provide "molecular fingerprints" composed of the vibrational spectrum of molecules serving as a label-free detection method. Biologically relevant concentrations of metabolites often range from nM to mM levels in clinical samples, and the ability to detect them has enormous potential for enabling personalized medicine. The limit of detection (LOD) and quantification range of metabolite concentration needed at physiologically significant levels in biological samples, though this may vary with molecules and environments, is often in the μM range, and, therefore, requires large and reproducible enhancements of Raman signals. Surface-enhanced Raman scattering (SERS), when employing plasmonic nanogaps, is capable of providing necessary enhancements to achieve detection at biologically relevant concentrations. As such, SERS has been used to distinguish between colony biofilms of bacteria species during maturation phases and even to detect pyocyanin in spiked saliva down to 2.1 $\mu g \cdot mL^{-1}$ (10 μM) and spiked in subcutaneous implants in mice down to 0.1 μM. (See, respectively: Keleştemur, S. & Çulha, M. Appl. Spectrosc. 2017, 71, 1180-1188; ukovskaja, O., et al. Sensors 2017, 17, 1704; Bodelón, G., et al. Nat. Mater. 2016, 15, 1203-1211, the disclosures of which are incorporated herein by reference.) However, challenges still exist in incorporating nanogaps with large and uniform enhancement factors in device architectures with nM detection limits and quantification spanning the range of metabolite concentrations found in biological samples.

SERS enhancement factors due to plasmonic nanogaps are highly dependent on the distance between plasmonic nanoantennas, increasing monotonically with decreasing gap size. Statistical analysis of various size-controlled nanogaps using DNA tethering observed single molecule SERS intensity when nanogaps are on the order of 0.5-0.9 nm. At nanogap distances below approximately 0.5 nm, depolarization effects attributed to quantum tunneling reduce enhancements. Reaching sub-nanometer nanogap dimensions over large area without large variations is difficult, and thus, SERS substrates often exhibit tradeoffs between reproducibility and large enhancement factors. However, it is necessary to have both uniform and large enhancement factors across SERS substrates to reproducibly achieve low detection limits in quantitative sensing applications. Consider that at extremely low concentrations, analyte molecules will not be uniformly distributed across the surface. SERS measurements on a mixture of two different analytes determined that single molecule sensing events occur at nM concentration as not every molecule in the scattering volume will reside in a hotspot. Inherent variances in SERS substrates' enhancement factors only worsen any analyte's location-dependent signal variations and will lead to large SERS intensity fluctuations. While such surfaces may produce a low LOD because of the presence of a few hotspots on the surface, the limit of quantification (LOQ) will be much higher. Thus, increasing the uniformity and density of nanogaps with high enhancements will lead to a higher probability that an analyte will adsorb on a hotspot in the illuminating laser spot size and thereby reproducibly contribute to the SERS signal at low concentrations.

Accordingly, in many embodiments the nanoantenna on SERS substrates fabricated according to the embodiments of the application may be used in the detection of bacterial metabolites at low concentrations in fluids with complex background. First, they can be produced to have a high density of oligomers with sub-nanometer nanogap spacing and with large-scale uniformity in hotspot intensity. More specifically, as described here the fabrication process of embodiments achieves a high yield of close-packed oligomers composed of 10 nanospheres or less with gap spacing of 0.9 nm, having an electric field enhancement on the order of 600 in the hotspot region. Notably, the achieved close-packing is also advantageous in allowing for variability of oligomer orientation with respect to polarization of incident light. That is, in a close-packed oligomer, the plasmon resonance will most closely reflect that of a linear oligomer along the polarization axis.

Furthermore, as has been shown in this disclosure, SERS signals exhibit a relative standard deviation (RSD) of 10% across a 1 $mm^2$ area with benzenethiol as the analyte. This achievable uniform SERS response allows for the incorporation in microfluidic device architectures and spectral data analysis using multivariate machine learning algorithms. A large number of training data sets and the full spectra collected from SERS substrates are necessary for accurate quantitative analysis by accounting for signal variance inherent to SERS. Accordingly, in many embodiments, by combining uniform SERS substrates of the application having high signal enhancements with multivariate statistical analysis of SERS spectra, it is possible to differentiate bacterial metabolites in complex biological media at extremely low concentrations and robustly quantify concentrations spanning several orders of magnitude. In many such embodiments, it is possible to differentiate specific small molecules, such as pyocyanin, in the complex soup of biological media at concentrations down to 1 ng·mL$^{-1}$ (4.8 nM) and robustly quantify concentrations spanning 5 orders of magnitude. Moreover, in many embodiments, rapid SERS analysis in solutions negates the need to grow biofilms directly on SERS substrates or to drop-cast plasmonic clusters on static biofilms, thus allowing instantaneous quantification of small molecule metabolites for the detection of biofilm formation on any surface, or in solution, or even in the air, as long as the metabolite of interest can be contacted with a SERS substrate of embodiments (via, for example, a rinse of the potentially contaminated matter). In many embodiments, longitudinal monitoring of the supernatant from bacterial cultures in microfluidic devices exhibits SERS signal from pyocyanin as early as 3 h after *P. aeruginosa* culture inoculation, which is well before surface-attached bacteria exhibits a decreased susceptibility to bactericidal antibiotic carbenicillin that was measured at 10 h. In many embodiments, low-cost fabrication of nanoantennas of the application with nanometer-scale nanogaps over large areas enabled by self-assembly and statistical spectral analysis of SERS data demonstrate the capacity for fabricating device architectures capable of early detection of biofilms enabling effective antimicrobial treatment.

Quantification and Detection of Pyocyanin in Aqueous Media. Pyocyanin exhibits a broad absorption band from 550 to 900 nm; thus using a 785 nm laser to excite nanoantennas results in surface-enhanced resonance Raman scattering (SERRS). SERRS spectra of aqueous pyocyanin from 1 μg·mL$^{-1}$ (4.8 μM) to 100 μg·mL$^{-1}$ (480 μM) (FIG. 15A) displays clear Raman bands similar to pyocyanin spectra reported using surfaces with Ag colloids and Ag and Au nanorods at 552, 1353, 1602, and 1620 cm$^{-1}$. These bands rise at a concentration as low as of 100 pg·mL$^{-1}$ (480 pM), as exemplified in FIG. 15B for the band 552 cm$^{-1}$. The log-log dose-response curve of pyocyanin at 552 cm$^{-1}$ (FIG. 15C) reveals a linear regime between 1 ng·mL$^{-1}$ and 10 μg·mL$^{-1}$, consistent with Langmuir adsorption kinetics; similar linear relationships with concentration are also observed for other pyocyanin vibrational bands, and results are shown in FIG. 16. Within this linear regime, pyocyanin concentration can be quantified using the formula shown in Eq. 2 with $R^2=0.951$:

$$\log C = a \log I + b \qquad (Eq.\ 2)$$

Here a and b are fitting constants with value of 3.623 and 2.924, respectively, while C and I represent pyocyanin concentration and normalized SERRS intensity at 552 cm$^{-1}$, respectively. For concentrations below the LOQ, 1 ng·mL$^{-1}$, SERS substrates detection of pyocyanin was determined by comparing the signal and background at 552 cm$^{-1}$ per guideline EP17 of the Clinical and Laboratory Standards Institute. The limit of blank (LOB) is calculated by adding the mean background signal [deionized (DI) water] $\bar{I}_{bg}$ at 552 cm$^{-1}$ to 1.645 its standard deviation $\sigma_{bg}$, as shown in Eq. 3:

$$LOB = \bar{I}_{bg} + 1.645\ \sigma_{bg} \qquad (Eq.\ 3)$$

Detection is defined in the standard manner where the mean signal, $\bar{I}_D$, at 552 cm−1 is at least 1.645 standard deviations, σD, larger than or equal to the LOB, as shown in Equation 4:

$$\bar{I}_D - 1.645\ \sigma_D \geq LOB \qquad (Eq.\ 4)$$

Figure 15C:
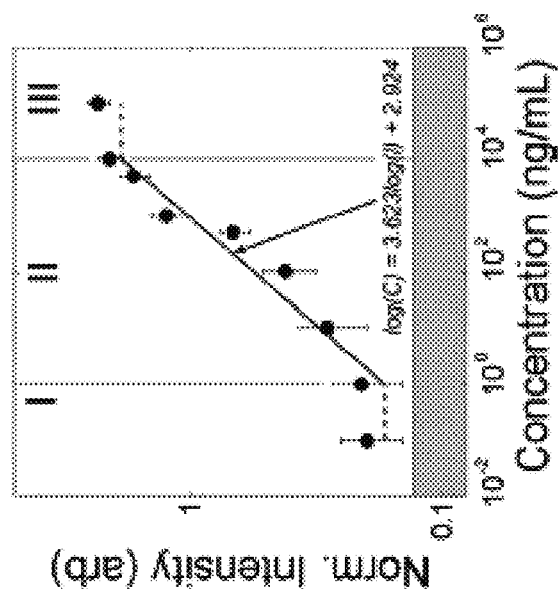
FIGS. 15A through 15C illustrate quantification and detection of pyocyanin in aqueous media using SERS intensity based on the metasurface assembled according to embodiments.
Figure 15B:
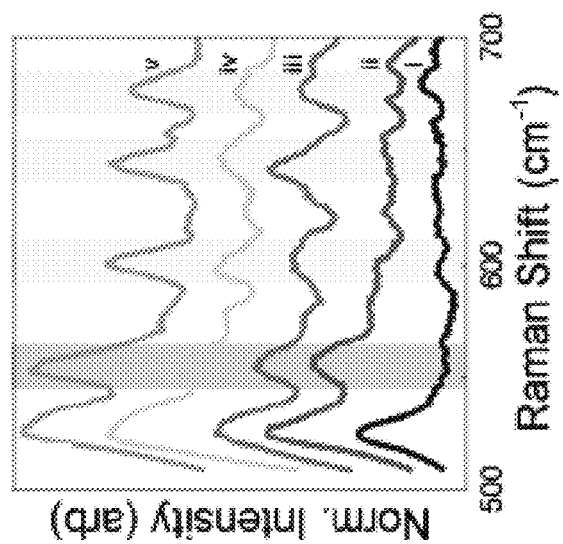
Figure 15A:
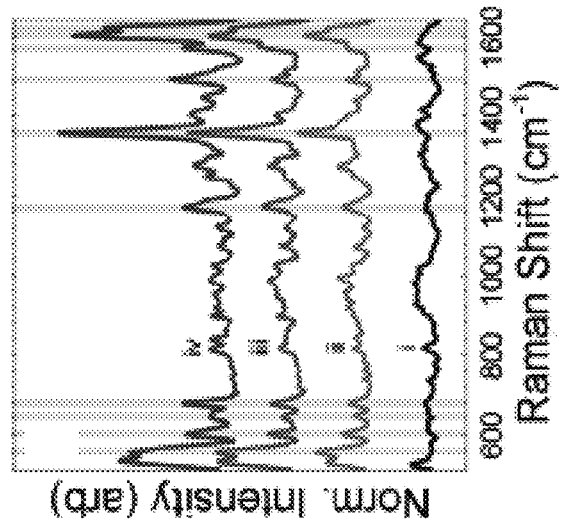
Figure 16:
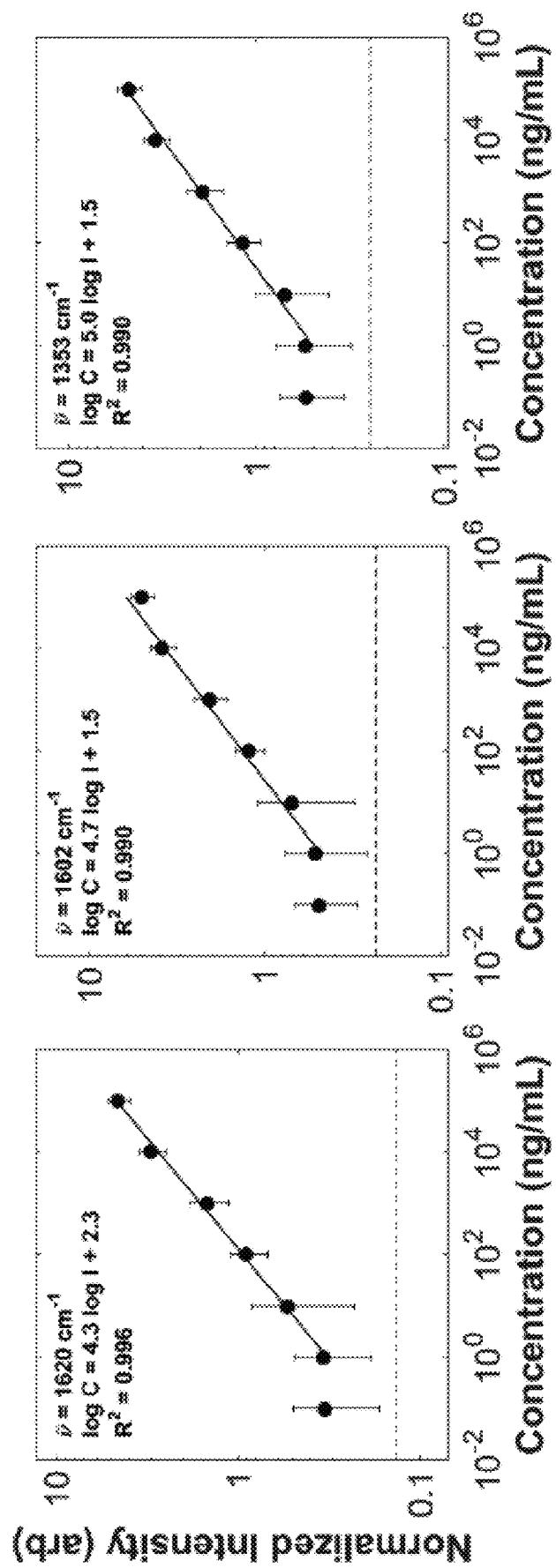
FIG. 16 provides dose-dependent response of pyocyanin vibrational bands collected by a detecting system based on the metasurface assembled according to embodiments.

From this analysis, SERS substrates in accordance with embodiments exhibit detection of pyocyanin in aqueous media at a concentration of 100 pg·mL$^{-1}$, above which one can observe pyocyanin signals above the background in FIG. 15C.

More Specifically—Dose-Dependent Response Of Pyocyanin Vibrational Bands. The log-log dose-response curves of commonly observed pyocyanin vibrational modes (1620 cm$^{-1}$, 1602 cm$^{-1}$, and 1353 cm$^{-1}$) were determined from the corresponding normalized SERRS intensity. The intensity versus concentration was also fit to Eq. 2. The linear regression results are plotted in FIG. 16.

Training Data Acquisition and Building Multivariate Predictive Model. Using linear regression on a single Raman band allows for facile comparison with other SERS surfaces in the literature as it is widely used for quantitative calibration. While this method is sufficient for the analysis of a pure analyte in water, it discards the remaining rich spectral information in each spectrum and can lose sensitivity when other molecules are present in solution as is the case when monitoring biofilm growth. Alternatively multivariate analysis, specifically partial least square (PLS) regression, analyzes the full spectra collected from SERS substrates and improves LOQs in complex media. (See, Nguyen, C., et al. Biosensing and Nanomedicine X, Proceedings of SPIE Nanoscience+Engineering; International Society for Optics and Photonics: San Diego, Calif., Aug. 6-10, 2017, the disclosure of which is incorporated herein by reference.) Thus, it is possible to capitalize on the uniform SERS response of the metasurfaces prepared according to the method of the application to acquire necessary training data and employ PLS analysis to quantify a bacterial metabolite, such as pyocyanin, in a more complex biological media—an important requirement for diagnostic applications. Accordingly, in many embodiments, training data sets, composed of SERRS spectra from known concentrations of an analyte (e.g., pyocyanin) spiked in LB media, generate a robust PLS-predictive model for pyocyanin concentration in the increased background noise of the biological media. Here, the predictive capability of the multivariate model of the application is demonstrated by quantifying pyocyanin production from *P. aeruginosa* planktonic cultures during in vitro growth.

Figure 17A:
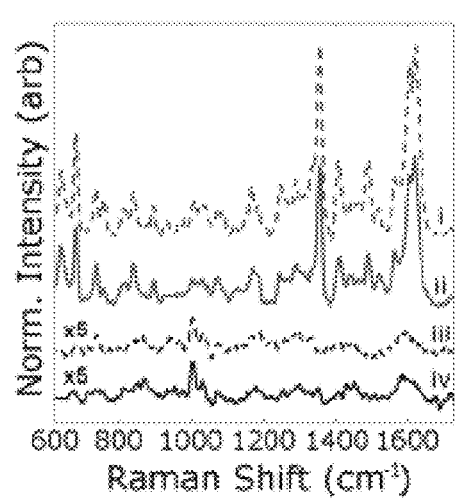
FIGS. 17A through 17D illustrate training data acquisition and building of multivariate predictive model (FIGS. 17A and 17B) for pyocyanin quantitative detection in complex media by a detection system based on the metasurface assembled according to embodiments.

First, the suitability of the metasurface substrates of embodiments for detecting pyocyanin in complex media is demonstrate by comparing SERRS spectra of blank LB media, LB media spiked with 10 μg·mL$^{-1}$ of pyocyanin alongside spectra of cell-free supernatants collected from mid-stationary phase cultures of wild-type *P. aeruginosa* PA14 and its phenazine-deficient mutant strain Δphz1/2 as a control (FIG. 17A). The Δphz1/2 strain does not produce phenazines; hence its SERRS spectrum (multiplied by a factor of 5 for clarity) indeed lacks the vibrational fingerprint of pyocyanin and is similar to the spectrum obtained for blank LB media. Meanwhile, SERRS spectra of wild-type PA14 and pyocyanin in LB broth exhibit similar features, including distinct pyocyanin vibrational bands, thus confirming the suitability of the metasurface substrates of the application for the task. While pyocyanin signals are clearly seen here, signal interference from other molecules is amplified at low concentration, requiring more sophisticated analysis.

Figure 17B:
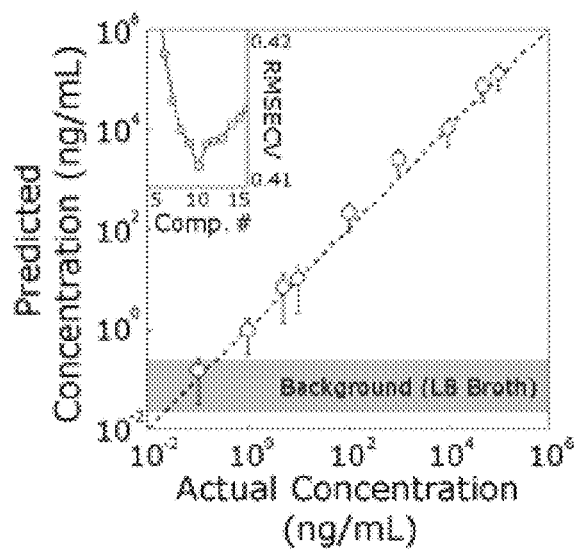

The calibration data sets that were acquired by collecting SERRS spectra of LB media spiked with 100 pg·mL$^{-1}$ to 100 µg·mL$^{-1}$ pyocyanin generated a predictive model of pyocyanin concentration in LB media using PLS regression. From the 400 spectra collected for each pyocyanin dose, 380 were randomly selected as training sets and the remaining 20 withheld as the testing sets. To optimize the model, over- and under-fitting are avoided by using 10 PLS components where a minimum in root mean square error of cross validation (RMSECV) is observed (see inset of FIG. 17B). With the testing set, the model demonstrates accurate prediction between 1 ng·mL$^{-1}$ and 100 µg·mL$^{-1}$, as shown in FIG. 17B. Fitting the predicted versus actual concentration with a line having a slope of 1—representing perfect predictive capability—gives a $R^2$ value of 0.956.

Figure 17C:
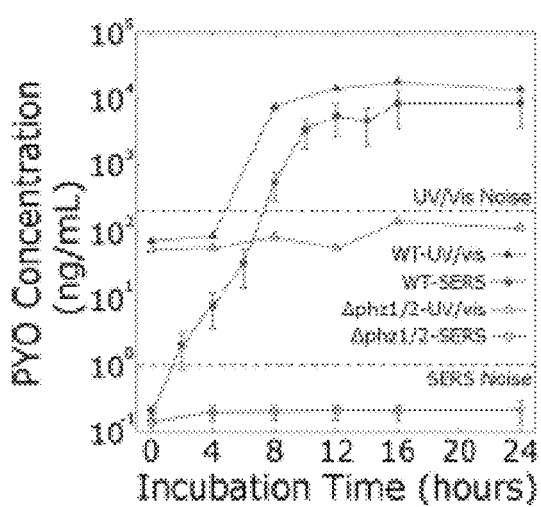

Pyocyanin Quantitative Detection in Complex Media. The generated predictive model, in accordance with embodiments, was used to quantify pyocyanin from SERRS spectra of cell-free conditioned growth medium of wild-type *P. aeruginosa* and Δphz1/2 as a function of incubation time. For each incubation time point, 400 SERRS spectra were collected within the span of less than 4 min, and their corresponding pyocyanin concentrations were calculated using the PLS model; the average concentration for incubation times ranging from 0 to 24 h is shown in FIG. 17C. The performance of SERRS-PLS was compared with UV-vis absorption spectroscopy typically employed to quantify pyocyanin. Pyocyanin concentrations were calculated from UV-vis absorption peaks using the reported molar absorptivity $\varkappa=4.31\times10^3$ mol$^{-1}$ cm$^{-1}$ at $\lambda$max=690 nm.

Figure 17D:
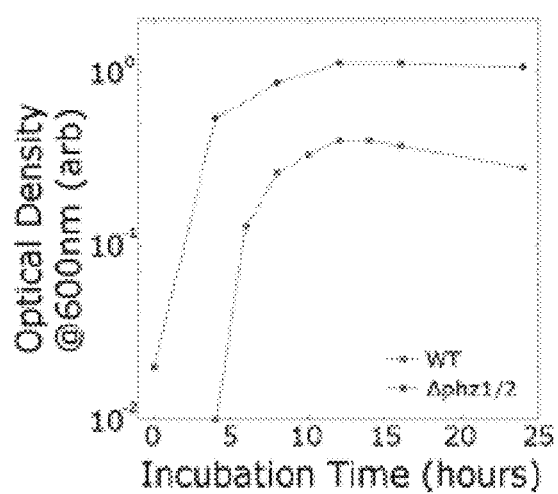

The pyocyanin-deficient Δphz1/2 strain was used to calculate the instrument noise and contributions from the background media. This yielded the UV-vis LOD as 197 ng·mL$^{-1}$ (0.94 µM), equivalent to three standard deviations above the background of the Δphz1/2 strain. This value agrees well with the reported LOD of 1 µM for UV-vis. The UV-vis data is also plotted in FIG. 17C for comparison with SERRS data. The LOD of SERRS observed in FIG. 17B is 1 ng·mL$^{-1}$ (4.8 nM) using the same definition for differentiating from background noise and PLS model discussed above. Thus, SERS substrates are able to detect pyocyanin as early as 2 h of shaking culture growth and quantify the concentration as 2.5 ng·mL$^{-1}$ (12 nM), as opposed to after 8 h of shaking culture growth when using UV-vis absorption. From 8 h onward, quantitative performance of the two methods is comparable. The sharp increase in pyocyanin concentration detected by SERRS from 2 to 8 h correlates with the exponential growth phase of *P. aeruginosa* in the shaking culture, which is observed in FIG. 17D as an increase in optical density and, thereby, accumulation of biomass. Overall, these data validate the robustness of SERS substrates of the embodiments toward the detection of small molecule analytes, such as pyocyanin, in complex media.

Figure 18A:
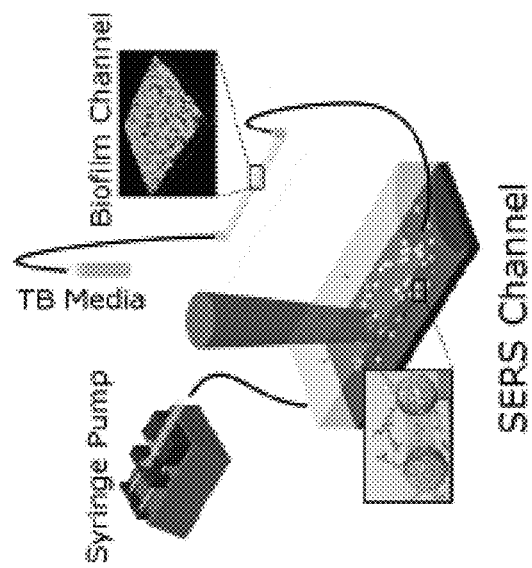
FIGS. 18A through 18E illustrate monitoring of biofilm formation via pyocyanin quantification by a microfluidic system based on the metasurface assembled according to embodiments.
Figure 18B:
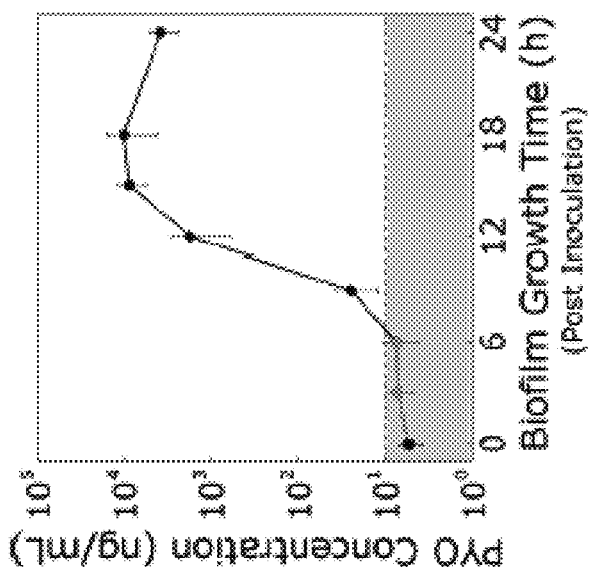
Figure 18C:
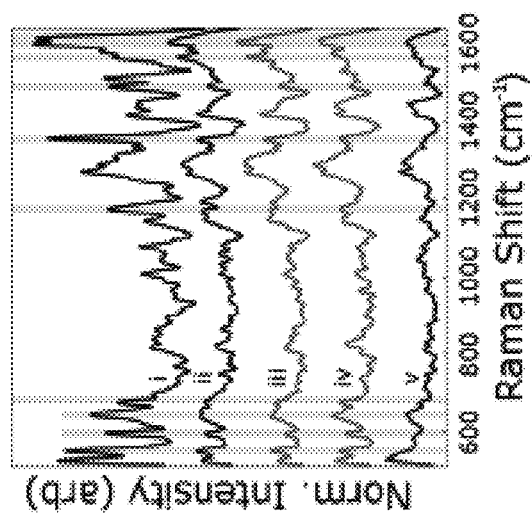
Figure 18E:
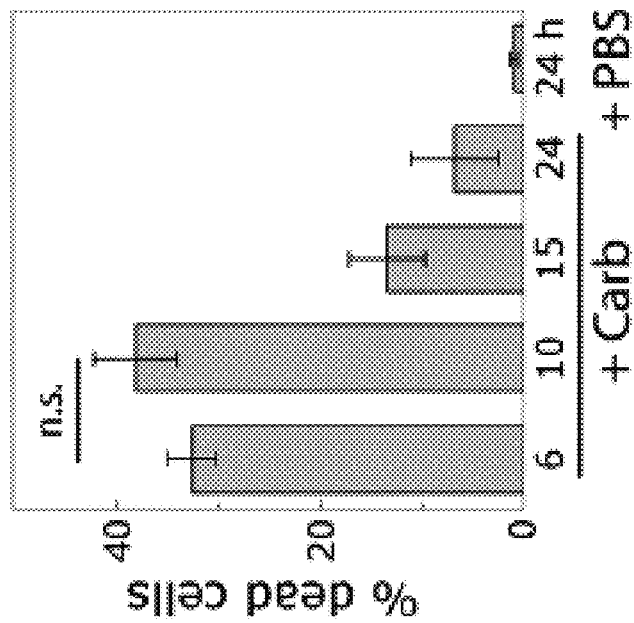
Figure 18D:
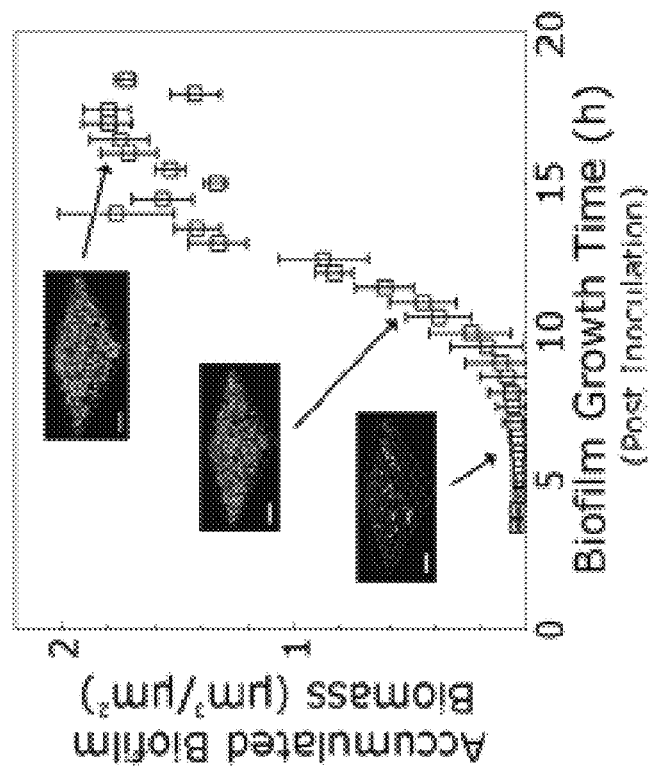
Figure 19:
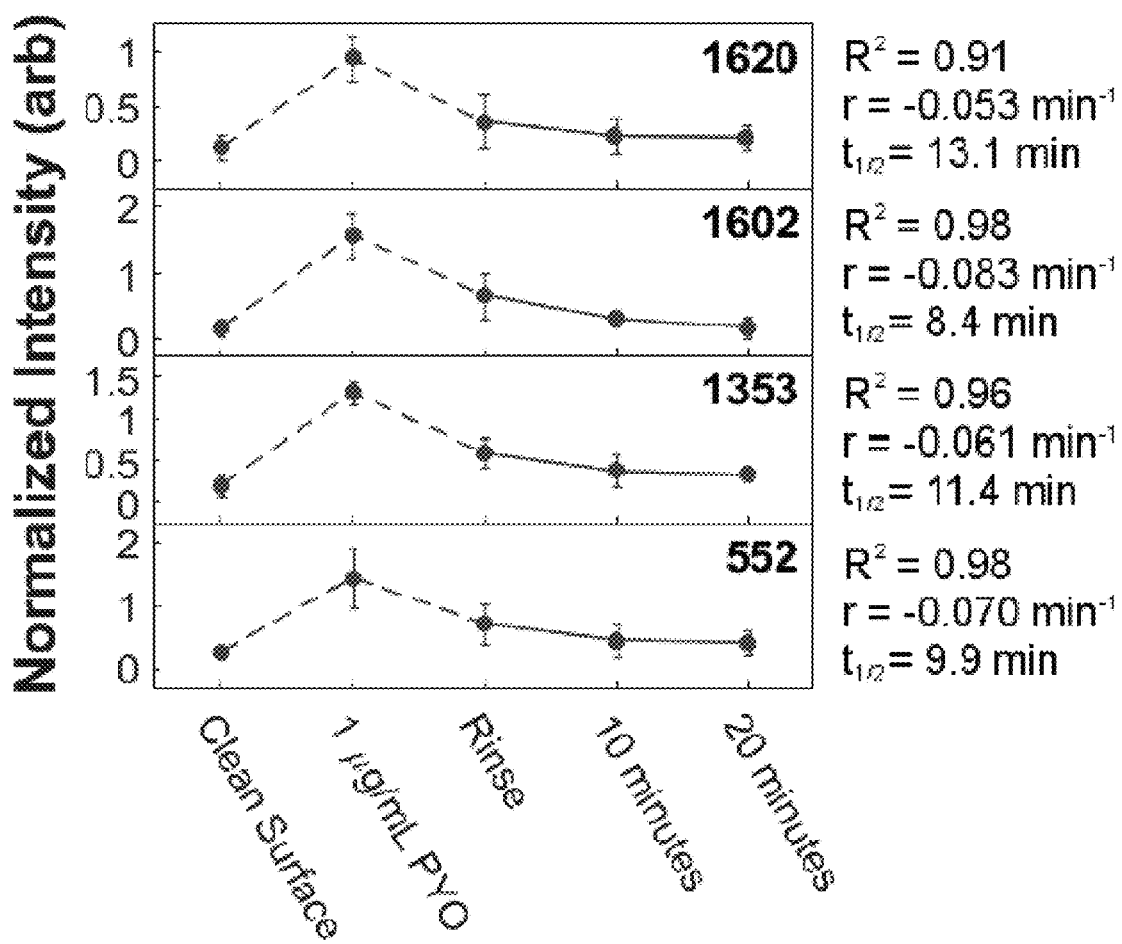
FIG. 19 summarizes decay rates and their corresponding half-life resulting from studies of desorption half-life of pyocyanin and shows that the pyocyanin can be rinsed from the surface and that the metasurface of embodiments can be reused.

Monitoring Biofilm Formation via Pyocyanin Quantification. In some embodiments, microfluidic channels are integrated with SERS metasurface substrates of the application, as illustrated in FIG. 18A, to perform in-line sampling of biofilm's effluent, thus enabling rapid quantitative detection of bacterial metabolites, such as pyocyanin, as a means to longitudinally monitor biofilm growth. Here, *P. aeruginosa* biofilms were grown in tryptone broth (TB) medium according to established procedures. Effluent from the biofilm growth channel was delivered to a microfluidic channel with metal nanoparticle oligomers assembled on the surface according to the method of the application (FIG. 18A). Every 3 hours, 200 SERRS spectra were collected in the effluent with a total acquisition time of 2 min, thus eliminating the need for performing chloroform extraction and incubating, or evaporating the solvent on SERS surfaces. To quantify pyocyanin, a suitable predictive model was generated by repeating PLS analysis on the training dataset acquired using the appropriate collection parameters for TB media (as opposed to LB in planktonic cultures growth) as reported in the Materials and Methods section below. The resulting LOD from this analysis is 10 ng·mL$^{-1}$. Using the model, pyocyanin was detected in the SERRS signal above the LOD starting between 6 and 9 h after inoculating as observed in FIG. 18B. Thus, the time of quantification (TOQ) falls within this range. Pyocyanin concentration after 9 h was determined to be 24 ng·mL$^{-1}$ (115 nM), above the determined LOD. The half-life of pyocyanin desorption from the surface was determined to be on the order of 11 min from subsequent SERS measurements from samples immersed in water, exposed to 1 µg·mL$^{-1}$ (4.8 µM) pyocyanin, rinsed, and re-immersed in water, as shown in FIG. 19. Thus, the calculated concentrations are indicative of the instantaneous production of pyocyanin in the biofilm growth channel. Investigation of results generated from the model shows that some spectra at 3 and 6 h reveals Raman bands associated with pyocyanin above the background. By analyzing the individual spectra, it was determined that 7.8 and 14.3% of the spectra at 3 and 6 h, respectively, show a pyocyanin concentration above the background; representative spectra are plotted in FIG. 18C. This fraction increases to 70.3, 96.7, and 100% for the subsequent time points. This is consistent with nonuniform distribution of pyocyanin on the substrate surface at low concentrations. Hence, while the averaged concentration of pyocyanin calculated for the set of Raman spectra at 3 and 6 h of the biofilm growth lies below the LOD, a fraction of those spectra shows that pyocyanin is detected at those early time points. Thus, 3 h is set as the time of detection (TOD). The calculated concentrations of pyocyanin correlate with the time-dependent accumulation of biofilm biomass obtained from the analysis of fluorescence images of the microfluidic growth channels (FIG. 18D). Representative confocal fluorescence images of the growth channels show the initial stages of bacterial cell adhesion (6 h), microcolony formation (10 h), and three-dimensional growth of biofilms above the channel surface (16 h). The biomass and imaging data indicates that the biofilm formation can be monitored reliably after TOQ. More significantly, it reveals that the earliest detection of biofilms, corresponding to TOD, occurs during the initial stages of bacterial cell adhesion, earlier than that observed in fluorescence confocal images.

Bacterial biofilms impart antibiotic resistance and tolerance on constituent cells via several distinct mechanism. These mechanisms are characteristic of bacterial phenotypes and properties of mature biofilms; hence, early treatment with antibiotics can be more effective than equivalent treatment of mature biofilms. Accordingly, the potential for early detection to provide a therapeutic improvement for infection outcomes was assessed by measuring the antibiotic susceptibility of surface-attached bacteria at different stages of biofilm growth. Bacteria exposed to a bactericidal antibiotic, carbenicillin, were differentially susceptible after 10 h of growth, after which their susceptibility decreased significantly with increasing growth time as they transition into a more antibiotic-tolerant state (FIG. 18E); this transition is also captured as the sharp increase in pyocyanin concentration measured from SERRS in FIG. 18B between 9 and 12 h. A control biofilm was grown for 24 h and exposed to phosphate-buffered saline (PBS) instead of carbenicillin indicates no statistically significant difference between the antibiotic susceptibility of cells grown in flow channels for 6 and 10 h. Consequently, the detection of a *P. aeruginosa* infection and intervention at early stages of colonization (<10 h growth) show the potential to substantially improve the effectiveness of antibiotic treatment.

Accordingly, the SERS metasurface prepared according to the method of the application and combined with multi-variate statistical analysis proved to be advantageous for quantitative molecular detection, including in a continuous monitoring microfluidic setup. Specifically, full-wave simulations of near-field enhancements comparing 1 and 2 nm nanogaps show that variation of this parameter is critical to achieve high and reproducible SERS intensity of the meta-surfaces of the application needed to generate reliable training sets for machine learning algorithms. Moreover, large area signal uniformity, low excitation power (14.6 µW), and short integration time (0.1 s) of the SERS metasurface substrates of the application, allow for their integration in a device platform and the rapid acquisition of large data sets for statistical analysis. Therefore, in many embodiments, SERRS substrates of the application exhibit the ability to detect bacterial metabolites, such as pyocyanin, in aqueous media at concentration of 100 pg·mL$^{-1}$ when individual Raman bands for the metabolite are investigated. In many embodiments, in more complex media, PLS analysis of spectral data enables robust quantification of an small molecule analytes spanning as high as 5 orders of magnitude (as shown for pyocyanin) in biologically relevant levels between 1 ng·mL$^{-1}$ and 100 µg·mL$^{-1}$. In many embodiments, integration of microfluidic architectures with SERS substrates of the application facilitates in-line sampling of the effluent medium for longitudinal monitoring of bacterial metabolite concentration during *P. aeruginosa* biofilm formation. For pyocyanin, the measured concentration in the effluent medium correlated with the accumulated biofilm biomass obtained from confocal fluorescence images. More significantly, pyocyanin could be detected as early as 3 h after inoculation. A sharp increase in pyocyanin concentration was observed between 9 and 12 h after inoculation—the time frame corresponds to decreased susceptibility of surface-attached bacteria to bactericidal antibiotic carbenicillin at 10 h. Therefore, in many embodiments, SERS metasurface substrates prepared according to the method of the application combined with analysis using machine learning algorithms may be used as biosensors for label-free detection of microbial production of metabolites associated with QS directly in biological media.

More Specifically—Desorption Half-Life Of Pyocyanin. In order to measure the time for desorption of pyocyanin from sample surface, a SERS substrate was cleaned with IPA and DI water for 1 minute each. Droplet measurements were carried out to collect SERS signals from samples exposed to DI water and 1 µg/mL (4.8 µM) pyocyanin. The substrate and immersion objective were subsequently rinsed with IPA and DI water, and methanol and DI water, respectively, after exposure to pyocyanin. The sample was then immersed in DI water and SERS spectra were acquired at 0, 10, and 20 min after rinsing to monitor the decay of pyocyanin signal. 100 spectra were collected at each step using the collection parameters described in the methods section. The resulting dose-response curves for major pyocyanin bands at 1620 cm$^{-1}$, 1602 cm$^{-1}$, 1353 cm$^{-1}$, and 552 cm$^{-1}$ are illustrated in FIG. 19.

After 20 minutes, two-sample t-tests with significance level α=0.01 show no statistically significant differences between the clean and substrates exposed to pyocyanin at listed vibrational bands (p-value of 0.9662, 0.0653, 0.7442, and 0.0484 for 552 cm$^{-1}$, 1353 cm$^{-1}$, 1602 cm$^{-1}$, and 16°m$^{-1}$, respectively). Thus, this indicates that pyocyanin has appeared to desorp from the surface. To roughly estimate the half-life of this desorption, we fit an exponential decay function to the averaged intensities of each vibrational bands after rinsing (shown in last 3 data points of each curve in FIG. 19).

Experimental Materials and Methods

Materials: Random copolymer Poly(styrene-co-methyl methacrylate)-α-Hydroxyl-ω-tempo moiety (PS-r-PMMA) (Mn=7,400, 59.6% PS) and diblock copolymer poly(styrene-b-methyl methacrylate) (PS-b-PMMA) diblock copolymer PS-b-PMMA (Mn=170-b-144 kg mol$^{-1}$) were purchased from Polymer Source, Inc. (Dorval, Canada). Gold nanospheres diameter of 20 nm and 40 nm with lipoic acid functionalization were purchased from Nanocomposix (San Diego, Calif.). Si(001) wafers with resistivity of 0.004 ohm-cm were purchased from Virginia Semiconductor (Frederickburg, Va.). Hydrofluoric acid (HF) was purchased from Fisher Scientific (Pittsburgh, Pa.). 2-(N-morpholino) ethanesulfonic acid (MES) 0.1M buffer, 1-ethyl-3-[3-dimethylaminopropyl]carbodiimide hydrochloride (EDC), and N-hydroxy sulfosuccinimide (S—NHS) were purchased from Pierce (Rockford, Ill.). Dimethyl sulfoxide (DMSO), ethylenediamine, benzenethiol, toluene, ethanol, isopropanol (IPA), potassium carbonate, and 52-mesh Pt gauze foil were all purchased from Sigma Aldrich (St. Louis, Mo.). Nanopure deionized water (DI) (18.2 MΩ cm$^{-1}$) was obtained from a Milli-Q Millipore System. Single-layer graphene on ultrafine mesh copper TEM grids and 50 mesh copper TEM grids were purchased from Ted Pella.

Nanoantenna Oligomer Substrate Fabrication: Random copolymer PS-r-PMMA and diblock copolymer PS-b-PMMA solution in toluene (1 wt %) were spun coat onto a HF-cleaned, heavily doped Si wafer and annealed at 198° C. to form thin films as described in previous work. PMMA regions were selectively functionalized with amine end groups by first immersing the entire substrate in DMSO and then in ethylenediamine/DMSO solution (5% v/v), both for 5 minutes without rinsing between steps. The Si substrate coated with functionalized copolymer is then washed with IPA for 1 minute and dried under nitrogen.

Lipoic acid-functionalized Au nanosphere solution (0.1 mg/mL, 3 mL) is added to a 10 mL glass beaker. Freshly prepared s-NHS (20 mM) in a IVIES (0.1 M) buffer (35 µL) is added to the beaker and swirled. Next, freshly prepared EDC (8 mM) in a MES (0.1 M) buffer (35 µL) is added to the beaker and swirled. For heated samples, the beaker is placed on a hot plate and brought to 60° C. Similar to previous work a 1 cm×1 cm functionalized copolymer-coated Si substrate is placed into the solution vertically and held in place as the cathode with alligator clips that do not contact the nanosphere solution. One millimeter away from the substrate, a 1 cm×1 cm Pt mesh is placed into the solution vertically and held in place as an anode with alligator clips that do not contact the nanosphere solution. A dc regulated power supply is used to apply a voltage of 1.2 V for 10 min. The substrate, Pt mesh, and beaker are rinsed with IPA for 1 min and dried under nitrogen. This process is repeated with the same substrate and fresh nanosphere solution as described above, but with 25 µL of EDC and s-NHS solution. Two growth steps are necessary to obtain oligomers on resonance at the 785 nm illumination wavelength used for SERS measurements. The second growth step is performed with reduced EDC and s-NHS concentrations to promote anhydride formation, which has been shown to increase with decreased concentration. Oxygen plasma treated samples are treated with a 50 W oxygen plasma etch for 120 s.

Assembly on Alternative Substrates: Substrates fabricated for TEM characterization are fabricated as above, but on copper TEM grids for field-free control substrates and graphene membrane TEM grids for EHD-anhydride samples. PS-b-PMMA block copolymer templates on indium tin oxide (ITO)-coated glass are fabricated identically, but using ITO-coated glass that is oxygen plasma etched at 100 W for 1 min instead of the Si wafer.

Characterization: After nanoantenna oligomers are assembled onto the block copolymer-coated Si substrate, images are collected with a Magellan XHR SEM (FEI) and a CM-20 TEM (Philips).

UV-Vis absorption spectra are taken of nanoantenna oligomer on ITO-coated glass substrates taped (away from the beam path) onto a quartz cuvette. The cuvette is then filled with water and imaged with a Shimadzu UV-1700 absorption spectrometer. Absorption spectra are taken of ITO-coated glass substrates taped (away from the beam path) on to a quartz cuvette filled with DI water.

Raman spectroscopy measurements are conducted using a Renishaw InVia micro Raman system with a laser excitation wavelength of 785 nm for 40 nm Au nanosphere samples. For 20 nm Au nanosphere samples, Raman spectroscopy measurements are conducted using a home built Raman microscopy system with a laser excitation wavelength of 633 nm. In both cases, laser excitation wavelength values are chosen based on simulations from previous work. All SERS measurements are taken at 73 µW with exposure of 0.1 s for map measurements and 1 s for individual spectra on 60° C. EHD-anhydride ('40 nm EPD') substrates. All measurements use a 60× water immersion objective with a 1.2 NA, immersed in DI water. SERS enhancement factors are calculated according to the method of Cai et al. (See, Cai, W. B., et al. Surf. Sci. 1998, 406, 9-22, the disclosure of which is incorporated herein by reference.) Briefly, $N_{SERS}$ is estimated by determining the average surface area of Au via SEM and using an experimentally determined density of BZT on Au surfaces. (See, Aggarwal et al. J. Raman Spectrosc. 2009, 40, 1331-1333, the disclosure of which is incorporated herein by reference.) $N_{Neat}$ is determined by aliquoting neat BZT onto a Si wafer and a glass coverslip affixed on top. The effective height of the BZT (4.07 µm) is determined by measuring the Raman intensity-depth profile, and the bulk density of BZT is used in the calculation. As both the neat and SERS measurements are obtained with the same microscope objective, the EF is not a function of spot size. $I_{SERs}$ and $I_{NEAT}$ are normalized by laser power and acquisition time. Neat BZT measurements are taken with the same laser and a 60× water immersion objective but with 73 mW laser power and 10 s exposure time.

In droplet measurements, as referred to in the main text, a 60× water immersion objective with 1.2 NA is used for illumination and collection. Approximately, 150 µL of solution of interest is transferred onto SERS substrates, and the measurements are acquired with laser power and acquisition time of 7.3 µW and 0.5 s, respectively, over area specified for each case. SERS substrates are cleaned with IPA and DI water for 1 min each and dried under nitrogen between measurements. One substrate was used per set of measurements (concentrations or time points).

For in-line measurements, a 50× objective was used. Measurements are taken with laser power and acquisition time of 14.6 µW and 0.1 s, respectively. Illumination and collection were done through the SERS microfluidic channel.

Spectra Processing and Analysis: Raman scattering spectra processing and analysis were performed off-line using MATLAB R2016b (The MathWorks Inc, Natrick, Mass.). Each spectrum undergoes baseline correction, smoothing with Savitzky-Golay, and normalization to the average intensity of Si second-order vibrational band, reported between 920 and 1045 cm$^{-1}$, from the substrate. This allows for comparison of different samples where slight intensity variations may arise because of the deviations in optical collection in the experimental setup. Specifically, the range of 920 and 970 cm$^{-1}$ was used because of the appearance of pyocyanin ring stretching vibrational band at 975 cm$^{-1}$. When preparing SERRS spectra for full-spectrum PLSs regression, a constant k=1.0067 was added to the processed signals to eliminate negative values in the calibration matrix associated with variations due to noise. This is necessary as signals are then log-transformed before analysis with PLS regression. PLS regression combines characteristics of principal component analysis with multiple linear regression to predict a set of dependent variables from a large set of independent variables.

Finite Element Simulations: Full-wave simulations (frequency domain finite elements method solver) are implemented in CST Microwave Studio (CST AG). Absorption and scattering are simulated by several nanosphere oligomers: dimer, linear trimer, linear quadrumer, close-packed quadrumer, close-packed hexamer, and close-packed octamer. A schematic of the simulation conditions is presented in FIG. 10C. Au nanospheres with diameter of 40 nm are used with permittivity from the Drude model with parameters extracted from Grady et al. (See, e.g., Grady, N. K., Halas, N. J. & Nordlander, P. Chem. Phys. Lett. 399, 167-171 (2004), the disclosure of which is incorporated herein by reference.) A 0.9 nm gap between nanospheres is used, consistent with both observation and the modeled length of an anhydride linker. The nanospheres were previously shown to be partially embedded in PMMA, with the PMMA layer thickness set to 40 nm, and the center of the nanospheres 8 nm above the layer. Below the PMMA layer is 150 nm of layer of ITO on top of a 2 µm layer of glass. The relative electric permittivity of water, PMMA, glass, and ITO used in the simulations are 1.77, 2.47, 2.3207, and 3.1827 respectively, and adapted from Moerland, respectively. (See, Moerland, et al. Subnanometer-Accuracy Optical Distance Ruler Based on Fluorescence Quenching by Transparent Conductors. Optica 2016, 3, 112-117, the disclosure of which is incorporated herein by reference.) The permittivity in the gap region is uncertain, as the excitation source will probe a volume composed of the anhydride linker, aqueous solution, and copolymer environment. In order to account for this, a parameter sweep of the gap permittivity is performed using the dimer configuration, and the permittivity that best corresponds to the observed dimer structure peak at 686 nm is determined to be 2.25. This parameter is reasonable based on an estimate of the average permittivity of the materials and further verified by the correspondence between the trimer configuration's simulated plasmon resonance and the trimer peak observed in the EHD-anhydride sample.

Oligomers are excited with plane wave illumination at normal incidence with electric field polarization along the axis of the linear oligomers, and the absorption cross section of the structure is determined.

Atomistic Simulation: A periodic supercell is constructed containing a total of 288 gold atoms arranged in six layers of a (111) plane. The simulation box dimensions in the xy plane are roughly 20 Å×17 Å. The size of the simulation cell in z dimension varies between 23 and 32 Å to provide different nanogap distances. The number of water molecules is changed from 30 to 120 to fill the free space between organic molecules in the nanogap. The number of water molecules depends on the concentration of organic molecules and gold surface-to-surface distance. All organic molecules, both lipoic acid and O-acylisourea, are first constructed in AVOGADRO software and the configurations are minimized using the UFF force field. Subsequently, these organic molecules are inserted inside the nanogap such that sulfur atoms are next to the gold surface. Simulations are performed using the ReaxFF potential, a reactive force field designed based on the notion of bond-order parameter and the electronegativity equalization method to update variable charges at each step of the atomistic simulation. Here, a transferable set of ReaxFF parameters that were trained for biomolecules and their interaction with gold surfaces is used. The LAMMPS simulation package is use in all MD calculations. MD simulations are carried out in the canonical (NVT) ensemble using a Nosé-Hoover thermostat with a relaxation constant of 0.01 ps. The time step in MD simulations is set to 0.1 fs.

In simulations for carbon-oxygen distance analysis, nine periodic simulation boxes are constructed with gold-gold surface distances of 11, 15, and 20 Å, each containing three levels of OA-LA concentrations. In low and medium concentrations respectively, one OA is attached to one side of the Au slab, while one and four LA molecules are placed at the other surface. For the high-concentration case, two OA molecules on one side face four LA groups on the other side of the gold slab. The number of water molecules are adjusted in each simulation to achieve ambient conditions at equilibrium. Potential energy minimization is first performed to relax the structure. Subsequently, the position of the water molecules is relaxed in a 20-ps-long MD simulation, while the rest of the atoms are fixed in their position. Afterward, the system is further relaxed in canonical ensemble for 100 ps. A 400-ps-long production phase produces the MD trajectory saved at intervals of 0.1 ps.

For MEP simulations, three simulation boxes with nanogaps of 13, 15, and 17 Å are first constructed. One OA molecule is placed on one surface and one LA group on the other. The number of water molecules is adjusted to obtain ambient pressure at equilibrium. The purpose of these simulations is to capture a reasonable initial and final state on each side of the energy barrier for NEB calculations. To accelerate the formation of the intermediate state, a bias harmonic potential is applied between reactive carbon and oxygen atoms. This spring should be strong enough to keep the reactive core in the proximity of the transition state. Also, a large spring constant biases the configuration space by preventing the organic molecules from properly relaxing to accommodate short C—O distances. Here the value of the spring constant is determined to be roughly 100-200 kcal/mol Å2. The equilibrium C—O distance is found to be around 3 Å. Since the number of degrees of freedom corresponding to atoms in organic molecules is large, it is critical to capture proper initial configurations in z(I, II, and III) states to obtain a smooth MEP. The initial and final states for NEB calculations are taken right before and after transition states during a small window of time (less than 100 fs) in biased MD simulations. The metastable intermediate complex (II) (FIG. 9) is found to be stable for at least 20 ps in MD simulations at room temperature. Therefore, the reaction path is divided into two separate stages, one from state I to state II and the other from state II to state III; see states in FIG. 9. Since the reaction does not directly involve water molecules, they are not included in NEB calculations. This also helps with NEB's difficulty in determining the transition state in the presence of soft degrees of freedom. For the second stage of the chemical reaction, it is enough to elevate the temperature to 600 K to reach state III. To perform NEB calculations, the standard LAMMPS implementation of a two-stage NEB procedure is used. First, the standard NEB is used by constructing replicas with linear interpolation and imposing interreplica forces to find the MEP. Subsequently, a barrier-climbing technique is used to find the true transition state.

*P. aeruginosa* Cell-Free Supernatant Preparation: Wild-type *P. aeruginosa* (strain PA14) shaking culture supernatant was used to measure pyocyanin production over time. PA14 was streaked onto the lysogeny broth (LB, EMD Millipore) agar plates from frozen glycerol stocks and grown overnight at 37° C. Shaking cultures were inoculated from single colonies on the LB plate into 5 mL of liquid LB and grown at 37° C. on an orbital shaker overnight. Shaking culture (50 µL) was diluted into 24 mL of 10 g·L$^{-1}$ tryptone media (Bacto tryptone, BD Scientific), and this subculture was grown at 37° C. on an orbital shaker. Aliquots were taken periodically from the shaking subculture for optical density measurements. To measure pyocyanin production, *P. aeruginosa* conditioned medium was isolated by centrifuging the 2 mL cultures at 15 000 g and passing the resulting supernatant through a 0.2 µm PES vacuum filter (Corning). The filtered supernatants were dropped onto the SERS substrates and measured within 1 h from their collection time.

Fluidic Device Fabrication and Biofilm Growth: The microfluidic device consists of two channels, one for the biofilm and the other for the SERS metasurface substrate of the disclosure. Microfluidic channels for the biofilm were made by bonding the plasma-activated surfaces of polydimethylsiloxane with a glass slide. The SERS substrate and a glass slide are separated by an adhesive spacer of 100 µm thickness (3M 415) with channel design laser cut (Epilog Fusion Laser Cutter) in the adhesive layer.

*P. aeruginosa* biofilms for in-line detection of pyocyanin were grown in the above microfluidic devices as previously described using a *P. aeruginosa* strain constitutively expressing yellow fluorescent protein (YFP). (See, Bhattacharjee, A.; et al., ACS Appl. Mater. Interfaces 2017, 9, 18531-18539, the disclosures of which are incorporated herein by reference.) *P. aeruginosa* cells were seeded with no flow in the biofilm growth channel for 2 h. The fluid feed was then switched to sterile tryptone media, and the outlet of the channel was connected to the SERS channel input. The 0 h SERRS measurements were collected once the in-line device is fully connected, prior to start of the flow. Media was then pulled through the in-line detection device at 10 µL·h$^{-1}$, and SERRS spectra were collected at the indicated time points. Identical biofilms were grown and imaged in the flow cells to measure the time-dependence of the biofilm growth. The biofilm volume was obtained from Volocity imaging analysis software (PerkinElmer) of confocal fluorescence images of the YFP-producing biofilms. SERRS collection parameters are described below.

Antibiotic Susceptibility Measurements: *P. aeruginosa* biofilms were grown for 10, 15, and 24 h on glass coverslips submerged in 2 mL of TB supplemented with 3 g·L$^{-1}$ NaCl in sterile, six-well tissue culture plates (Fisher Scientific). After the indicated growth time, the growth media was aspirated and the biofilms on the coverslips were rinsed once with PBS while still in the wells. The PBS rinse solution was then aspirated and replaced with 600 µg·mL$^{-1}$ carbenicillin (minimum inhibitory concentration in *P. aeruginosa* strain PA14 128 µg·mL$^{-1}$) in PBS or PBS only for the control. Biofilms were soaked in the antibiotic or control solutions for 3 h, rinsed again with PBS, and then stained with live/dead cell viability assay stains, propidium iodide and Syto 9 (Fisher Scientific) at 2 µM final concentration each, for 15 min. Coverslips were rinsed once more in PBS, removed from the wells and placed face down on a microscope slide for confocal fluorescence imaging. The fraction of dead cells was calculated using the biovolumes of each color channel (red and green) obtained from Volocity imaging analysis software (PerkinElmer) of confocal fluorescence images of biofilms.

At 6 h biofilm growth, the washing steps described above removed all cells from the coverslips. Instead, the antibiotic susceptibility of surface-attached bacteria was measured from cells grown in microfluidic devices. After 6 h of growth, as described above for pyocyanin detection experiments, the input line was changed from TB to 600 µg·mL$^{-1}$ carbenicillin in PBS for 3 h. The input line was then changed again to BacLight for 15 min and finally PBS for 30 min, after which the cells attached to the channel surface were imaged and the dead cell fraction was quantified by counting the individual cells of each color channel.

Figure 20A:
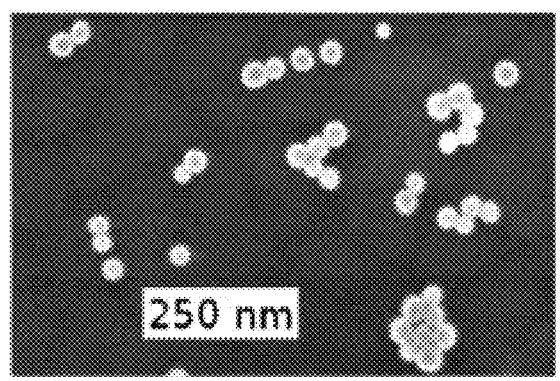
FIGS. 20A through 20D illustrate image analysis to estimate the degree of oligomerization for the nanospheres on the metasurfaces according to embodiments.
Figure 20B:
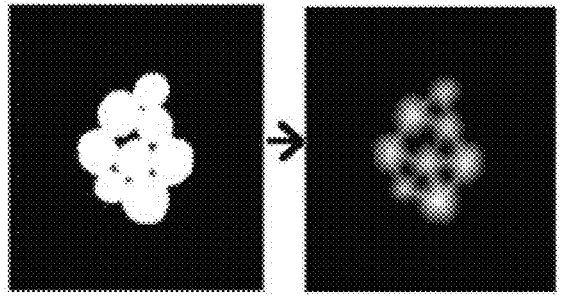
Figure 20C:
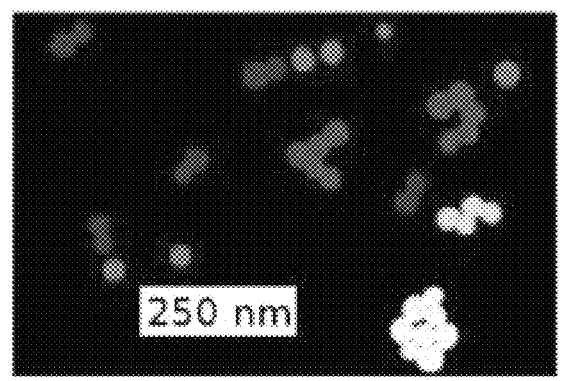
Figure 20D:
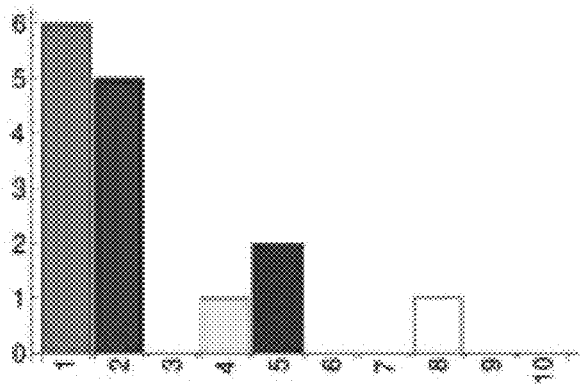

Analysis of Degree of Oligomerization: To analyze the degree of oligomerization of a given oligomer and the number of nearest neighbors of a given Au nanosphere, Wolfram Mathematica™ is implemented for image analysis. SEM images, an example shown in FIG. 20A, are first binarized, and oligomers are distinguished from one another as being separate collections of foreground pixels, or morphological components. Single Au nanospheres are identified through their circularity, defined as the ratio between the equivalent disk perimeter length and the perimeter length of a polygon formed by the centers of each perimeter element, only morphological components over a certain threshold of circularity are determined to be single nanospheres. The remaining morphological components are then divided into component nanospheres using a modified Euclidean distance transform approach, which is designed for implementation in SEM images, where edge effects can make identification of small nanoparticles in close packed structures difficult. For each morphological component, the original image is again binarized using local adaptive binarization, shown in the left side of FIG. 20B. A Euclidean distance transform (figure distance transform) then reveals the nanoparticle centers as local maxima, shown in the right side of FIG. 20B. The maxima are then used to determine the center of each nanosphere and a distance threshold is used to determine the number of nearest neighbors of a given nanosphere. From these images the number, density, and nearest neighbor statistics are obtained as shown in FIGS. 20C and 20D, respectively.

Figure 21A:
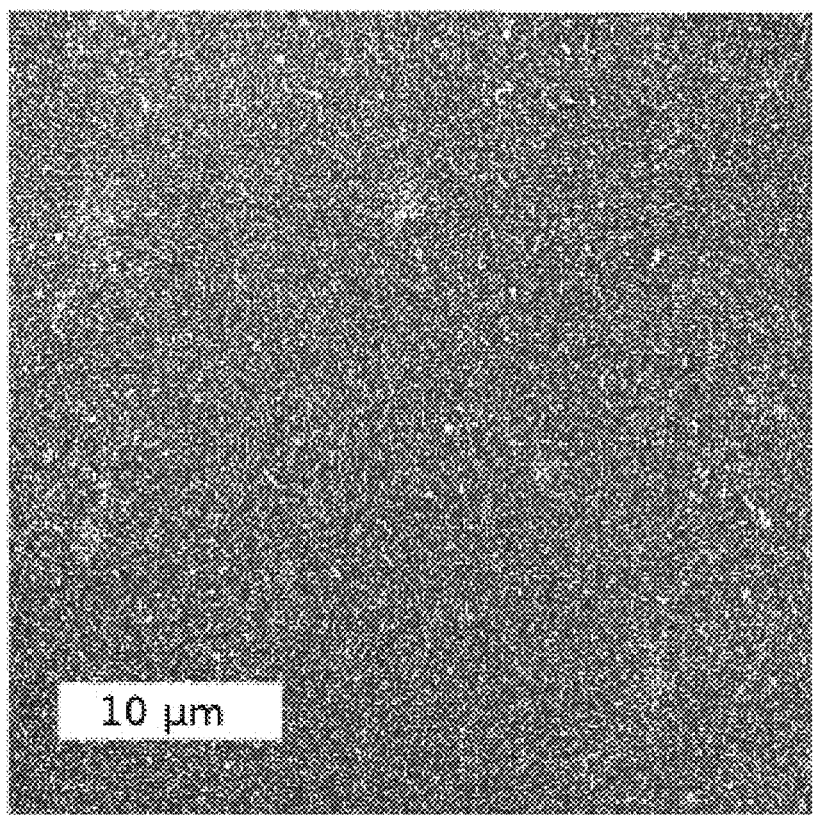
FIGS. 21A and 21B provide SEM images of the metasurfaces assembled according to embodiments to illustrate the large scale uniformity of the fabrication method.
Figure 21B:
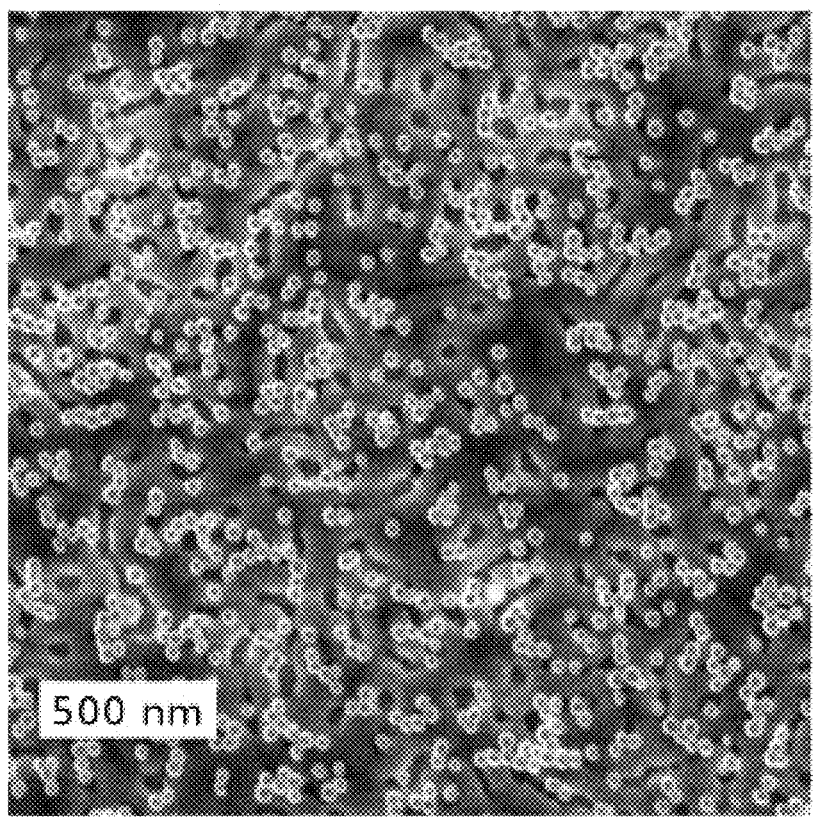

SEM of Nanoantenna Oligomers: In addition to the SERS data shown in FIG. 14, the large-scale uniformity of the nanoantenna oligomers can also be observed from scanning electron microscope (SEM) images. For example, FIG. 21A shows a 50 µm×50 µm SEM image of a '40 nm EPD' sample. The image shows that no very large-scale aggregates of Au nanospheres are observed, and that oligomer density variations are essentially random and small in scale. FIG. 21B shows a 2.2 µm×2.2 µm SEM image of a '40 nm EPD' sample. From this image, the relatively narrow distribution of oligomerization provided by the electrohydrodynamically driven anhydride crosslinking between Au nanospheres can be seen. Additionally, Au nanospheres that are over the PS domains can be observed, apparently not linked through a peptide bond to the PMMA domains of the deposition template. The close packing of oligomers is also observed in most of the oligomers in this image.

Figure 22:
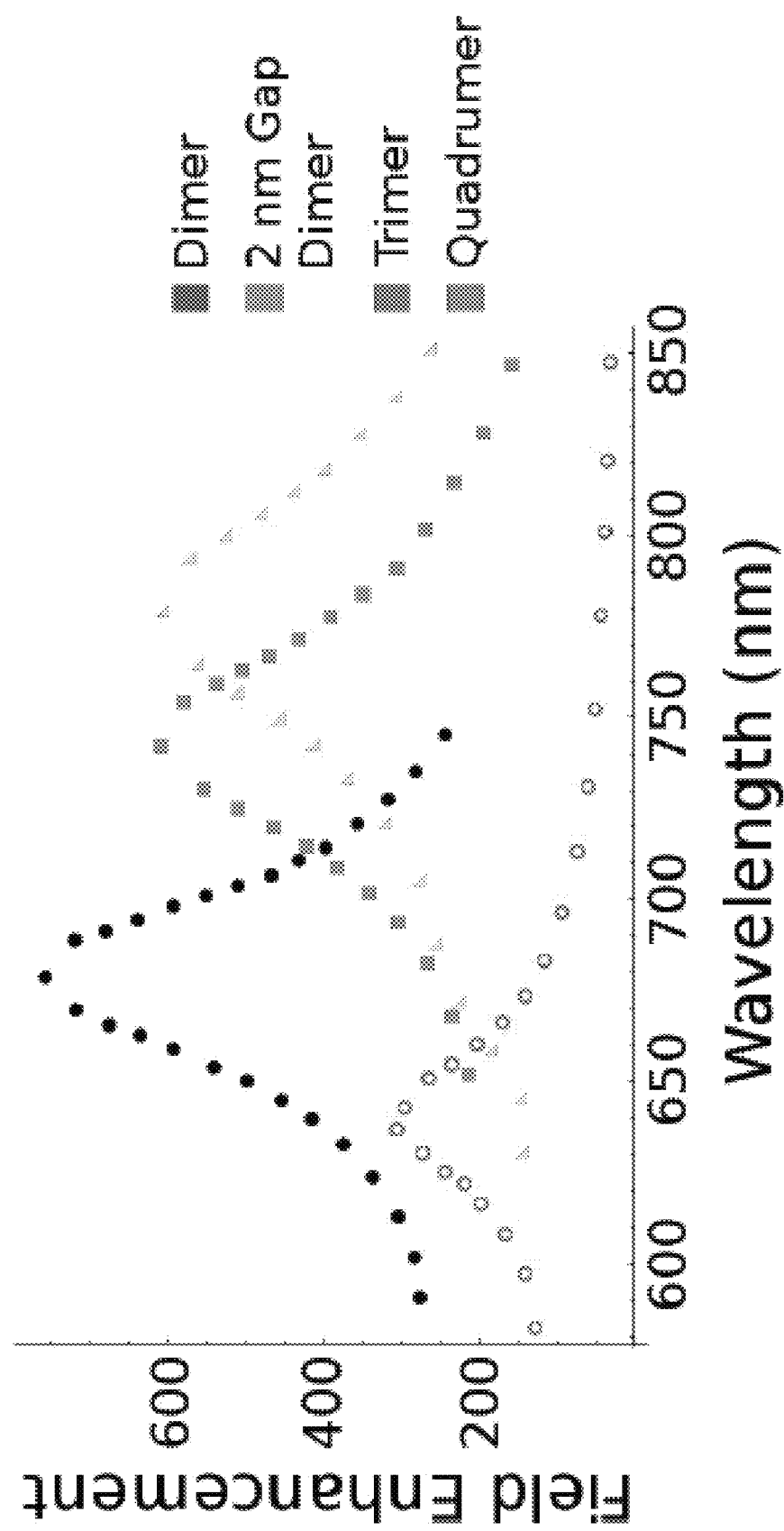
FIG. 22 shows the electric field enhancement of nanosphere oligomers of different geometries according to embodiments.

Electric Field Enhancement Measurements. FIG. 22 shows the electric field enhancement of oligomers of different geometries. As surface enhanced Raman scattering intensity is based on field enhancement to the fourth power, the predicted enhancement factor (EF) is $3.3 \times 10^{11}$, $1.3 \times 10^{11}$, and $1.3 \times 10^{11}$ for dimer, trimer, and quadrumer respectively. These values correlate well to the average measured EF of $4.5 \times 10^{10}$ for the '40 nm EPD' samples. Given the low field enhancement of oligomers with larger than 0.9 nm gap spacings, the length of the anhydride bridge, these anhydride bridges seem to play a crucial role in the observed performance of the samples.

Reproducibility and Stability of SERS Response. FIGS. 23A through 23D and FIGS. 24A through 24D provide additional SERS data to further demonstrate reproducibility and stability of SERS response from substrates prepared according to the embodiments. Specifically, FIGS. 23A-23D include SERS spectra acquired from samples undergoing the same treatments as those discussed for FIGS. 11A and 11B. More specifically, reproducible SERS signals (five spectra in each panel represent five distinct samples) were observed for all of: untreated (FIG. 23A), methylamine treated (FIG. 23B), aniline treated (FIG. 23C) and plasma cleaned-benzenethiol treated (FIG. 23D) samples. SERS signal after methylamine treatment (FIG. 23B) has peaks associated with carbonate groups in lipoic acid in the region around 1600 cm$^{-1}$. The data is slightly noisier and is consistent with less ordered molecular orientations in the hotspot.

Figure 24A:
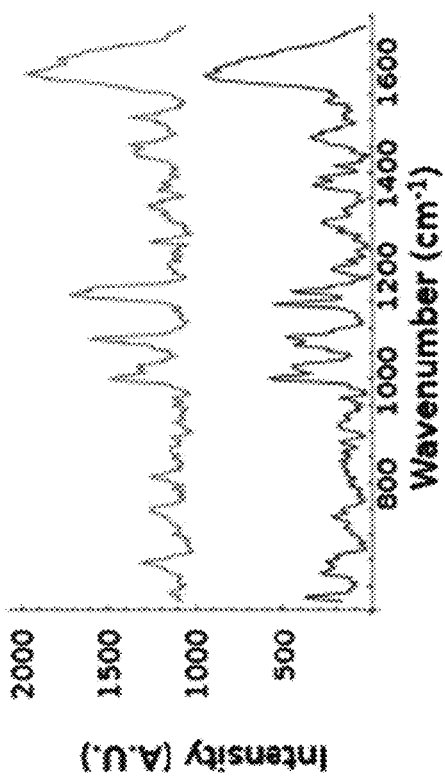
FIGS. 24A through 24D further demonstrate reproducibility and stability of SERS response from metasurface assembled according to embodiments.
Figure 24B:
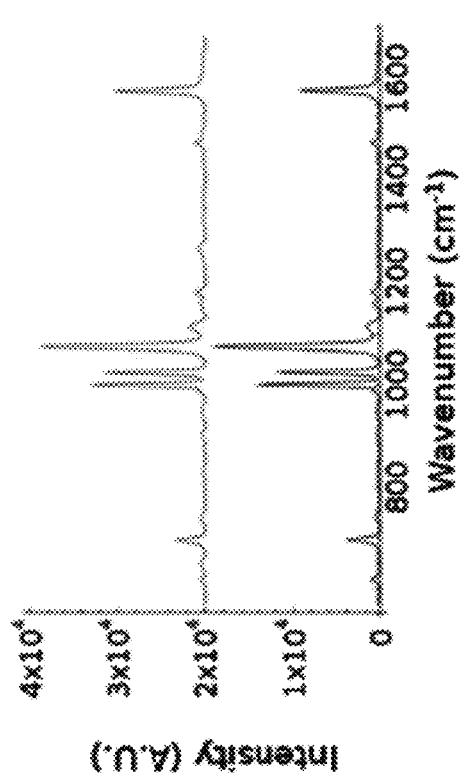
Figure 24C:
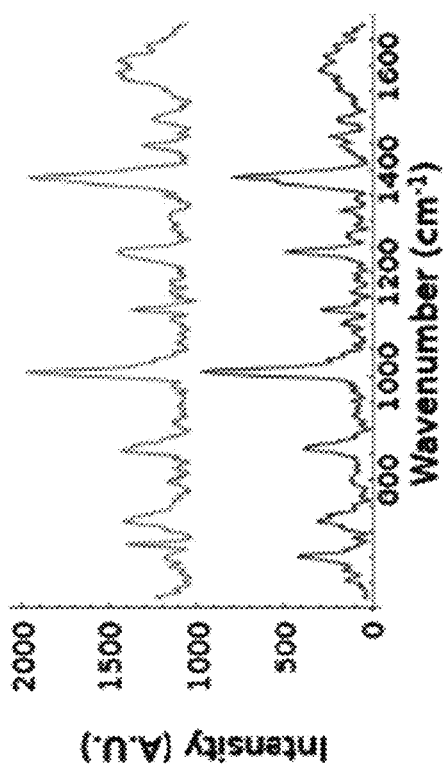
Figure 24D:
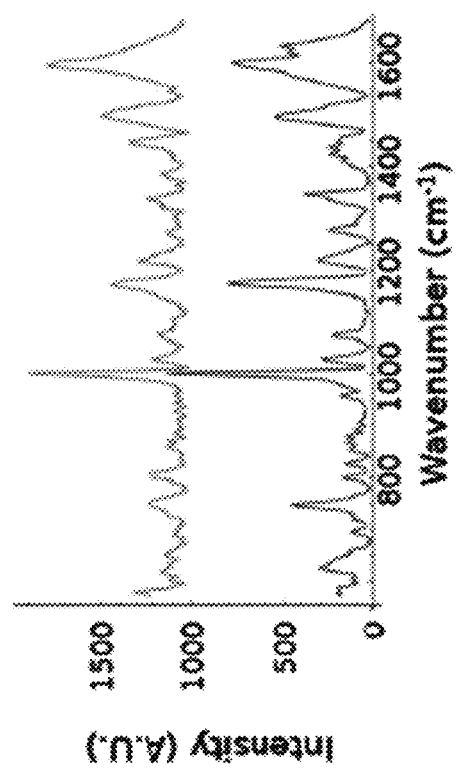

FIGS. 24A through 24D depict SERS spectra before (lower curve in each panel) and after (upper curve in each panel) soaking samples in DI water for 7 days after undergoing the same treatments as discussed for FIGS. 11A and 11B. More specifically, reproducible SERS signals were observed before and after aqueous soak of the following samples: untreated (FIG. 24A), methylamine treated (FIG. 24B), aniline treated (FIG. 24C) and plasma cleaned-benzenethiol treated (FIG. 24D). No additional treatment was performed after the 7 day soak. The similarity of spectra observed after soaking the samples demonstrates that the metal nanosphere oligomers prepared according to the embodiments are stable in aqueous solution.

DOCTRINE OF EQUIVALENTS

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A metasurface comprising:
   an electrode having a surface area,
   a template at least partially functionalized with chemically active functional groups and disposed on the surface area of the electrode;
   at least one cluster comprised of at least two nanospheres disposed on top of the template, wherein each of the at least two nanospheres is crosslinked to one of the following: the template, at least one other nanosphere of the at least two nanospheres of the at least one cluster, or to both via a molecular linker, such that the attachment between the at least two nanospheres of the at least one cluster can be selectively broken on demand to reveal a gap spacing of more than 0.5 nm and less than 3 nm wide therebetween such that at least one hot spot associated with said gap spacing is formed; and
   wherein the metasurface is characterized by an electric field enhancement in a hotspot region being defined by the disposition of the at least one hot spot.

2. The metasurface of claim 1, wherein the metasurface is characterized by a high cluster density, a uniformity of the gap spacing over approximately 75% or more of the surface area, and an electric field enhancement in the hotspot region of above 300.

3. The metasurface of claim 1, wherein the electric field enhancement in the hotspot region is on the order of 600.

4. The metasurface of claim 1, wherein the electrode is comprised of one of the materials selected from the list: silicon, graphene, indium tin oxide-coated glass, copper, nickel, gold or gold coated glass.

5. The metasurface of claim 1, wherein the surface area of the electrode is between 1 $\mu m^2$ and 1 $cm^2$.

6. The metasurface of claim 1, wherein the template is a block copolymer comprising chemically reactive and chemically inert domains or a self-assembled monolayer.

7. The metasurface of claim 6, wherein the template is comprising a diblock copolymer poly(styrene-b-methyl methacrylate).

8. The metasurface of claim 1, wherein the at least two nanospheres are comprised of one of the elements chosen from the list: Au, Ag, or Si.

9. The metasurface of claim 1, wherein the at least two nanospheres are between 20 and 100 nm in diameter.

10. The metasurface of claim 9, wherein the at least two nanospheres are 20 to 40 nm in diameter and are excited by a 633 nm excitation source.

11. The metasurface of claim 9, wherein the at least two nanospheres are 40 to 100 nm in diameter and are excited by a 785 nm excitation source.

12. The metasurface of claim 1, wherein the at least two nanospheres are 40 nm in diameter.

13. The metasurface of claim 1, wherein the gap spacing is 0.5 to 1.5 nm wide.

14. The metasurface of claim 1, wherein the gap spacing is approximately 0.9 nm wide.

15. A biosensor for detection of bacterial metabolites comprising:
    a metasurface comprising:
    an electrode having a surface area;
    a template at least partially functionalized with chemically active functional groups and disposed on the surface area of the electrode;
    at least one cluster comprised of at least two nanospheres disposed on top of the template, wherein each of the at least two nanospheres is crosslinked to one of the following: the template, at least one other nanosphere of the at least two nanospheres of the at least one cluster, or to both via a molecular linker, such that the attachment between the at least two nanospheres of the at least one cluster can be selectively broken on demand to reveal a gap spacing of more than 0.5 nm and less than 1.5 nm wide therebetween such that at least one hot spot associated with said gap spacing is formed; and
    wherein the metasurface is characterized by an electric field enhancement in a hotspot region of above 300 and detection limits of parts per billion or lower, the hot spot region being defined by the disposition of said at least one hot spot; and
    a sensor configured to interrogate the metasurface to achieve detection of metabolites in contact with the metasurface.

16. A microfluidic device for longitudinal detection of bacterial metabolites comprising:
    at least one microfluidic channel comprising a metasurface, wherein
       the metasurface comprises:
          an electrode having a surface area;
          a template at least partially functionalized with chemically active functional groups and disposed on the surface area of the electrode;
          at least one cluster comprised of at least two nanospheres disposed on top of the polymeric template, wherein each of the at least two nanospheres is crosslinked to one of the following: the template, at least one other nanosphere of the at least two nanospheres of the at least one cluster, or to both via a molecular linker, such that the attachment between the at least two nanospheres of the at least one cluster can be selectively broken on demand to reveal a gap spacing of more than 0.5 nm and less than 3 nm wide therebetween such that at least one hot spot associated with said gap spacing is formed; and
       wherein the metasurface is characterized by an electric field enhancement in a hotspot region of above 300 and detection limits of parts per billion or lower, the hot spot region being defined by the disposition of said at least one hot spot; and
    wherein the at least one microfluidic channel is connected to at least one analyte source, a pump, a laser, and a spectrometer.

* * * * *